United States Patent
Chiao et al.

(10) Patent No.: US 9,031,658 B2
(45) Date of Patent: May 12, 2015

(54) WIRELESS NEURAL RECORDING AND STIMULATING SYSTEM

(75) Inventors: Jung-Chih Chiao, Grand Prairie, TX (US); Thermpon Ativanichayaphong, Valencia, CA (US); Yuan B. Peng, Grapevine, TX (US); Ji Wei He, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1170 days.

(21) Appl. No.: 12/251,368

(22) Filed: Oct. 14, 2008

(65) Prior Publication Data

US 2009/0157141 A1 Jun. 18, 2009

Related U.S. Application Data

(60) Provisional application No. 60/979,851, filed on Oct. 14, 2007.

(51) Int. Cl.
| | | |
|---|---|---|
| *A61N 1/00* | (2006.01) | |
| *A61N 1/372* | (2006.01) | |
| *A61N 1/05* | (2006.01) | |
| *A61N 1/36* | (2006.01) | |
| *A61N 1/375* | (2006.01) | |

(52) U.S. Cl.
CPC ........... *A61N 1/37229* (2013.01); *A61N 1/0551* (2013.01); *A61N 1/36017* (2013.01); *A61N 1/36071* (2013.01); *A61N 1/36082* (2013.01); *A61N 1/37205* (2013.01); *A61N 1/3756* (2013.01)

(58) Field of Classification Search
USPC ...................................... 607/40–46
See application file for complete search history.

(56) References Cited

U.S. PATENT DOCUMENTS

| | | | | |
|---|---|---|---|---|
| 2003/0144710 | A1* | 7/2003 | Haugland et al. | 607/48 |
| 2004/0167580 | A1* | 8/2004 | Mann et al. | 607/17 |
| 2005/0075680 | A1 | 4/2005 | Lowry et al. | 607/45 |
| 2005/0080462 | A1* | 4/2005 | Jenkins et al. | 607/58 |
| 2005/0283200 | A1* | 12/2005 | Rezai et al. | 607/42 |
| 2006/0190051 | A1 | 8/2006 | Gerber et al. | 607/41 |
| 2007/0203547 | A1* | 8/2007 | Costello et al. | 607/59 |
| 2008/0249430 | A1* | 10/2008 | John et al. | 600/544 |
| 2008/0306359 | A1* | 12/2008 | Zdeblick et al. | 600/302 |
| 2008/0319506 | A1* | 12/2008 | Cauller | 607/46 |

OTHER PUBLICATIONS

U.S. Appl. No. 60/713,680.*
International Search Report, pp. 1-3 (Dec. 22, 2008).
Written Opinion, pp. 1-4 (Dec. 22, 2008).

* cited by examiner

*Primary Examiner* — Scott Getzow
(74) *Attorney, Agent, or Firm* — Stephen J. Terrell; Parks Wood, LLC

(57) ABSTRACT

Apparatus and methods are provided for the management of neural activity in an individual. Nerve activity is sensed and correlated with sensations such as pain. In response and without requiring input from the individual, although external input is contemplated, a signal is transmitted to another component for electrical stimulation that alters neural activity. Also, the modulation of the signals between the sensor and stimulator may be modified by a third component independently, independent of, or including user inputs.

20 Claims, 36 Drawing Sheets

136

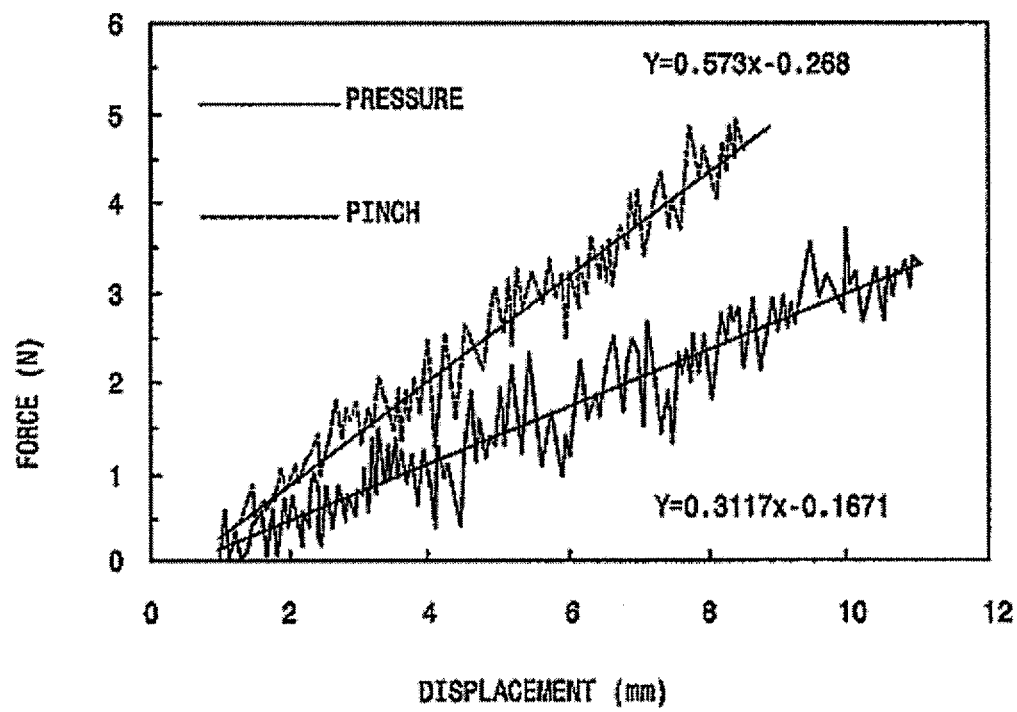
FIG. 13
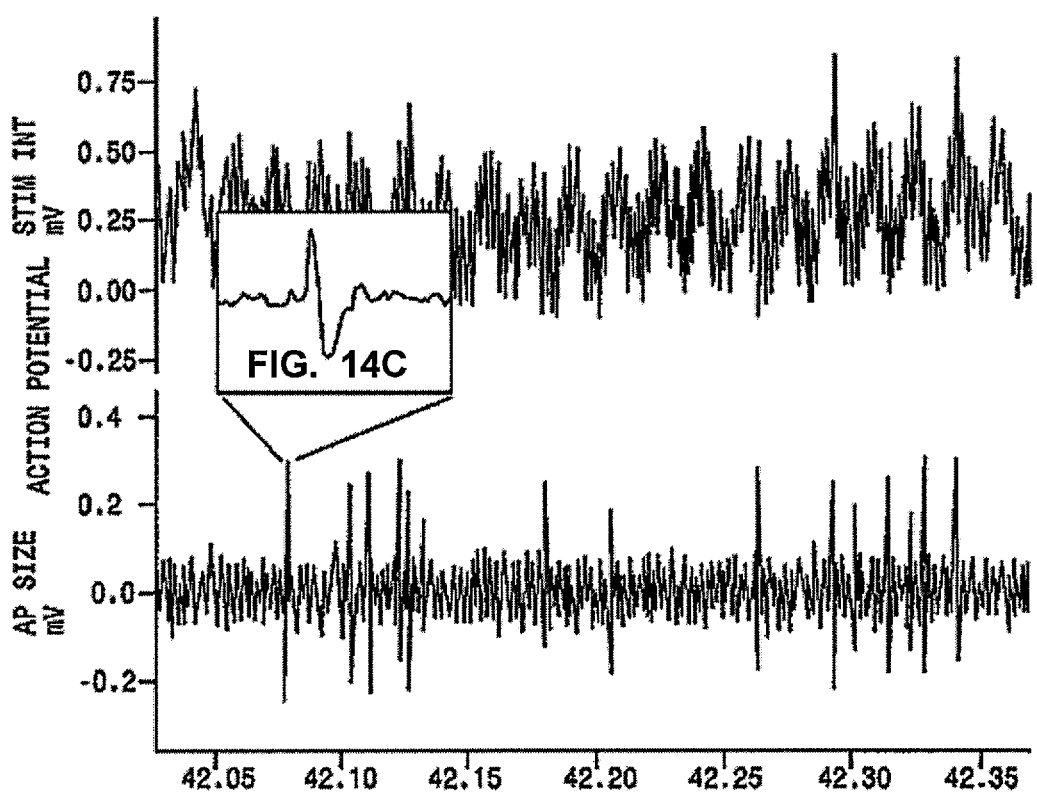
FIG. 14A
FIG. 14C
FIG. 14B

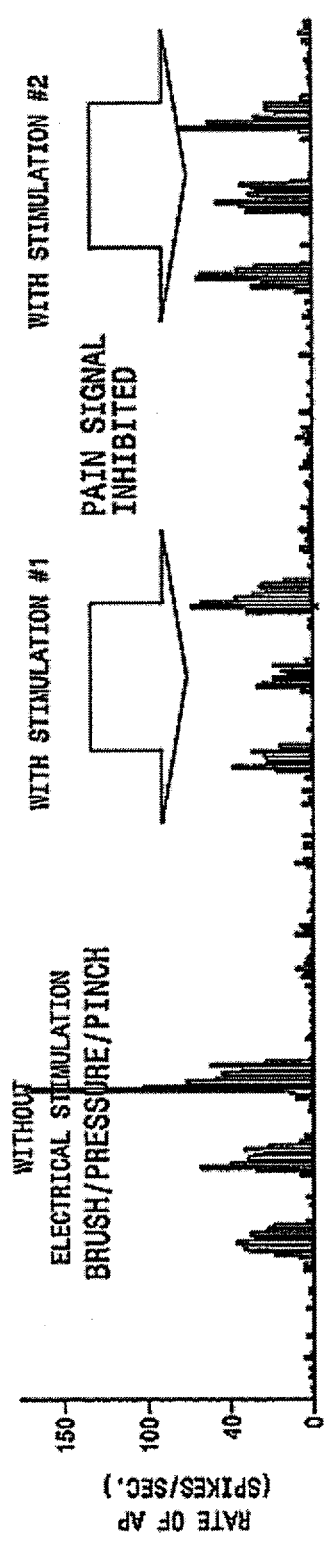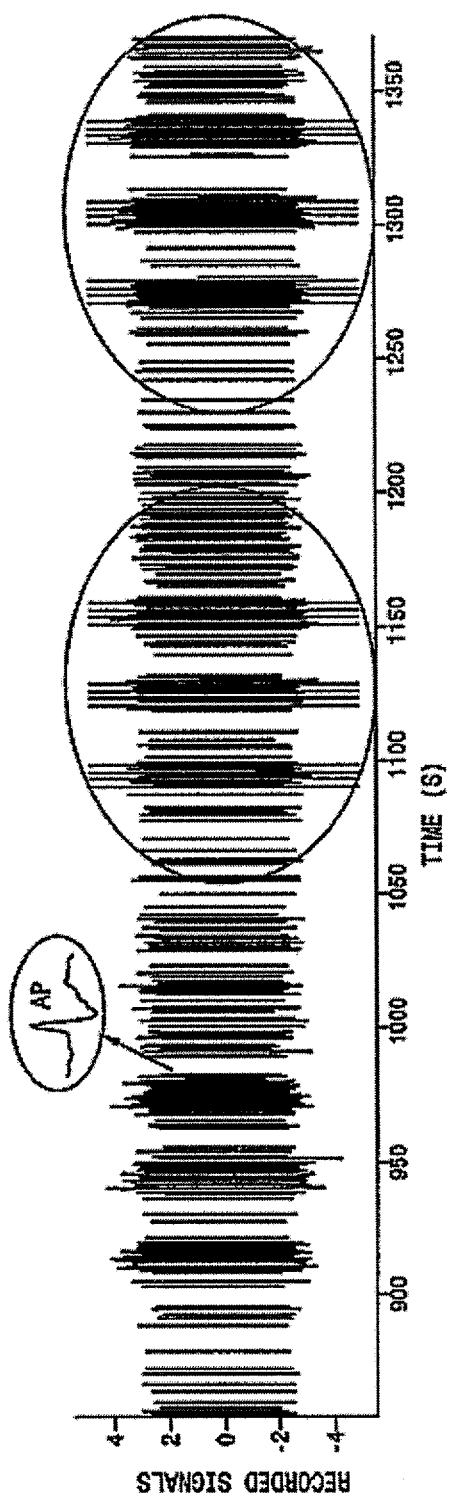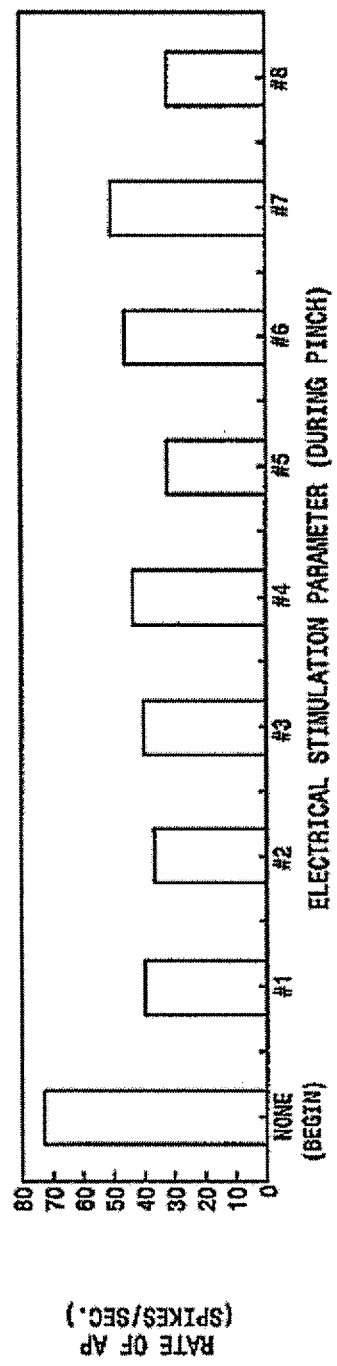
FIG. 16A
FIG. 16B
FIG. 16C

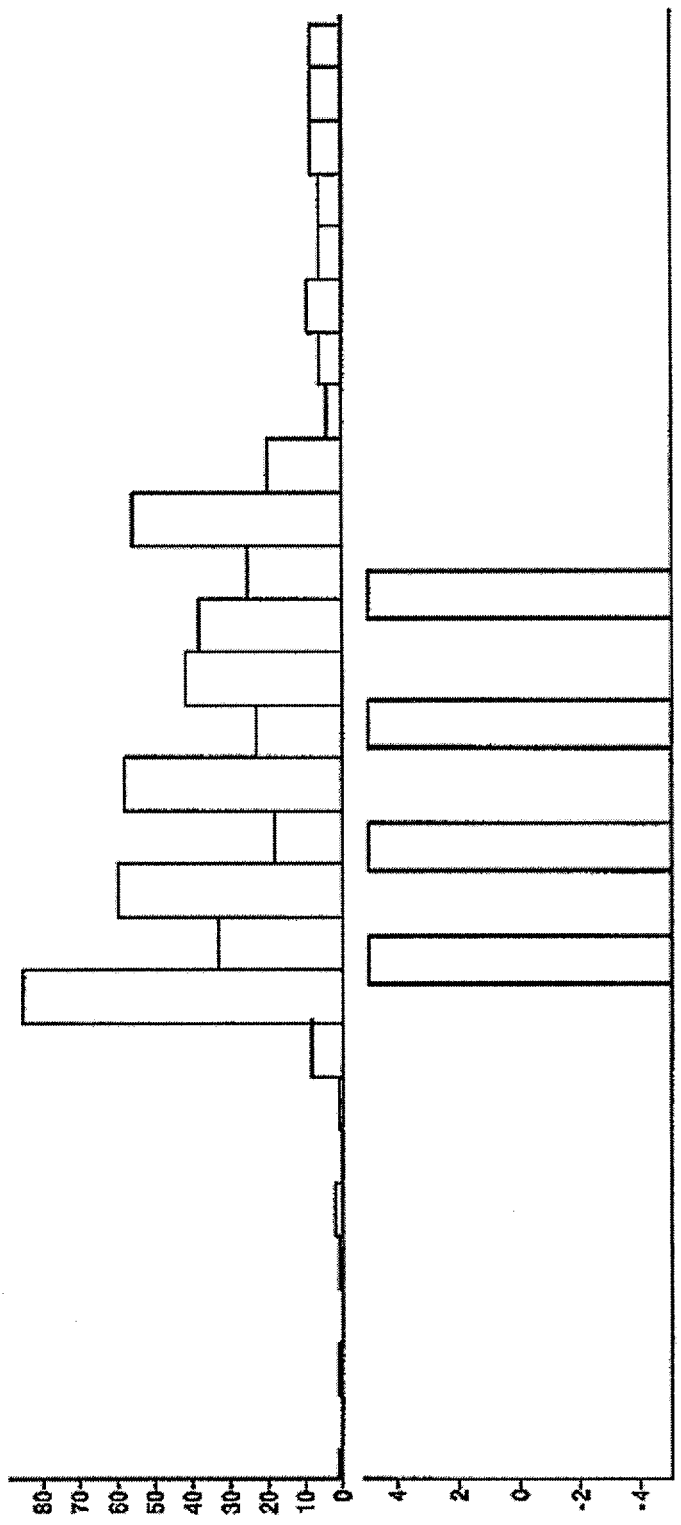
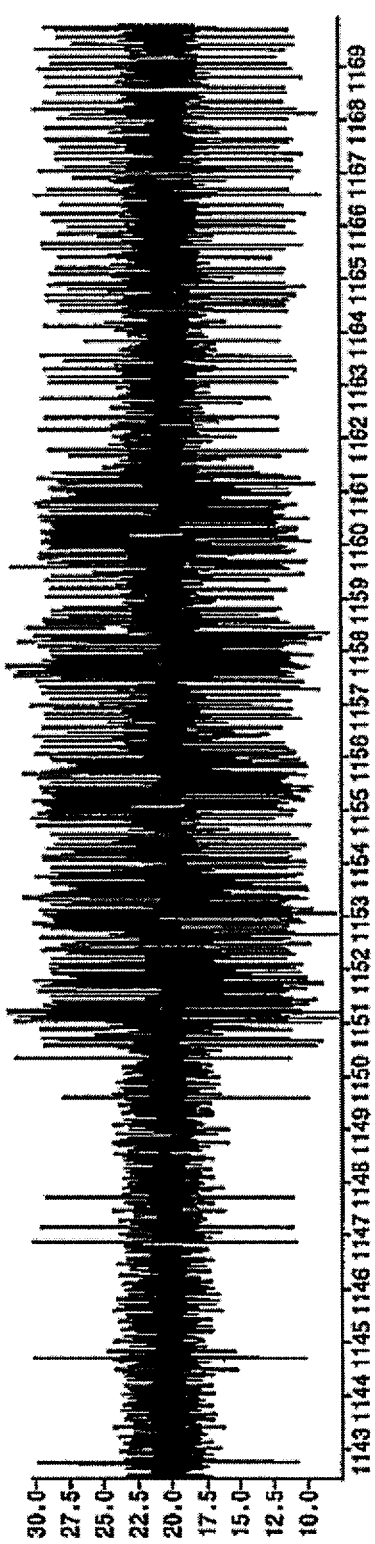
FIG. 19A
FIG. 19B
FIG. 19C

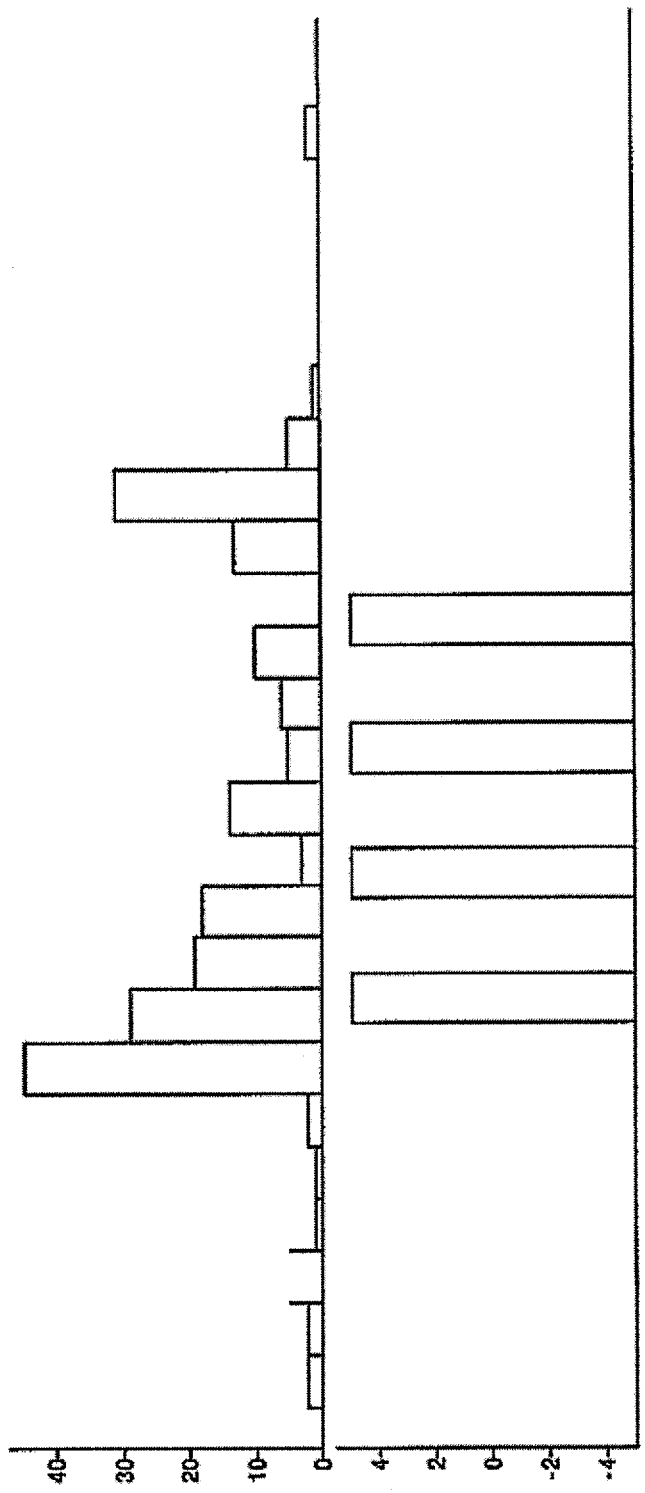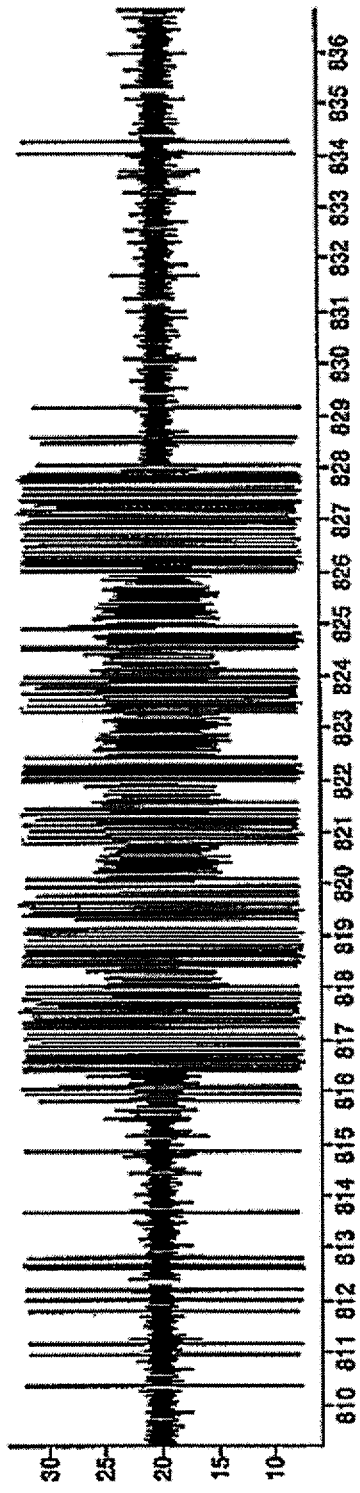
FIG. 20A
FIG. 20B
FIG. 20C

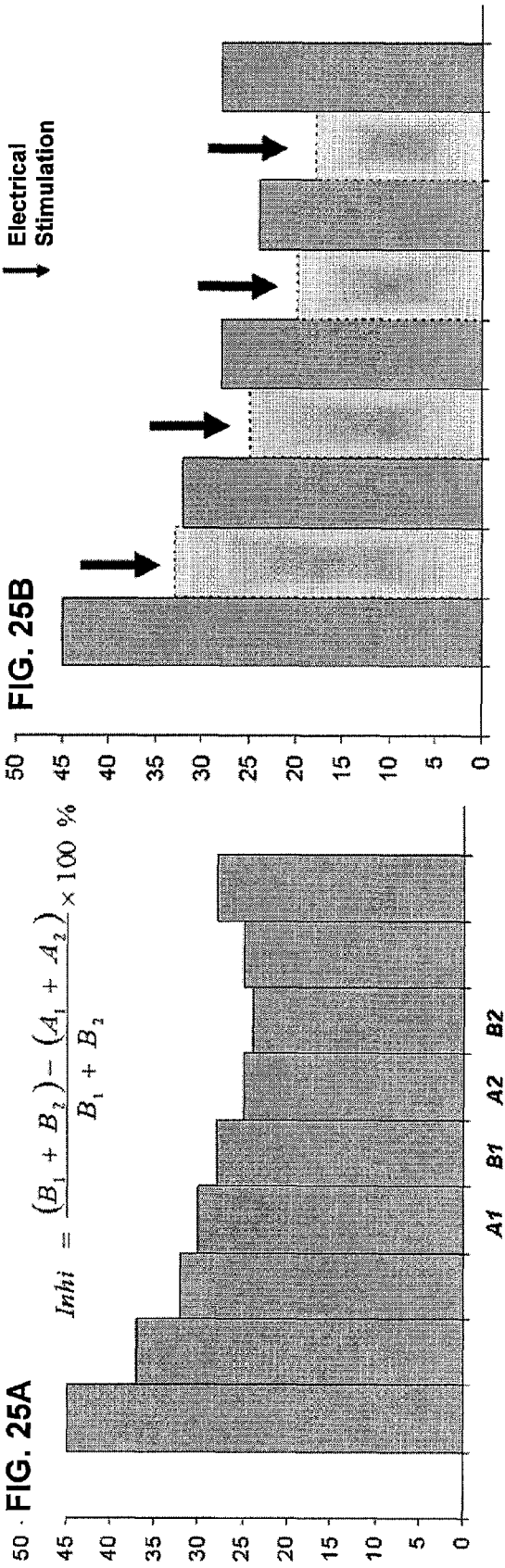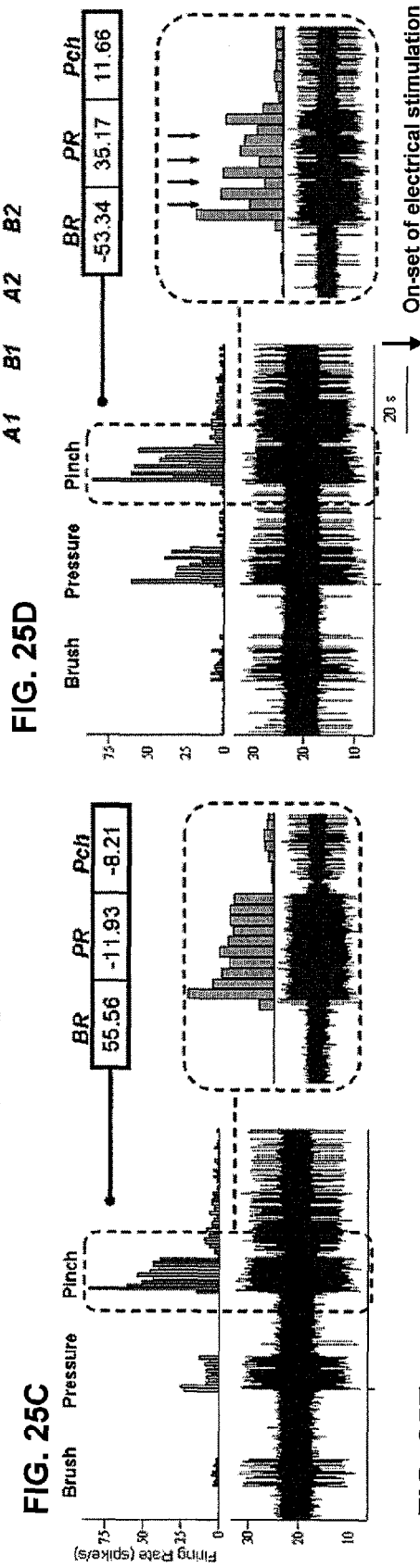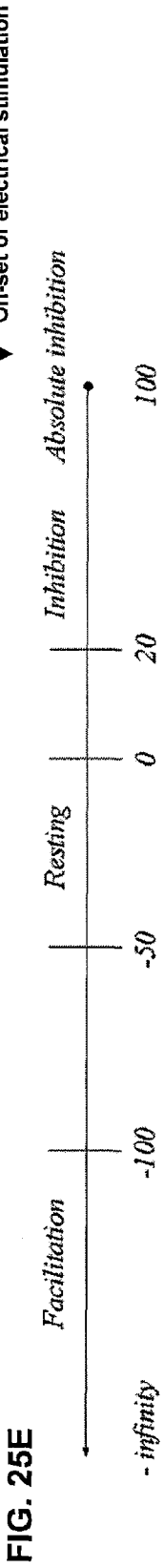

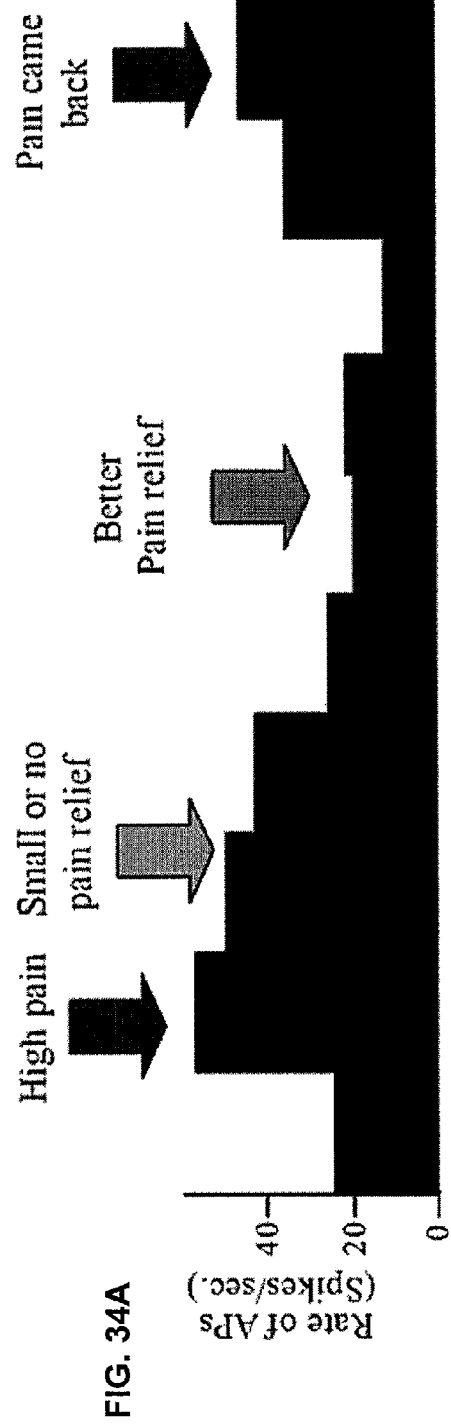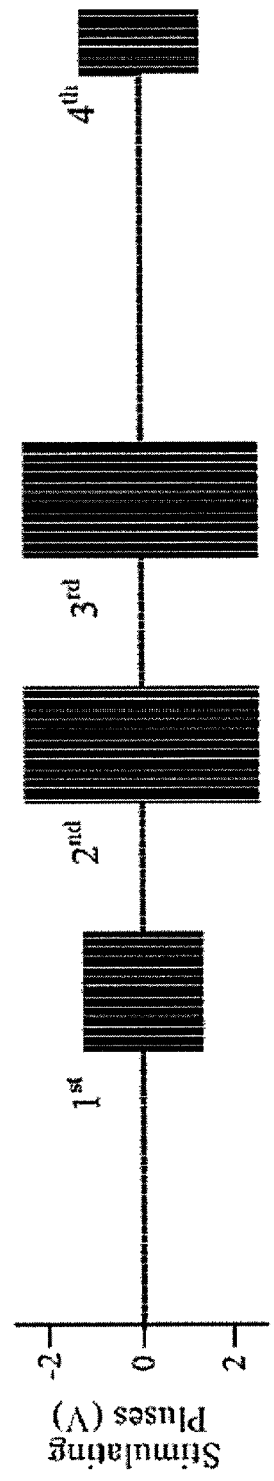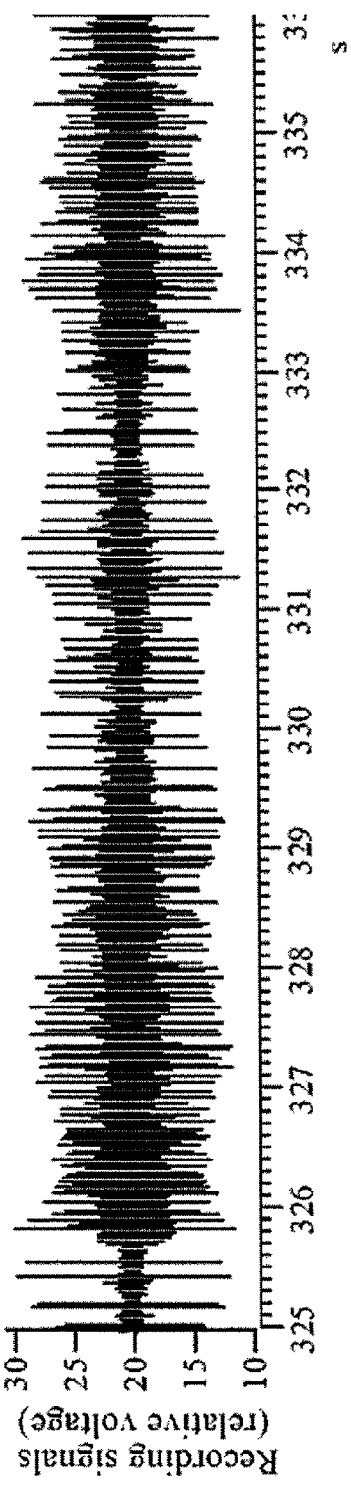
FIG. 34A
FIG. 34B
FIG. 34C

Average silhouette value =0.523

Average silhouette value =0.599

Average silhouette value =0.513

WIRELESS NEURAL RECORDING AND STIMULATING SYSTEM

CROSS-RELATED APPLICATIONS

The present application claims priority from U.S. Application Ser. No. 60/979,851, filed Oct. 14, 2007, herein incorporated by reference.

GOVERNMENT FUNDING

This invention was supported in whole or in part by Grant No. ECS-0601229 from the National Science Foundation. The government has certain rights in this invention.

BACKGROUND OF THE INVENTION

The field of the invention is a wireless system, and more particularly, a wireless system for recording and stimulating.

Chronic pain is a debilitating health problem. The impacts of pain suffering are not only on individual's life quality but also on the family, society and the national economy. Several major approaches have been used to ease chronic pain, including surgical implantation of neurostimulators. Neurostimulation on the spinal cord or primary motor cortex delivers low levels of electrical signals directly to nerve fibers or neurons to affect the neuronal membrane excitability, in turn to suppress pain signals by opening and closing of ion channels. This form of therapy is attractive because it is selective for pain and has few side effects compared to chemical approaches. Therapeutic studies have shown when used on carefully selected chronic pain patients, neurostimulation could significantly improve pain relief and reduce use of narcotic medications.

Conventional stimulators are open-loop systems, where doctors can only obtain the results for pain management from patients' verbal feedback. Stimulating signals are programmed during device installation and cannot be modified after the patients leave the hospital. Further, tethered integration of neurorecorders and neurostimulators in a patient's body is not suitable for safe, long-term use because wired connections degrade over time. The present invention attempts to solve these problems, as well as others.

SUMMARY OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

A wireless system is disclosed for neural recording and stimulation that can provide an optimized signal feedback control. Neural signals are recorded and directly transmitted to an implantable stimulator that delivers pulses that alter neural signals to mitigate pain. A remote processing device also may be used to process wireless signals received from the sensor under preset or real-time user-controlled conditions before transmission to a stimulator in addition to or instead of the signals provided by the sensor.

BRIEF DESCRIPTION OF THE FIGURES

The foregoing summary, as well as the following detailed description of preferred embodiments of the invention, will be understood when read in conjunction with the appended drawings. For the purpose of illustrating the invention, there is shown in the drawings embodiments which are presently preferred. It should be understood, however, that the invention is not limited to the precise arrangements and configurations shown.

FIG. 13 is a graph shows measurements representing graded mechanical stimulation applied to hindpaw receptive fields to simulate pain. Pressure was applied by a venous bulldog clamp (6 cm long, straight, serrated jaws). Pinch was applied by an arterial bulldog clamp (3 cm long, straight, serrated jaws). The applied force (F) as a function of displacement (x) of each clamp was measured.

FIG. 14A is a representative trace recorded in a lumbar spinal cord dorsal horn neuron by a wireless sensor as disclosed herein; FIG. 14B is the trace of FIG. 14A after the received data is filtered as described; and FIG. 14C shows a filtered recorded spike from the trace shown in FIG. 14B that is counted as a pain signal.

FIG. 16A shows a trace reflecting the AP rate (spikes/s) inhibition of lumbar spinal cord dorsal horn neurons during two stimulations to rat motor cortex during the application of mechanical stimuli to the footpad. Stimulation 1 was with 20 pulses at 2.5 V and 200 Hz and lasting 1 millisecond and 5 millisecond intervals. Stimulation 2 differed from Stimulation 1 by a pulse duration of 2 milliseconds; FIG. 16B is a trace of the recorded spinal cord neuron signals shown in FIG. 16A; FIG. 16C is a rate histogram that compares the average AP rate from different pulse stimulation parameters shown in part in FIG. 16A, where the stimulation parameters are: (set number, pulse numbers, pulse duration, pulse intervals)=(#1, 20, 1 ms, 5 ms), (#2, 20, 2 ms, 5 ms), (#3, 50, 0.1 ms, 5 ms), (#4, 100, 0.1 ms, 5 ms), (#5, 100, 0.05 ms, 5 ms), (#6, 200, 0.1 ms, 5 ms), (#7, 20, 0.1 ms, 5 ms), (#8, 20, 0.05 ms, 5 ms).

FIG. 19A shows the rate histogram of APs (spikes/second) from the representative trace in FIG. 19C before and after the periods of ACC stimulation shown in FIG. 19B; FIG. 19B indicates periods of stimulation in the ACC as disclosed herein; FIG. 19C is a representative trace of AP signals recorded from dorsal root neurons during periods of ACC stimulation.

FIG. 20A shows the rate histogram of APs (spike/second) from the representative trace in FIG. 20C before and after the periods of PAG stimulation shown in FIG. 20B; FIG. 20B indicates periods of stimulation in the PAG as disclosed herein; FIG. 20C is a representative trace of AP signals recorded from dorsal root neurons during periods of PAG stimulation shown in FIG. 20B.

FIG. 25A is a graph of a histogram of dorsal horn neuronal activity induced by pressure or pinch; FIG. 25B is a graph of a typical histogram inhibition induced by electrical stimulation; FIGS. 25C and 25D are graphs of a representative trace of inhibition scores; and FIG. 25D is an interpretation of inhi as described on the y-axis.

FIGS. 32D 32C and 32E 32D are graphs of the rate of APs and recording signals during pressure stimulus with a feedback loop.

FIG. 34A is a graph of the automatic pain reduction using various stimulating doses and the recorded action potential signals; FIG. 34B is a graph of the stimulating pulses; and FIG. 34C is a graph of the rate of the action potentials.

DETAILED DESCRIPTION OF THE PREFERRED EMBODIMENTS

The apparatus and process can be understood more readily by reference to the following detailed description of the apparatus and process and the Examples included therein and to the Figures and their previous and following description. While particular reference is made to the removal of selenium, it is to be understood that the elemental removal process and apparatus may be applied to other elements, as described below.

A wireless system is disclosed for neural recording and stimulation that can provide an optimized signal feedback control. Neural signals or action potentials (APs) are recorded and directly transmitted to an implantable stimulator that delivers pulses that alter neural signals to mitigate pain. AP's are generated from ions and flow through the cell membrane of neurons, with a bandwidth signal of 500-3 kHz. Neurons communicate by the rate of action potential in the number of spikes per sec. The perception of pain requires the propagation of APs. Other types of neural signals may be sensed, including, but not limited to, action potential trains (spike times or full waveforms), intracellular membrane voltage, local field potentials, signals defining the stimulus, and the like.

The system may be used for any pain management, including, but not limited to, addiction, post-surgical pain, nociceptive and psychogenic pain, chemotherapy, cancer, Alzheimer's Disease, neurological disorders, transplant rejection, Arthritis pain, Back pain, Neuropathic pain, due to recovered injuries, nerve damages, physiological conditions, illness, and the like. Alternatively, the system may be used for any area requiring nerve stimulation including, but not limited to (1) deep brain stimulators for Parkinson's Disease, Multiple Sclerosis, Alzheimer's Disease, depression, Tourette syndrome; (2) constant monitoring electrocardiogram (ECG, arrhythmia, bradycardia), Electroencephalography (EEG), Electromyography (EMG), Magnetoencephalography (MEG); (3) spinal cord stimulation and peripheral nerve stimulation; (4) monitoring of seniors' health at homecare; (5) brain-computer interfaces; (6) acupuncture, acupressure, transcutaneous electrical nerve stimulation, and the like. The neural stimulation may comprise a set of stimulation signals applied or delivered to or through target neural structures, target neural projections, and/or one or more target neural populations associated with controlling, influencing, or affecting one or more neurological functions under consideration. Alternatively, the neural stimulation may be directed toward facilitating and/or effectuating at least some degree of symptomatic relief and/or restoration or development of functional abilities in patients experiencing neurologic dysfunction arising from neurological damage, neurologic disease, neurodegenerative conditions, neuropsychiatric disorders, cognitive or learning disorders, and/or other conditions.

Figure 1:
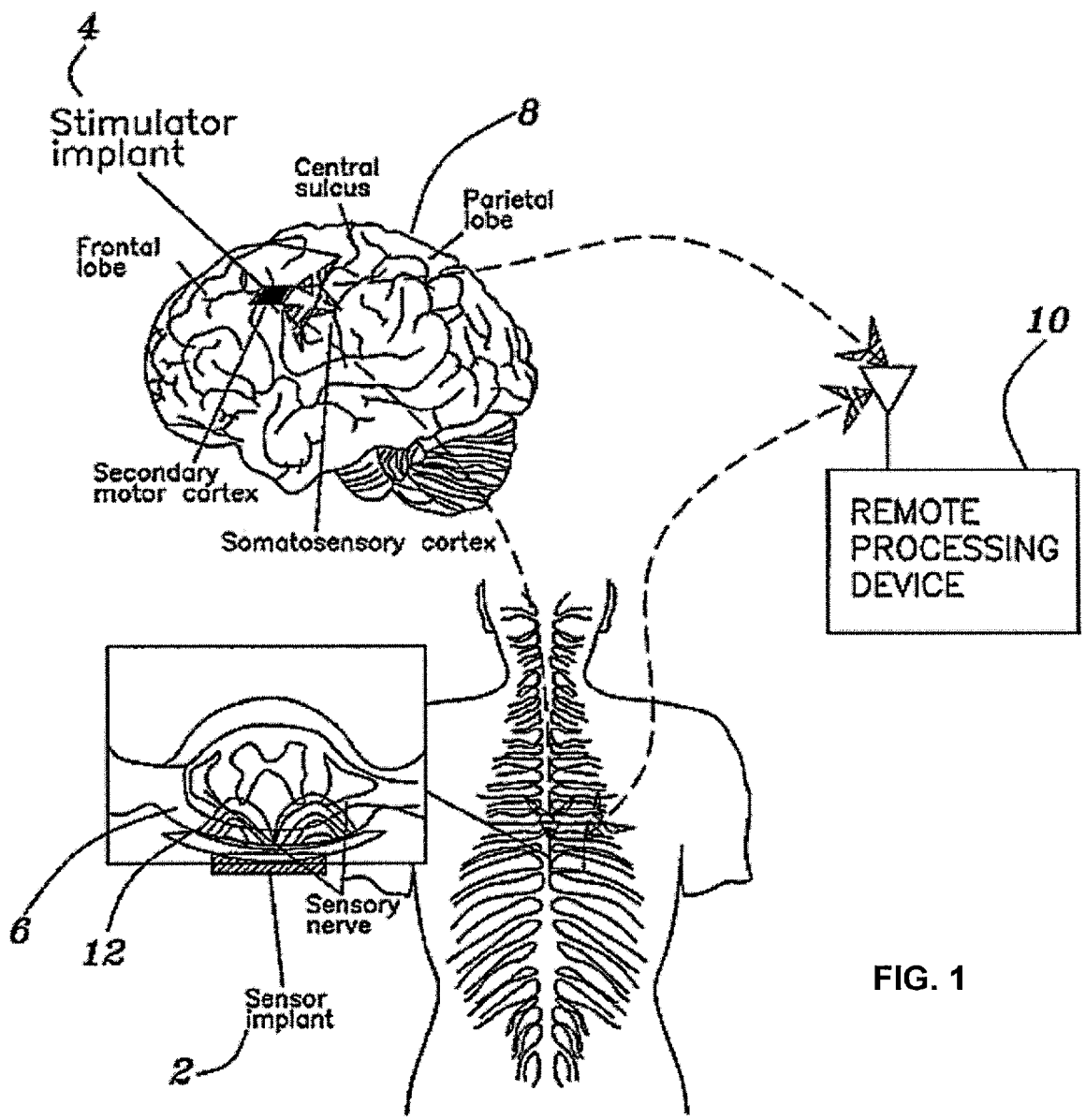
FIG. 1 is a perspective view in somewhat schematic form of a sensor and stimulator in relation to a remote processing device.

An illustrative embodiment of the wireless system and its overall general placement is shown in FIG. 1. The wireless system comprises a sensor 2 and a stimulator 4. In one embodiment, the sensor 2 is placed on the spinal cord, referred generally by numeral 6, of an animal, human, or patient. Alternatively, the sensor 2 may be placed in any portion where pain or neuronal signals needs to be sensed, and optionally, multiple sensors may be placed throughout the body for sensing neuronal signals. The stimulator 4 is placed near the brain tissue, referred generally by numeral 8, of the animal, in one embodiment. Alternatively, stimulator may be placed in any portion of an animal where stimulation is desired, i.e. organs, tissue, injured areas, and the like. Multiple sensor or stimulator implants may be used simultaneously in various parts of the body through a Radio Frequency Identification (RFID)-based body network communication. RFID is an automatic identification method, relying on storing and remotely retrieving data using devices called RFID tags or transponders, explained further below. As illustrated by FIG. 1, the sensor 2 detects neural activity in its location of attachment or implantation, such as in the spinal cords, and wirelessly communicates with the stimulator 4 that in turn generates electrical impulses in its region of attachment or implantation that alters neural activity in its environment to alter neural activity. The alteration of the neural activity may alter the perception of pain by the animal, or other neurological, physiological, or cognitive responses. Optionally, sensor 2 and stimulator 4 also communicate wirelessly with a remote processing device 10 that can receive and send signals from the sensor 2 and the stimulator 4. The remote processing device 10 processes the signals to generate a processed signal with feedback mechanism software for modulation of the electrical stimulus generated by stimulator 4 to affect neural activity.

Providing electrical signal input to sensor 2 is an electrode array 12 that includes a recording electrode 14 inserted within target sensory tissue (e.g., spinal cord), as shown in FIG. 1. Alternatively, the electrode array 12 may be a single electrode or multiple electrodes, including a nerve electrode, a plate electrode, and the like. Alternatively, the sensor may include other sensors, including but not limited to thermal sensor, optical sensors, chemical detectors, and the like. The electrode array 12 includes a reference electrode 16 for comparison of the voltage detected in target sensory tissue, in one embodiment. Because of the small size of neurons and sensory bodies, the recording electrode 14 is relatively thin, ranging from tens of microns to microns, and has a higher impedance, ranging from tens to hundreds of megaohms. A surface metal ball electrode may be the recording electrode 14, alternatively a Tungsten needle electrode to do extracellular recording of APs for the recording electrode 14 may be used. The sensor 2 receives neuronal activity in the form of action potentials (APs), amplifies them, then transmits the signals to a receiver, where the receiver can be either incorporated in the stimulator 4 or remote processing device 10, such as a computer, personal digital assistant (PDA), or other handheld device, such as a cellphones, flash drives with wireless communication capabilities, and the like.

Figure 2:
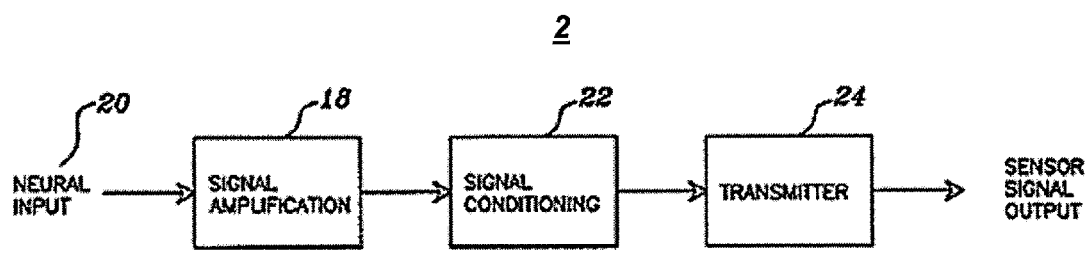
FIG. 2 is a block diagram of a sensor.

FIG. 2 shows a block diagram of sensor 2 that illustrates components of one embodiment of the sensor including a signal amplification 18, a signal conditioning 22, and a transmitter 24. The electrode array 12 feeds neural signals to differential amplifier or integrated instrument amplifier (IA) 18 that in turn feeds the signals to signal conditioner 22 to extract the APs before being passed to transmitter 24. The signal conditioning performs one or more of the following signal processing such as filtering, denoising, classifying, sorting, digitizing, and multiplexing. The choices of conditioning functions depend on the types and the conditions of the neuronal signals. Transmitter 24 transmits filtered signals to stimulator 4, remote processing device 10, or both, as discussed above with regards to FIG. 1. Transmitter 24 may also be a transceiver that is receptive to signals received from remote processing device 10 for modulation of a reference signal.

Figure 3:
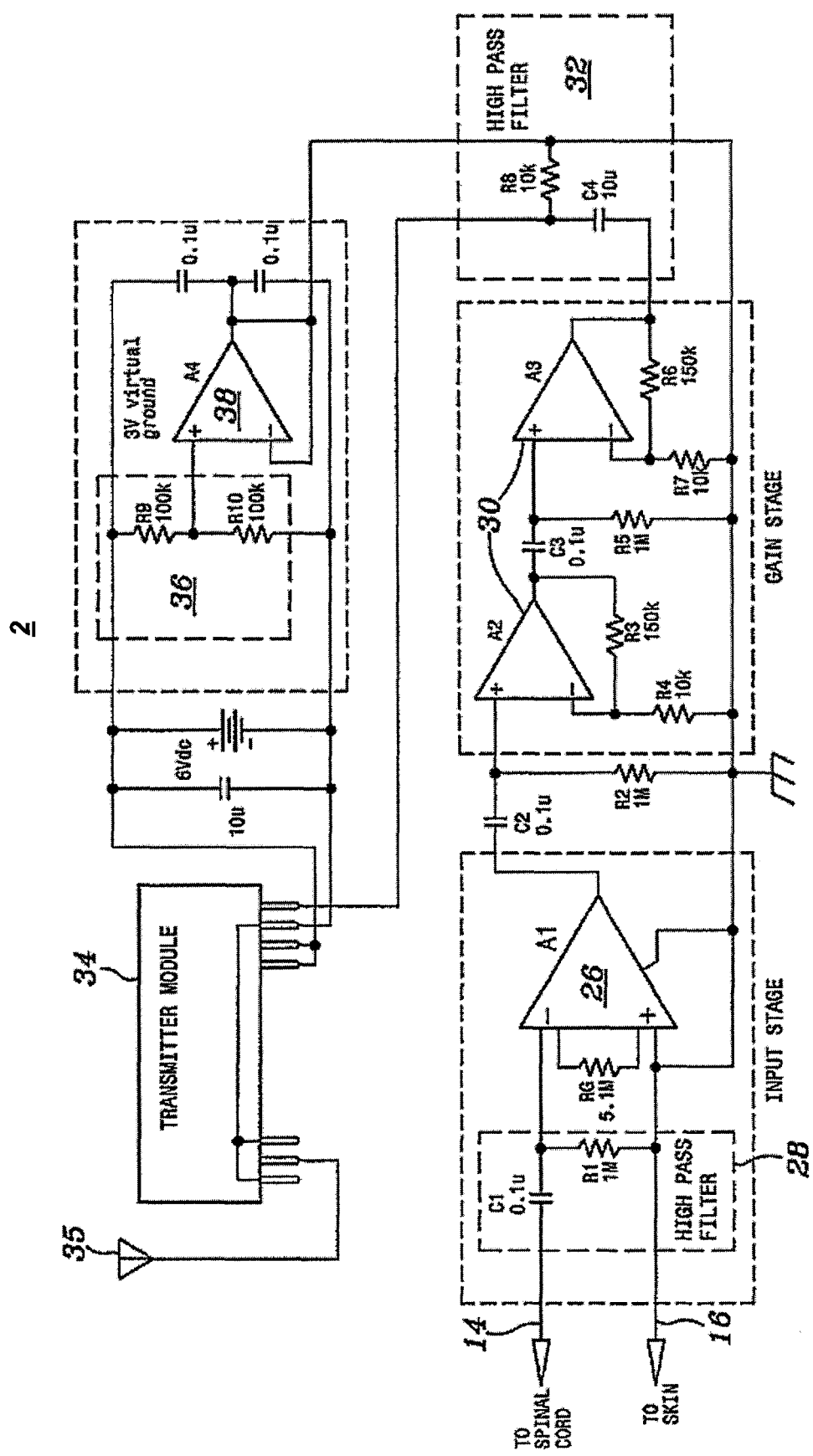
FIG. 3 is a circuit diagram of a sensor.

FIG. 3 provides an illustrative circuit diagram of an embodiment of sensor 2 described generally in FIG. 2. It has been observed that neurons generate weak signals with amplitudes of the extracellular AP in microvolt ranges that are subjected to environmental interference signals. Referring more specifically to signal amplification block 18, to eliminate the interference signals, a differential amplifier 26 was provided at both recording electrode 14 and reference electrode 16. The differential amplifier 26 cancels the common mode noise presented at both the input and the reference electrode, since the low voltage of extracellular AP is subjected to noise from electronic devices and nearby AC power lines. A high Common Mode Rejection Ratio (CMRR) amplifier may be the differential amplifier 26 in one embodiment. Because recording electrode 14 has a high impedance interface with the tissue due to thin recording electrode 14, the amplifier 26 is selected to have an adequate input impedance to avoid signal attenuation from the voltage divider and impedance mismatch. Further, amplifier 26 has a very low input bias current because APs have weaker currents. A series of operation amplifier circuits (op-amps) are connected as an instrument amplifier to address these observations. To minimize the board space, an integrated instrument amplifier (IA), also referred to as differential amplifier 26, in a single chip may be used that also needs lower supply currents and provides an accurate gain. In one embodiment, an integrated IA has a CMRR of 80 dB, an input impedance of 1-G$\Omega$, and an input bias current of 2 nA (AD620, Analog Device Inc.). The gain of AD620 can be programmed by a resistor $R_G$. A 5.1-k$\Omega$ for $R_G$ is chosen, resulting in a gain of 10.7, in one embodiment of the invention. All parts may be assembled on a printed circuit board (PCB) or integrated on a single integrated circuit (IC) chip.

At the input stage shown in FIG. 3, a high-pass filter 28 with $C_1$ (0.1 µF) and $R_1$ (1M$\Omega$) shown with a 1.6-Hz cut-off frequency is placed at the electrodes to reduce the DC level from the animal that might create artifacts. The 1-M$\Omega$ resistor, $R_1$, also provides a signal path to the ground at an op-amp 30 input. Without a resistor, the current may accumulate and eventually saturate the op-amp 30. Depending on the recording electrodes used, a low resistance value reduces the amplifier input impedance and attenuates the signals while a high resistance value increases the op-amp DC offset and saturates the amplifier. The value of 1M$\Omega$ was achieved by experimental optimization.

After the pre-amp stage, the signal is amplified by a typical amplifier circuit in the gain stage. As shown in FIG. 3, an op-amp 30 is used. In one embodiment, op-amp (TLV2264, Texas Instrument) 30 has a gain-bandwidth product of about 670 kHz. Two stages of non-inverting amplifiers are added with an equal gain of 15. The total gain of the transmitter board is thus 2400. The amplified signal is connected to a high-pass filter 32 ($C_4$, $R_8$) to pull the signals from the 3V virtual ground down to the 0-2.5V level, which is the analog input range of a wireless transmitter module 34 (TX3A, Radiometrix). Because action potentials have both positive and negative cycles, the supply voltages need to be both positive and negative to operate the amplifiers with the virtual ground technique. The virtual ground is made by a voltage divider 36 using two 100-k$\Omega$ resistors, identified as R9 and R10. The half 3-V is connected to an operational amplifier 38, identified as A4, as a buffer to maintain the voltage to serve as the system ground for all amplifiers. Transmitter module 34 operates at 914 MHz, which is an industrial, scientific and medical (ISM) band publicly allowed in the United States but other frequencies are acceptable. One embodiment uses FM modulation and is capable of transmitting the signal with a base band up to 35 kHz within a range of 300 m.

In another illustrative embodiment, sensor 2 communicates directly with stimulator 4, as shown in FIG. 1. While carrier frequencies of 433 MHz and 914 MHz are acceptable, higher operating frequencies and a wider bandwidth may be employed, considering chip sizes, antenna dimensions, band interference, power consumption, and data rates. Ultra-wideband (UWB) communication systems provide a particularly attractive option. UWB operates in the time domain using low-powered short pulses and therefore has many advantages over current narrow-band technologies. UWB signals consist of a series of short (sub-nanosecond) pulses, and data transfer speeds that are between 100 Mbps and 1 Gbps that permit high-throughput data transfer. UWB manufacturing costs are also less since most integrated components are active circuits. Moreover, the UWB circuit is less complex which has a lower power demand over a wide spectrum and, in fact, its power level is well below the noise floor of other existed narrowband RF systems. This enables co-existence of UWB and already existing wireless communication.

Figure 4:
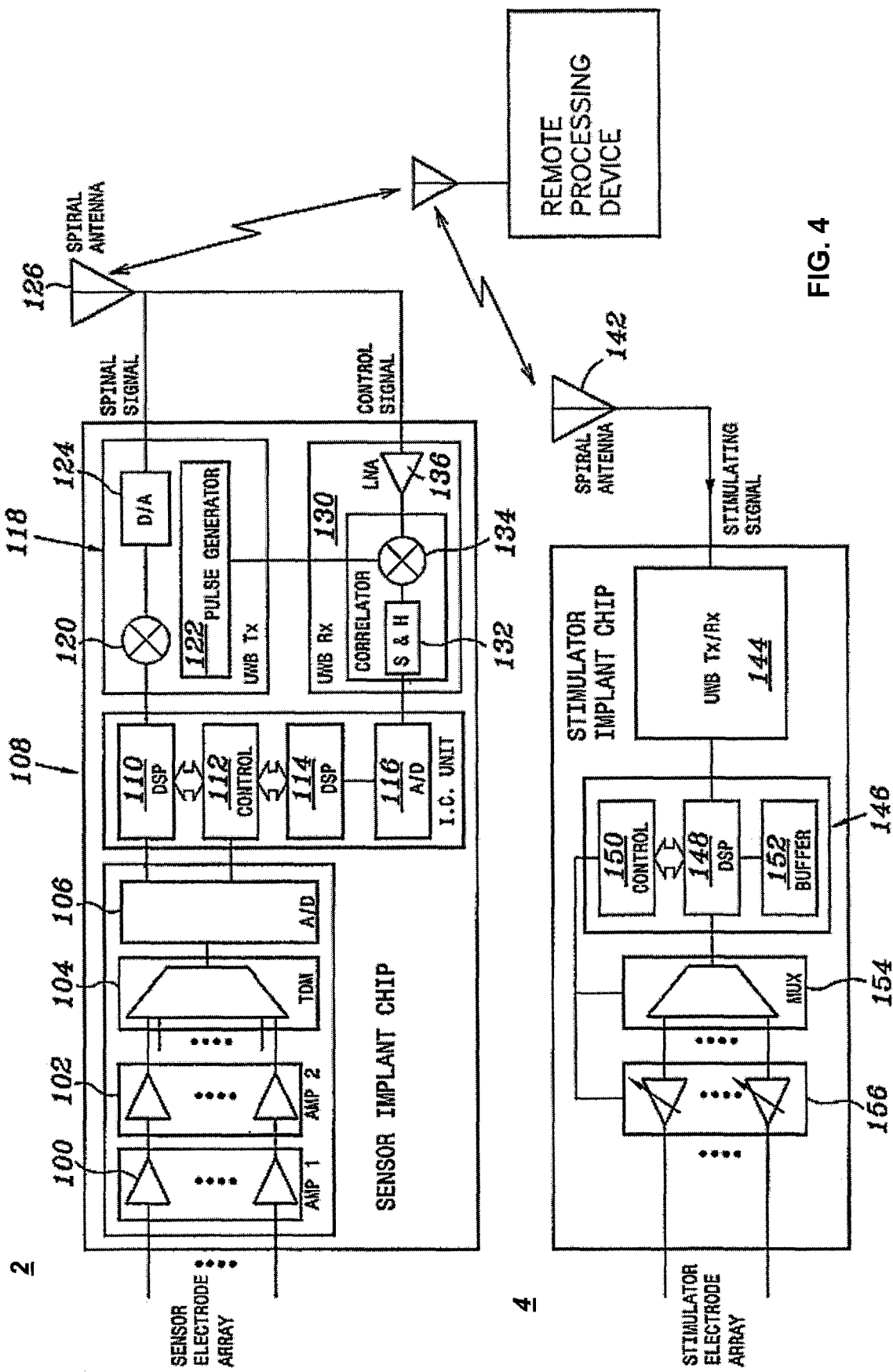
FIG. 4 is a second block diagram of a sensor and a stimulator through wireless communication with a remote processing device in one embodiment.

Referring to FIG. 4, signals received from electrode array 12 are recorded and reference signals are amplified with two-stage amplifier arrays 100 and 102 before they are multiplexed via time-division multiplexer (TDM) 104 and digitized via an analog-to-digital (A/D) converter 106 then passed to integrated circuit unit 108, specifically to digital signal processor (DSP) 110 and control 112. Integrated circuit unit 108 also comprises a second DSP 114 and a second analog-to-digital converter 116. One embodiment of the DSP chip architecture is TMS320C5402-80 (Texas Instruments, Inc.) with relatively low power consumption. The signal passes to a transmitter 118 that includes a modulator 120 and a pulse generator 122 to control of the pulse repetition rate, pulse width, and the high- and low-voltage levels of the pulses then splits and passes to a digital to analog converter 124 prior to transmission of the signal via antenna 126. Within integrated circuit 108, the signal also passes from control 112 to a second DSP 114 to a second analog-to-digital converter (ADC) 128 which is passed to a sensor receiver 130. The second sensor receiver includes a sample and hold detector 132 and a correlator 134, which is in communication with pulse generator 122. The correlator 134 consists of a sample-and-hold circuit, a mixer (not shown), and an integrator (not shown). The combined correlator 134 and pulse generator 122 is used to extract the position information (the transmitted information bits) of received impulses. The amplified received signal is correlated with the reference signal in the correlator block.

Figure 5A:
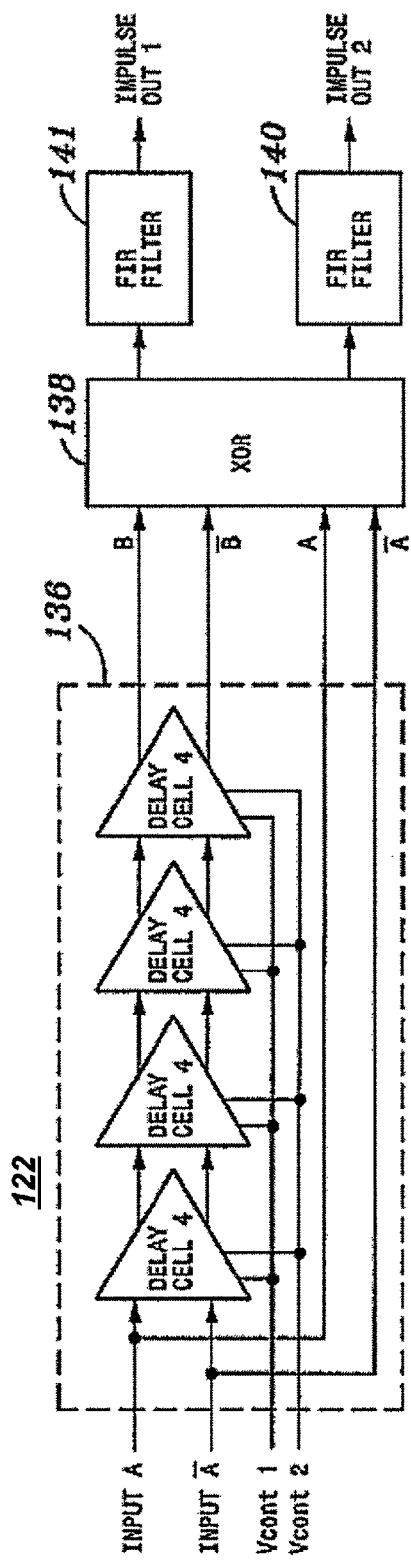
FIG. 5A is a block diagram of an impulse generator for the sensor and stimulator implants.

Referring still to FIG. 4, one embodiment of the pulse generator 122 is an all-digital Complementary metal-oxide-semiconductor (CMOS) UWB pulse generator that yields a pulse of a 5th-derivative Gaussian pulse shape, in one embodiment. Alternatively, over monocycle pulse shapes such as Sholtz's monocycles, Manchester monocyles, or monocycles may be employed, although they would be filtered out to satisfy the Federal Communications Commission (FCC) and UWB regulations. The pulse generator generally comprises a delay line circuit 136 and an XOR cell 138, as shown in FIG. 5A. XOR is exclusive disjunction in logical operation on two logical values, typically the values of two propositions, that produces a value of true only in cases where the truth value of the operands differs. For the delay line circuit 136, the interpolation method is employed with its actual shifting delay output ability and a Gilbert cell is used for the XOR cell. To satisfy the desired UWB features, a differential MOS current mode logic (MCML) was used. MCML circuits with constant bias currents include an accurate high-speed mixed signal application, which dissipates constant static power, requires smaller dynamic power than that of the conventional logic because of the smaller output swings and faster switching. In one embodiment, MCML Circuitry was designed based on the Taiwan Semiconductor Manufacturing Company (TSMC) 0.18 µm (Hsinchu, Taiwan) CMOS technology and modeled with the Advanced Design System (Agilent Technologies, Inc.). To perform a delay line for the transmitting block, the voltage controlled interpolation method was been selected to control the Gaussian pulse width to precisely adjust the targeting center frequency. The Gaussian pulse is generated with 1 GHz pulse repetition frequency. To generate the 5th-derivative, a transversal Finite Impulse Response (FIR) filter 140 and 142 outputs impulse out 1 and 2. The transversal FIR filters 140 and 141 are programmed by adjusting the coefficient weights.

Figure 5C:
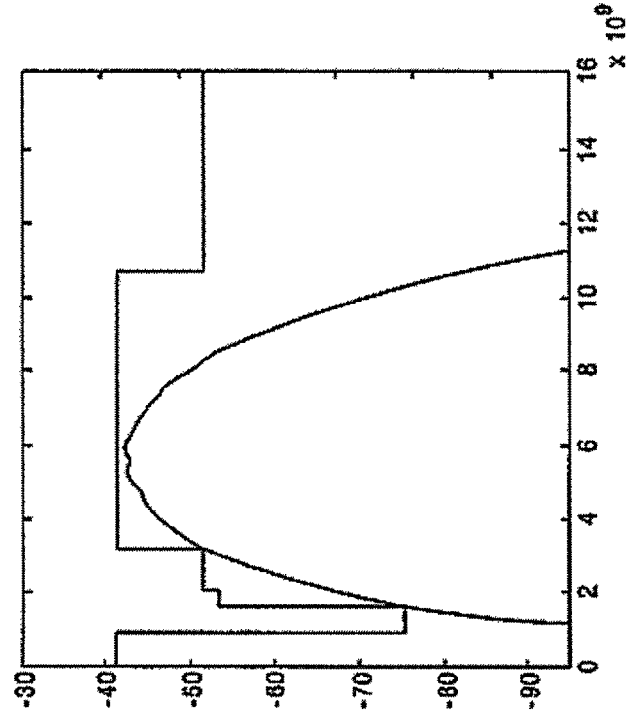
FIG. 5C is a simulation trace of the impulse generator of FIG. 5A.
Figure 5B:
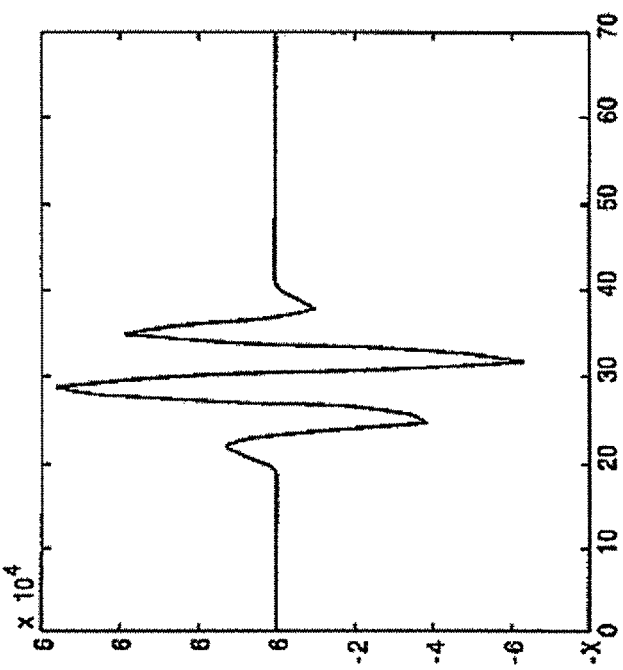
FIG. 5B is a simulation trace of the impulse generator of FIG. 5A.

The simulation results are shown in FIG. 5B and FIG. 5C, indicating that impulse generator 122 produce the 5th derivative of Gaussian pulse to satisfy FCC regulations.

Digital FIR filters have been used for data rates below several hundred Mbps. The speed limitation of ADCs prevents the use of fully-digital FIR filters in higher speed cases. Mixed signal FIR filters with sample-and-hold (S&H) circuit using a rotating switch matrix or coefficient-rotating architecture have been successfully applied to relax the requirements on the S&H in those cases. The performance of such filters is very sensitive to the choices of sampling clock phase. Continuous-time FIR filters without S&H circuits are used in high-speed data transmission, which offers wider tuning range. Thus, a CMOS active continuous-time FIR filter with the tap delay line fully integrated on-chip and adaptive tap coefficients may be employed (not shown). The delay unit for the FIR filter was designed with variable electronic buffers to adjust the frequency (not shown). Finally, the 5th-derivative of Gaussian pulse will be generated by combining the FIR filter and Gaussian pulse generator (not shown). The same Gaussian impulse, used in the transmitter, may be used for the reference pulse.

Figure 6A:
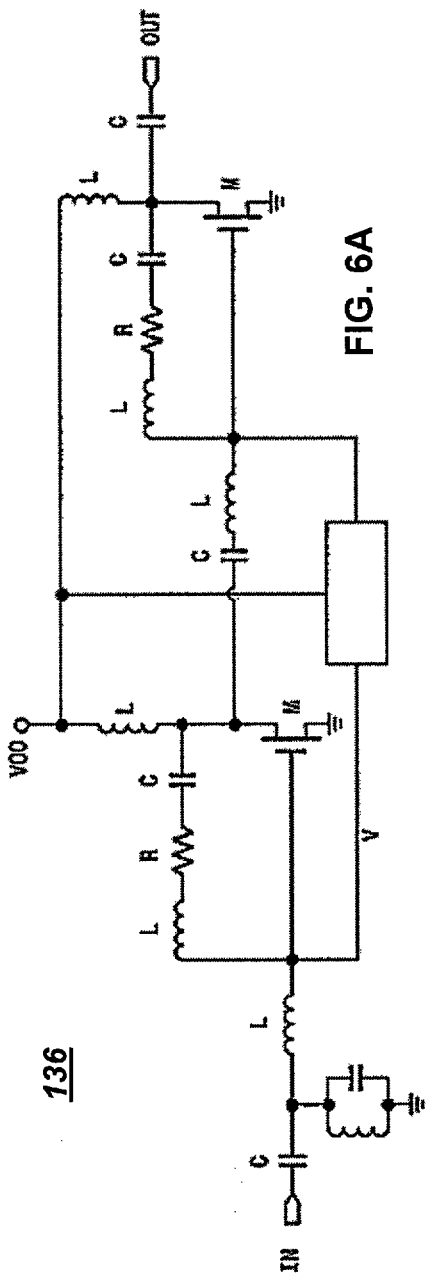
FIG. 6A is a schematic diagram of a low noise amplifier (LNA) circuit shown in FIG. 5A.
Figure 6C:
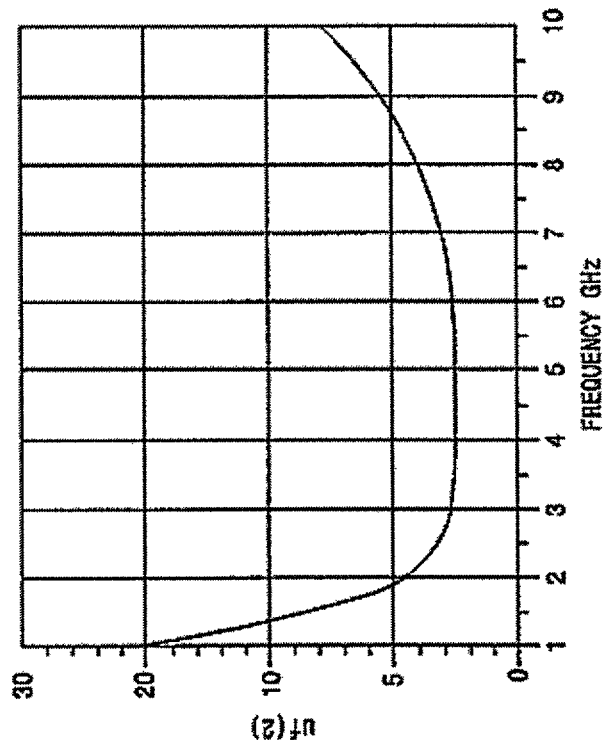
FIG. 6C is a simulation trace of the LNA of FIG. 6A showing noise figures at various operational frequencies.
Figure 6B:
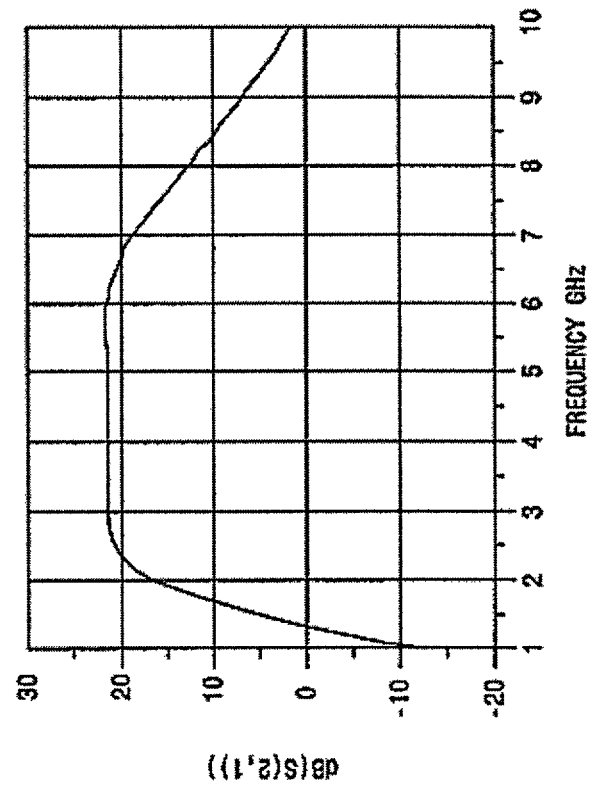
FIG. 6B is a simulation trace of the LNA of FIG. 6A showing gains at various operational frequencies.

As shown in FIG. 4, the sensor receiver 130 comprises the ADC 124, correlator 134, low-noise amplifier (LNA) 136, and coupled to the pulse generator 122. The main tasks of a receiver 130 include timing synchronization to the received signal, recovery of the energy in the received narrow impulses, removal of the pseudorandom coding, and extraction of the time-modulated information. The LNA 136 amplifies the weak signal received from the antenna 126 to the next stage amplifier with a low noise figures (NF). The LNA 136 particularly provides wide bandwidth with low NF suitable for UWB applications and the present design further achieves a flat gain, increased bandwidth and minimized NF. The LNA 136 is based on a shunt-series feedback topology having a resonant circuit for broadband input matching for the CMOS feedback LNA design. One embodiment of the LNA circuit 136 designed with the CMOS 0.18-pm process is shown in FIG. 6A. FIG. 6B shows a gain of 21 dB with gain ripples within 0.39 dB in the frequency range of interest. Since the UWB LNA uses the frequency compensated matching technique for flat gain, there are impedance mismatch losses. The NF of the LNA is 2.7 dB, shown in FIG. 6C, is acceptable. The LNA circuit shown in FIG. 6 provides high gain with flat response over a wide bandwidth and a low NF, as shown. The combined pulse correlator and pulse generator are used to extract the position information (the transmitted information bits) of received impulses. The amplified received signal is correlated with reference signals in the correlator block. The same Gaussian impulse, used in the transmitter, may be used for the reference pulse. The correlator consists of a mixer, an integrator, and an S&H (sample-and-hold) circuit.

After passing through UWB sensor receiver 130, the signal passes to LNA 136. Antenna 126 also passes a control signal to LNA 136 and to correlator 134. The spinal signal may be transmitted wirelessly to a transmitter/receiver of a remote processing device such as a handheld PDA or to an unattached computer. It is contemplated that the user may use the PDA to adjust the stimulation frequency to alter neural activity at the site of the sensor by transmitting a signal to the stimulator or to another remote processing device to modify a signal for transmission to the stimulator. Similar DSP architectures and chip-level UWB transceiver systems based on a combined digital transmitter and analog receiver approach are contemplated. A further benefit of the hybrid telemetry architecture is that it overcomes the shortcomings of so-called "all-digital" transceivers. The digital transmitter can reduce the system complexity and costs since it can be implemented using all-digital circuit blocks. The analog receiver can relax the stringent requirement in the digital receiver such as the high-speed high-resolution ADCs and high power consumptions.

Because of speed limitations observed with ADCs, fully-digital FIR filters may be used in higher speed cases, and mixed signal FIR filters with sample-and-hold (S&H) circuit using a rotating switch matrix or coefficient-rotating architecture may relax the requirements on the S&H circuit in those cases. The performance of such filters is sensitive to the choices of sampling clock phase. To obtain a wider tuning range, continuous-time FIR filters without S&H circuits may be used in high-speed data transmission applications. CMOS active continuous-time FIR filter with the tap delay line fully integrated on-chip and adaptive tap coefficients may also be used. Further, delay circuit 64 for the FIR filter may include variable electronic buffers to adjust the frequency.

Remote Processing Device/Feedback Mechanism

Figure 8A:
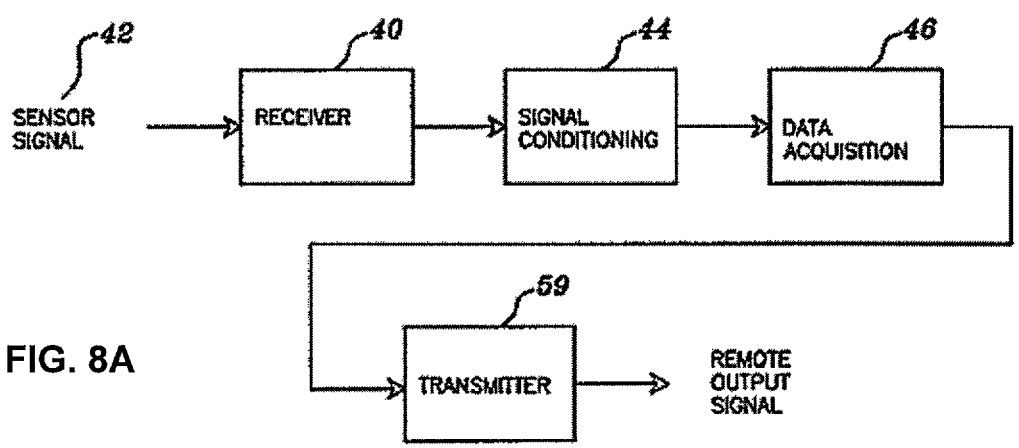
FIG. 8A is a block diagram of a remote processing device in one embodiment.

Transmitter module 34 transmits the FM modulated data via antenna 35, in an illustrative embodiment, to a wireless receiver 40 that is associated with or part of remote processing device 10 (shown in FIG. 1). Alternatively, the transmitter module transmits UWB theme, previously mentioned. FIG. 8A shows illustrative block diagram of the wireless receiver and the subsequent signal processing. Sensor signal 42 is sent to receiver module 40 then is conditioned 44 then is optionally fed to data acquisition unit 46. The received signal includes low frequency fluctuation, mainly at 60 Hz coupling from AC power lines and high-frequency noise. Alternatively, the remote processing device also contains the feedback mechanism software and manual control to automatically/manually adjust the stimulation parameters based on the sensed signals. To activate the wirelessly controlled stimulation with the recorded neuron activities, a data acquisition (DAQ) module (USB-6008, National Instrument) monitors the received wireless signals from the spinal cord. A Labview program was used to estimate the rate of APs (spikes/s) which represented the pain level when mechanical stimuli were applied. The Labview program may operate a feedback loop mechanism 400 to activate the stimulator 2 on the brain when the rate is higher than a specific threshold corresponding to a pain threshold.

Figure 7:
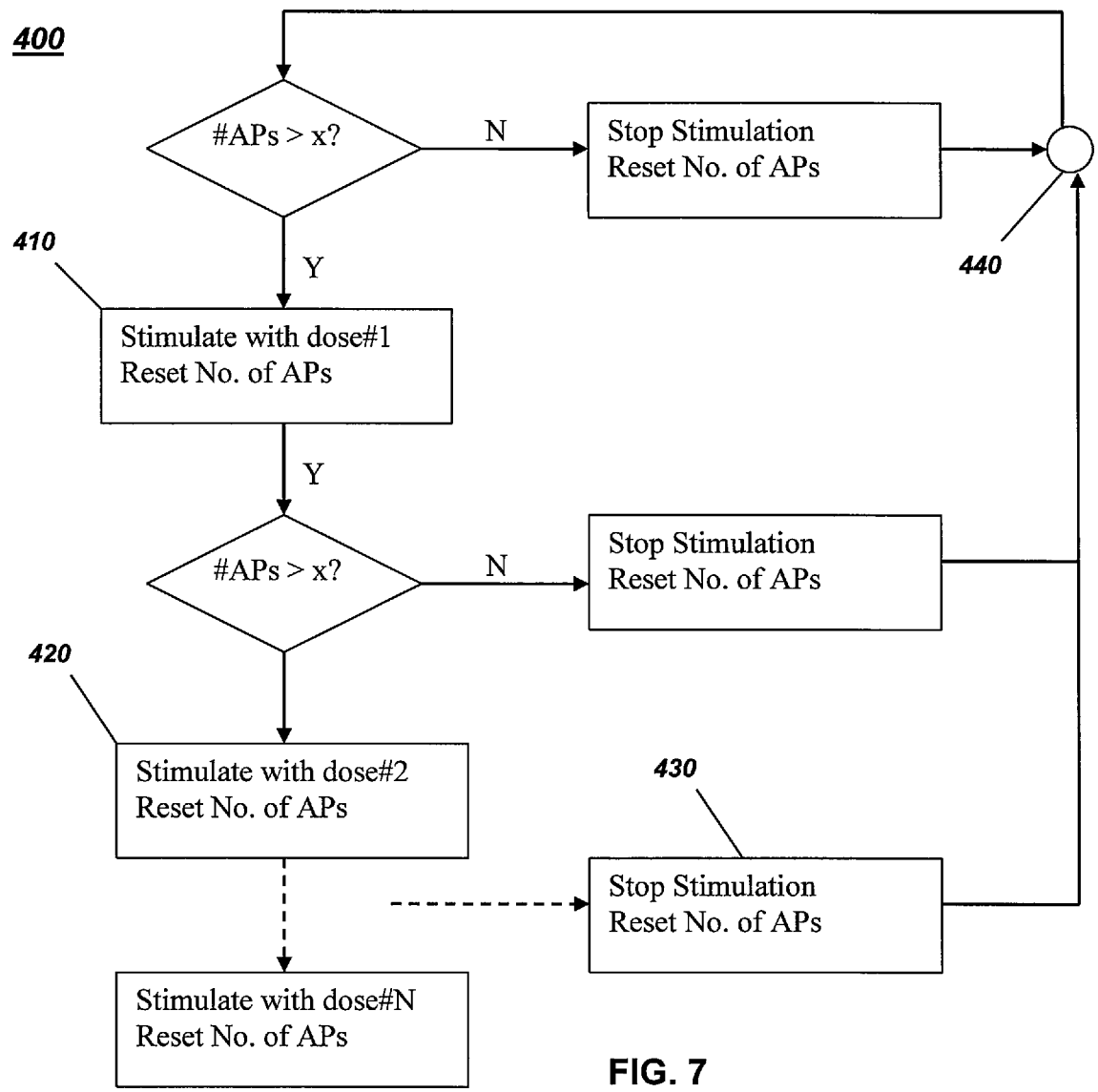
FIG. 7 is a flow diagram of one embodiment of the feedback algorithm.

The feedback loop mechanism 400 may include the same Labview codes for both tasks of calculating AP rates and activation of neurostimulation pulses. Alternatively, commercial software (Spike2, Cambridge Electronic Design) in parallel with a Labview program may verify the accuracy. In one embodiment, the DAQ module has a maximum sampling rate of 10 ksample/s, which is sufficient to monitor the APs since the bandwidth of the pain action potential signal is mostly less than 5 kHz. Knowing that the pulse shapes of action potentials and the pulses have much higher amplitudes than those of background noises, each AP may be counted when the measured signal is higher than a certain threshold voltage. The threshold voltage, sampling rate and number of averaging data points can be adjusted for the feedback. The numbers of APs may be accumulated for a certain period of time called "pain time slot". At the end of the pain time slot, if the number of APs was more than the pain threshold level, the stimulation would be activated. Before the feedback loop is applied, APs during a pressure stimulus from a neuron may be recorded using software. The rate will immediately rise above a certain level, for example 100 spikes/sec at the beginning and gradually decrease to around 50 spikes/sec at the end of the stimulus The simplified operation of the feedback system 400 is illustrated in FIG. 7, in which x is the pain level threshold. The stimulation starts with dose #1 410 (the lowest dose with a low voltage, fewer numbers of pulses, a short duration and a long interval). If the pain level is still higher than the threshold, more intense doses 420 will be given gradually through this feedback mechanism. When the pain is reduced below the threshold 430, the stimulation will be stopped and the loop begins again 440 when the pain comes back. The feedback mechanism is a closed loop system feedback between the sensors and stimulators, i.e., an integrative system consisting of both implantable stimulators and sensors to constantly monitor the pain signal and suppress it when it surpass the tolerance level. Closed loop uses feedback to control states or outputs of the dynamical system. The information path in the close loop system includes the process inputs that have an effect on the process outputs, which is measured with sensors and processed by a controller, where the result (the control signal) is used as input to the process, closing the loop.

More complex algorithms can be applied in the feedback loop using the same hardware. The algorithms can be run by a software operating program run by a doctor on a commercially available PC, laptop computer, and workstation having a CPU running a standard operation system. Ultimately, a doctor can run a series of experiments to evaluate the efficiency of each stimulating parameter associated to the pain levels of individuals. This database can be used in decision making providing not only automatic stimulation but also in an efficient way of pain relief.

Figure 8B:
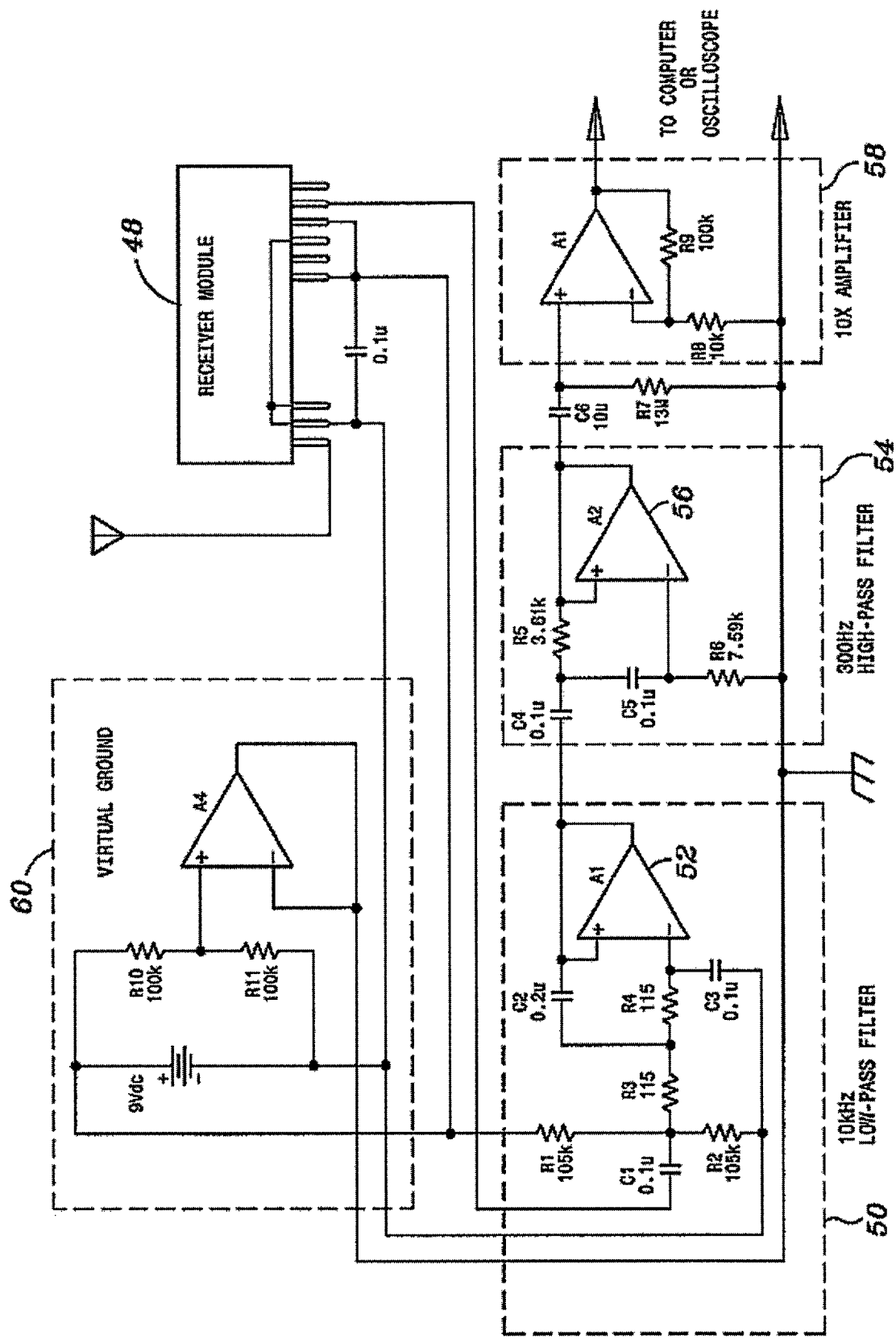
FIG. 8B is a partial circuit diagram of a remote processing device in one embodiment.

A circuit diagram showing an illustrative embodiment of receiver 40 is shown in FIG. 8. The signal is received by receiver module 48 (RX3A, Radiometrix) then carried to low-pass filter 50 to amplifier 52 (A1) then to high-pass filter 54 then to amplifier 56 (A2) before being passed to operational amplifier 58 (A3) before being carried to data acquisition unit 46. Virtual ground 60 similar to that used in the illustrative embodiment described above for the sensor is also applicable in this application. The combination of low-pass filter 50 with high-pass filter 54 forms a band-pass filter of 300 Hz to 10 kHz to eliminate noise and extract the single neuron APs, although the frequency range can be modified as known to one of ordinary skill in the art, for instance, by following a reference filter design to record other types of neuron signal characteristics (e.g., compound action potential at lower frequencies). The signal is amplified ten times using op-amp 58 before fed to data acquisition unit 46 (CED 1401Plus, Cambridge Electronic Design) connected to a computer. The data is analyzed using commercial software (Spike2, Cambridge Electronic Design). After processing, the data is transmitted by a transmitter 59 (not shown) connected to remote processing unite 10 which sends generated digital commands to sensor 2 and stimulator 4. In one embodiment, the transmitter is a part of a transmitter-receiver pair, such as TX2/RX2 (Radiometrix).

Stimulator

Figure 9:
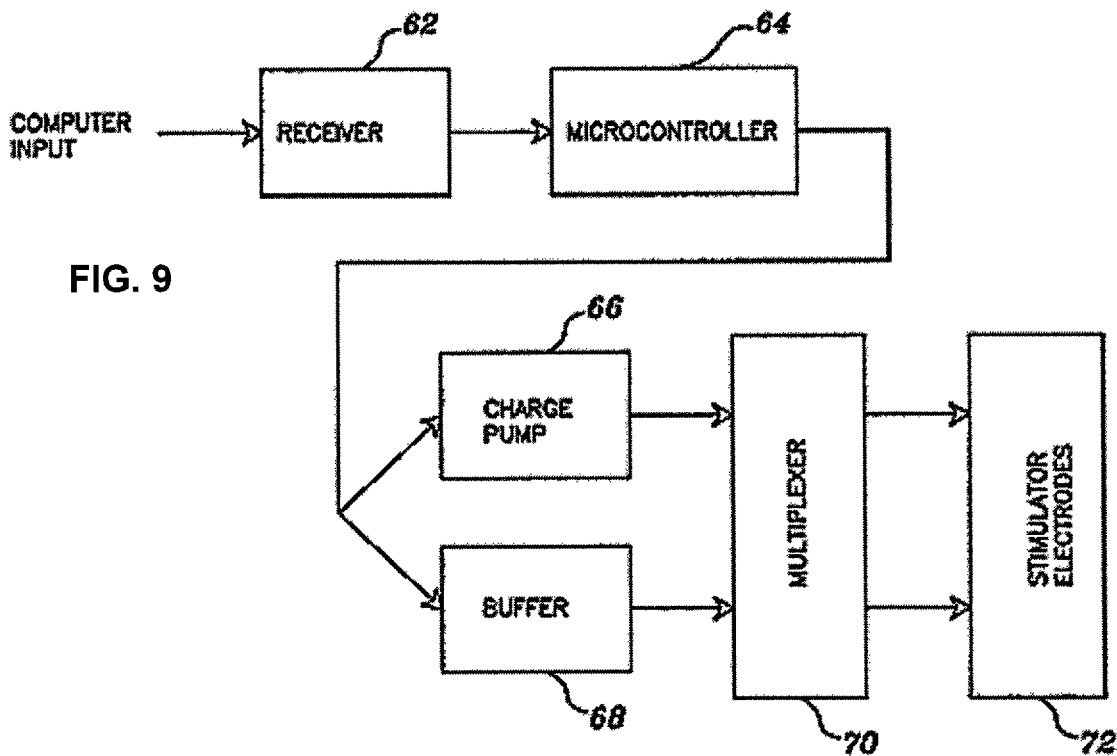
FIG. 9 is a block diagram of a stimulator in one embodiment.
Figure 10:
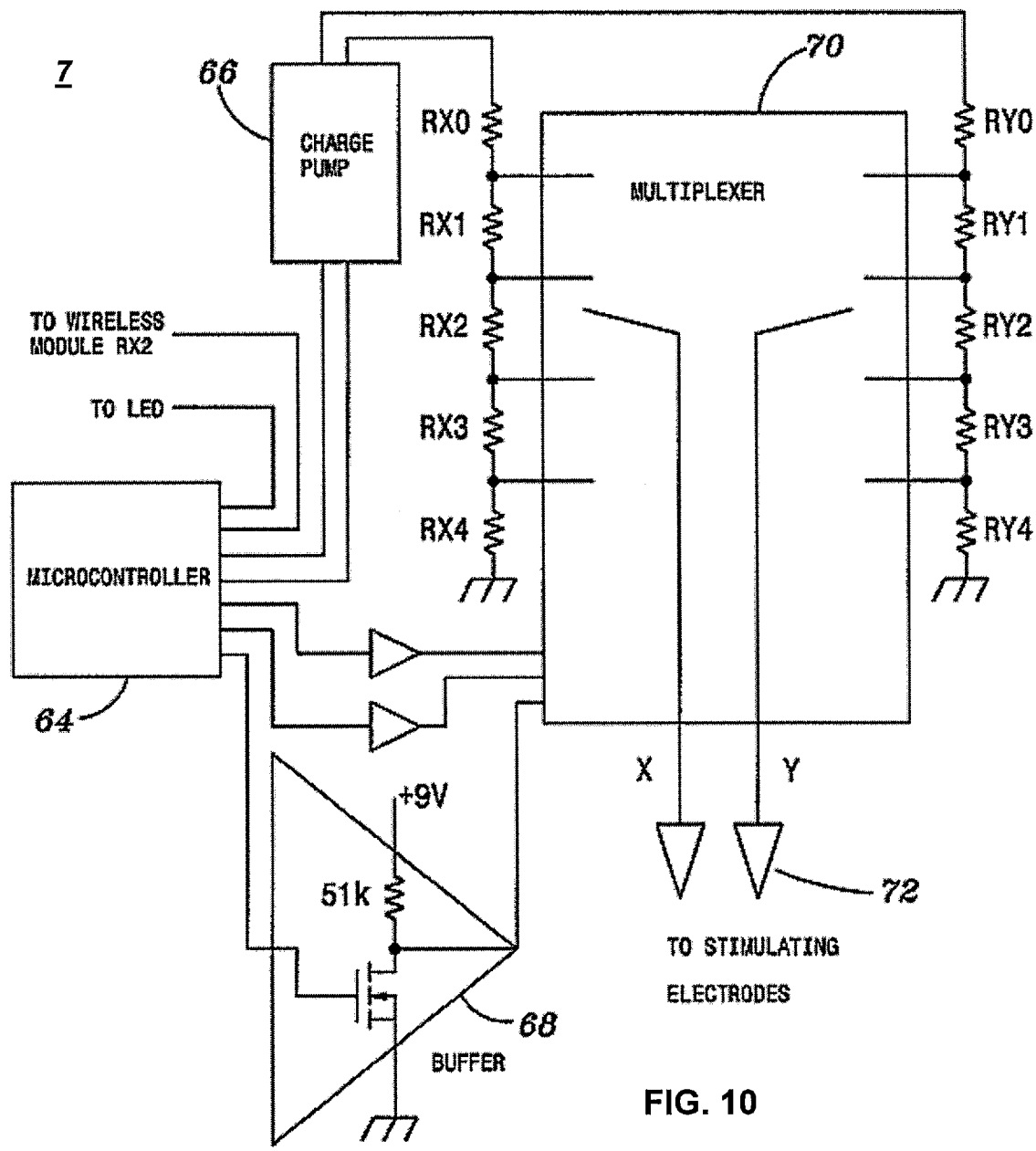
FIG. 10 is a circuit diagram of a stimulator in one embodiment.

FIG. 9 shows an illustrative block diagram of a stimulator 4. The stimulator 4 of an illustrative embodiment has a receiver 62, microcontroller 64, a multiplexer 70 and electrodes or stimulating electrode array 72. Stimulator 4 receives signals by the receiver module 62 and signals sent by transmitter connected to a computer or signals sent by the sensor 2 that feeds the signal to microcontroller 64 that in turn passes the signal to a charge pump 66 and a buffer 68 that in turn feed the multiplexer 70 that passes the signal to stimulating electrodes 72. The receiver module 62 may receive commands from the sensor 2 or synthesized waveforms from the control unit of the computer. The clock and stimulator control block will also be able to generate and activate preset waveforms from the sensor or computer commands. FIG. 10 provides a circuit diagram of an illustrative embodiment of stimulator 4. The receiver RX2 (not shown) on the user receives the commands and feeds to a microcontroller module 64 (BS1-IC, Parallax Inc.) having more than one input/output (110) pin. Microcontroller 64 in the present embodiment was programmed using the PBASIC language provided by the manufacturer but one of skill in the art would be familiar with other languages. PBASIC is a microcontroller based version of Beginner's All-purpose Symbolic Instruction Code (BASIC). After the code is written it is tokenized and loaded into an Electrically Erasable Programmable Read-Only Memory (EEPROM) on the microcontroller, where these tokens are fetched by the microcontroller and used to generate instructions for the processor. One 110 pin is used to receive the command from the wireless module. Another pin is may be connected to an LED to indicate the working status during the stimulation.

This illustrative embodiment utilizes a stimulating system that generates bipolar pulses up to ±18V with adjustable voltage levels. The bipolar pulses are achieved by using a charge pump 66 (MAX202, Texas Instruments) to increase the voltage level, and a multiplexer 70 (CD4502B, Texas Instrument) to switch the voltage level in 4 steps. Alternatively, the stimulator system utilizes unipolar, monopolar, or isopolar stimulating signals that may provide enhanced efficacy using a low current level to reduce power consumption or mitigate collateral effects. The multiplexer 70 is operated by a 5-V supply from microcontroller 64, and the multiplexer 70 is operated by a ±9V supply generated from a charge pump 66. Two of the I/O pins from microcontroller module 64 are used to create 0-5 V stimulating pulses. The pulses are fed to the charge pump 66 resulting in 9V signals. Each signal is fed to series of resistors (identified as RXO-RX4 and RYO-RY4) to tap out four different voltage levels, which can be arbitrarily adjusted by changing the resistance values. The tapped out voltages are sent to multiplexer 70 into the X and Y channels. Three I/O pins of microcontroller module 64 are used to control both switches of multiplexer 70 to connect the outputs X and Y to any of the four tapped voltage levels. In one embodiment, three buffers 74 (FDG6301) translate the 5-V level from microcontroller module 64 to the 9-V level required to control multiplexer 70. The voltage of the bipolar pulses between the outputs X and Y therefore can be selected from 0V to ±18V coupled to the stimulating electrodes 72. The stimulating electrodes 72 may be similar to the sensor electrodes or electrode array, discussed below. The stimulating pulses parameters including voltage levels, numbers of pulses, pulse durations, and pulse intervals are controlled wirelessly from the remote processing device which contains signal processing software such as a Labview program.

In the UWB application, as shown in FIG. 4, the stimulator 4 includes an antenna 142 that receives input signals from sensor 2 or remote processing device 10 and feeds the signal to transceiver 144 (or separate transmitter and receiver) and passes the signal to an integrated circuit 146. The integrated circuit has a DSP 148 in communication with a control 150 and a buffer 152. The signals generated from the control 150 enter the DSP 148 to control the signal processing. The signals from the DSP 148 pass through a multiplexer 154 and then enter a variable amplifier array 156. A portion of the control signals also control the multiplexer 154 and the variable amplifier arrays 156. The control signals manage the multiplexer to selectively pass or block the stimulation signals in the multiplexer. The neurostimulation signals are then selected for the desired neurons. A portion of the control signals also manage the variable amplifiers 156 to control the gains and status of each amplifier. The individual stimulation signals then can be controlled as desired.

Stimulating sites may include a patient's primary somatosensory cortex (SI), secondary somatosensory cortex (SII), anterior cingulate cortex, prefrontal cortex, insular cortex, thalamus, septum, and the sensory area of the thalamus, spinal cord, and peripheral nerves. The invention further allows for treatment in one or more of the thalamus, motor cortex, brain stem, periaqueductal gray, periventricular gray, precentral gyrus, cingulate, caudate, amygdala, parietal cortex, zona incerta, mesencephalic, pontin and medullary retricular formations, superior colliculus, inferior colliculus, nucleus cuneiformis, locus coeruleus, parabrachial nucleus, nucleus ambiguus, nucleus raphe magnus, nucleus reticularis paragigantocellularis, nucleus reticularis gigantocellularis pars alpha (NRGa), raphe pallidus, nucleus tractus solitaris, and spinal trigeminal nucleus spinal cord, and peripheral nerves.

Stimulation sites may be identified in accordance with a variety of techniques, including (1) identification of one or more anatomical landmarks; (2) preoperatively (e.g., using Transcranial Magnetic Stimulation) and/or intraoperatively stimulating one or more brain locations to identify or map particular neural regions that induce or evoke a given type of patient response (for example, a movement or a sensation); (3) estimating a location at which the brain may recruit neurons to carry out a given type of neural activity that was previously performed by a damaged portion of the brain; (4) an electrophysiologic signal measurement and/or analysis procedure (e.g., acquisition and/or analysis of EEG, EMG, MEG, coherence, partial coherence, and/or other signals); and/or (5) a neural imaging procedure.

Multiple stimulators may be placed at various locations in the body. Multiple stimulators may communicate via RFID and may include different stimulating signals. Different stimulators may provide stimulating signals according to particular sensors placed in the body sensing particular APs. The combination of multiple sensors and multiple stimulators coupled with the feedback mechanism may provide optimal pain relief or therapeutic neurological relief. For example, a stimulator placed in the medial septum/diagonal band (MSDB) could have antinociceptive affects in the spinal cord, i.e. activating the MSDB leads to inhibition of nociceptive spinal neuronal response to mechanical pain. Another stimulator could be placed in the PAG for the inhibition of pain neuronal signals, as to provide a double buffer of neuronal stimulation for pain inhibition in the pain signaling pathway. In general, the number and/or location of stimulation sites under consideration may depend upon the nature, number, and/or extent of a patient's neurological condition and/or functional deficits.

Alternatively, as sensory signals are transmitted from periphery to the spinal cord and then up to higher centers, stimulators may be placed at these processing centers or coupling centers for inhibition of pain. For example, the primary afferents to spinal cord dorsal horn neurons, where the information is then relayed to the thalamus, and further up to the primary somatosensory cortex. With this ascending pathway, a noxious stimulus can be perceived as pain; therefore, stimulators and/or sensors may be placed in the spinal cord dorsal horn, thalamus, etc. Also, these ascending signals also activate descending inhibitory systems in the midbrain and medulla, which project to the spinal cord. Together with the large myelinated A-β afferent inputs, they modulate the information processing at the dorsal horn projection neurons to relieve pain. The signals can be categorized as acute pain and chronic pain, where multiple stimulators may treat chronic pain at the afferent inputs and the dorsal horn projections. Additionally, stimulators at the activation of the corticospinal tract can modulate the activity of dorsal horn neurons.

The neuronal system signaling pain may be characterized as a labeled line consisting of neurons in the signaling pathway to the brain (spinothalamic tract, STT) that responds to painful stimuli. Stimulation of certain areas of the nervous system (e.g., motor cortex and periaqueductal gray) to relieve pain is one of the options to those patients with chronic pain conditions. For example, motor cortex simulation (MCS) has been used in patients with neuropathic pain, central post stroke pain, and phantom limb pain and achieved significant effects. Relatively low-frequency stimulation (20-55 Hz) is effective with amplitudes below the threshold for motor responses. On the way from the spinal cord to the brain, signals are also projected to other brain areas, including the PAG. The midbrain PAG is a component of an endogenous pain suppression system; therefore additional stimulators may be placed in the PAG. Focal electrical stimulation has been shown to inhibit nociceptive reflexes and cutaneous and visceral nociception at the spinal level.

Electrode Array

Transcutaneous neuronal signal recording can be accomplished with single or multiple microelectrodes. While traditional metal and glass electrodes are acceptable, silicon thin-film electrodes on micromachined probe tips can be lithographically fabricated and therefore benefit from the advantages of semiconductor batch processes. Surface micromachining is based on the deposition and etching of different structural layers on top of the substrate. Micromachined silicon substrates, with either single or multiple channels, have good recording bandwidths, high sensitivity, low noise levels, high spatial resolutions to identify single neuron, and feasibility to integrate with silicon based ICs. The silicon probes for spinal neural signal recording may be used. The thin silicon substrate is quite flexible. Strong muscle movement (stretching, twisting, etc.) around nervous tissues such as the spine may require the electrode to be reinforced with coatings or other components with higher mechanical strength and resistance to breakage, i.e. plastic, polymers, fluoropolymers, i.e. Teflon™, polytetrafluoroethylene (PTFE), perfluoroalkoxy (PFA), fluorinated ethylene propylene (FEP), and combinations thereof.

Electrode array supporting substrates for sensors and stimulators are robust, deformable, easy to apply in surgery, suitable for mass manufacturing, and flexible. While suitable substrates are generally known to one of ordinary skill, polymer films may be used as the substrate in one embodiment. Many types of polyimide films exhibit stable physical and electrical properties over a wide temperature range, and are chemically stable and biocompatible with dimensional stability. The thin-film polymer-based multichannel intracortical interface may be manufactured with standard planar photolithographic techniques. The use of polymer provides a mechanically flexible surface for high-density electrode arrays.

Figure 11A:
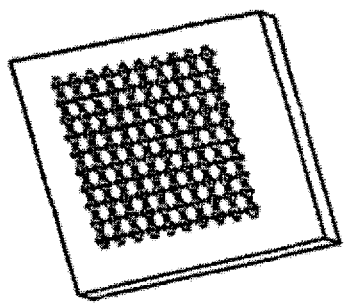
FIG. 11A depicts an example of an electrode array as used with a sensor or stimulator or both.

FIG. 11A shows an illustrative embodiment of the electrode array 12. The electrode array has a very low profile. In one embodiment, the electrode array include dimensions of 125-μm thick 2.5×2.5 cm$^2$ substrate with 1-μm thick metal patterns for a 10×10 electrode array. The fabrication utilizes standard procedures such as spin coating, photolithography, lift-off, wet etch, and plasma dry etch. The polymer substrate is deformable with a tensile strength of 231 Mpa. After thermal annealing of the polymer substrate, no obvious shrinkage or metal pattern is observed. This provides good mechanical characteristics for implants. The dielectric constant is about 3.4 from 1 kHz to 10 MHz and the series resistance is higher than 30 MΩ. This provides a sufficient bandwidth and a good insulator to support the metal electrodes. The recording electrode array can be secured epidurally by suturing to the surrounding tissues and the deformable substrate allows the electrodes to make firm contact to the tissues, as shown in FIG. 11B.

Figure 11B:
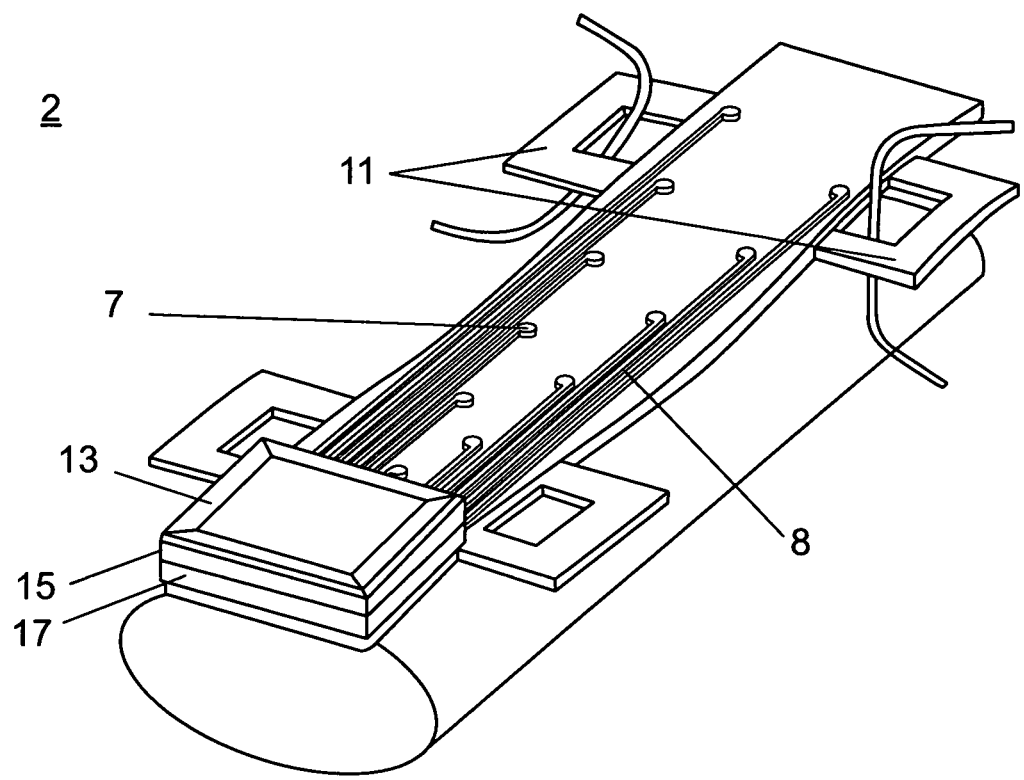
FIG. 11B is a top perspective view of the sensor or stimulator or both electrode array.
Figure 11C:
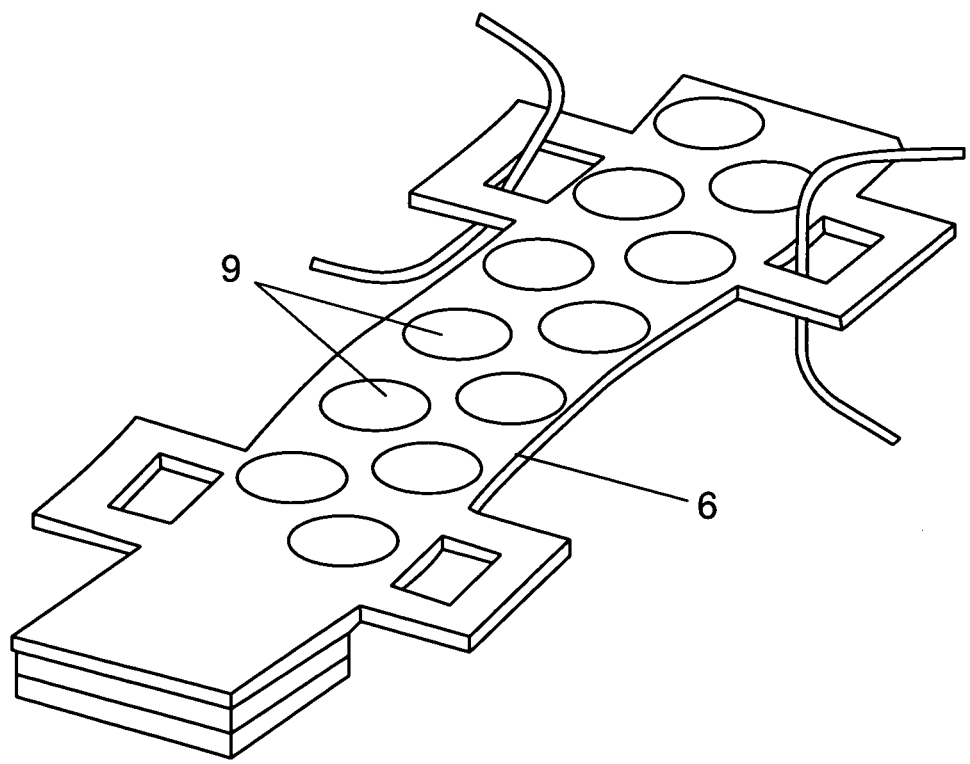
FIG. 11C is a bottom perspective view of the sensor or stimulator or both electrode array.

FIGS. 11B and 11C are the top and bottom sides, respectively, of the sensor 2 and the recording electrodes 14; or the stimulator 4 and stimulator electrodes 27. The sensor 2 and recording electrode 14 or the stimulator 4 and stimulator electrodes 27 will be secured epidurally by sutures 11 to the surrounding tissues. The sensor 2/stimulator 4 includes a flexible substrate 6 allows the electrodes 9/electrodes 27 to make firm contact to the tissues. The sensor includes metal transmission lines 8 on the top surface of the flexible substrate 6. Electrical vias 7 connect the metal transmission lines 8 to metal electrodes 9 for contacting neuron signal recording/stimulating. The implant device also includes a coil antenna 13, a battery 15, and a DSP IC 17.

The metal transmission lines can be fabricated on the top surface of the substrate. A spin-coated layer of polyimide then can be applied to encapsulate the metal lines. A deep reactive ion etching (DRIE) process etches via holes from the bottom surface and the electrical bias can be formed by electroplating. Then metal electrodes are electroplated on the bottom side. The metal electrode shapes and dimensions will be varied to investigate the optimal configuration. Dome shapes received higher action potentials, however, also presented interferences from neighbor cell clusters. After the electrodes are formed, a layer of polyimide can be coated to encapsulate the surface and a short dry RIE etch to expose the metal contact tips. The CMOS IC die can be wafer bonded on the polymer substrate using low temperatures to achieve hermetic closures between the substrates. The metal interconnect bumps make the connections from the CMOS IC to the electrode lines. The rechargeable battery 15 and spiral antenna 13 then can be applied on the backside of the CMOS IC with the metal via connections.

Power Management

In one embodiment, power management for long-term implants includes implementing low power consumption telemetry, CMOS integrated circuits, Li-polymer based rechargeable batteries, and RF energy harvesting to recharge batteries. Lithium polymer batteries evolved from lithium ion batteries, contain lithium salt electrolyte in a solid polymer composite, instead of organic solvent, sandwiched between metal films. The solid polymer electrolyte is not flammable, making it less hazardous, with a high energy density. Polymer cells have a foil-type polymer laminate case, which offers flexibility of shape and sizes. In one embodiment, packaging of miniature Li-polymer batteries is suitable for the sensor implants. A packaged rechargeable Li-polymer battery may include three folds of polymer layers with a total thickness of 1.11 mm and weighs 0.4 g. The packaged rechargeable Li-polymer battery provides a voltage of 3V and a capacity of at least 10 mAh. Alternatively, refining chemistry, vertical electrical interconnects in the integrative platforms and charging mechanism, RF remote charging are included with the lithium polymer battery.

Energy delivery through RF links into implants has been demonstrated by power harvesting through inductive coupling. High frequency signals can be rectified by energy harvesting circuitry to supply DC power for the integrated circuits. Data telemetry and power harvesting can utilize the same antenna, by utilizing the spiral antenna on top of the packaged chips for inductive coupling. A CMOS chip is designed to provide the rectifier, regulator, voltage reference, load regulation and diplex for data/power and timing functionality. The electrical issues, such as impedance matching, filtering, mutual coupling, harmonics, interference and efficiency, need to be analyzed in order to achieve the optimal design parameters. Biological issues in RF power transfer through tissues are also an important issue. The transmitted RF signal powers need to be limited to prevent RF heating of tissues by high signal strength. However, reduced RF signals require longer period of time for recharging and limit usage of continuous stimulation. The designs of both sensor and stimulator circuitry require efficient power consumption.

Antennas and Wave Propagation

For implant or long-term animal study, the telemetry and RF energy-harvesting signals need to go through the tissues, bones and muscle. The UWB telemetry requires a wide bandwidth and the spectral shapes of attenuation for different body parts (human or animal) become important for signal quality. Study of the RF characteristics of living tissues also helps to optimize power management, antenna efficiency and possible human exposure health issues (thermal and non-thermal effects, pulsed fields, shock and burns). For example, at 5 GHz, the brain grey matter, brain white matter, cerebro-spinal fluid, muscle, nerve/spinal cord have conductivity [S/m], relative permittivity, and loss tangent of (0.23, 458.93, 1.78), (0.13, 232.37, 2.03), (2, 108.89, 66.05), (0.59, 308.26, 6.88), and (0.19, 264.77, 2.63), respectively. These parameters may be used to simulate the electromagnetic wave characteristics and RF telemetry performance. One model using the finite difference time-domain (FDTD) simulation shows the radiation patterns change shapes for a miniature spiral antenna of two turns at 5 GHz placed under different biological environments. Optimal antenna designs, expected performance and efficiency are needed with stimulations with sophisticated models of human body.

An RFID system is an automatic identification method, relying on storing and remotely retrieving data using devices called RFID tags or transponders. Electromagnetic coupling in the radio frequency ("RF") portion of the electromagnetic spectrum is used to transmit signals. Conventionally, the RFID system comprises a transmitter and a receiver. The transmitter is otherwise known as a RFID tag and the receiver is known as a reader. The transmitter includes either a passive RFID transmitter tag or an active RFID transmitter tag. The passive RFID tag does not contain a battery and the power is supplied by the reader. When radio waves from the reader are encountered by a passive RFID tag, the antenna within the passive RFID tag receives electromagnetic fields. The passive RFID tag harvests the radio frequency powers from the electromagnetic fields by converting the AC signals to DC currents, which energizes the circuits in the passive RFID tag. The passive RFID tag then sends the information encoded in the passive RFID tag's memory. The sent signals are acquired by the same reader antenna and the tag identification codes are recognized by the reader software.

The RFID mechanism is incorporated in the integrated sensor and stimulator system. Unlike the conventional RFID system, in which only the identification codes are transmitted for remote identification purpose, the system incorporates the identification mechanism into the sensor and stimulator implants to activate the desired sensor or stimulator. In one's body, it might require multiple sensors in various parts of the body to record pain signals and multiple stimulators in various parts of the body to inhibit pains. The remote processing device requires an efficient way to recognize and activate the desire implants. Each implant contains a unique ID code, which is a series of binary codes, in the memory. All wireless implant devices in the body network coordinated by the remote processing device 242 (wearable by the body externally) to form a communication network. Since the ID codes are unique, the communication between the remote processing device and the implant will not interfere with each other.

To minimize reader collision for the RFID mechanism in a passive RFID system Colorwave algorithm, HiQ algorithm, Pulse Protocol Algorithm, Frequency Division Multiple Access ("FDMA'), Time Division Multiple Access ("TDMA"), Code Division Multiple Access ("CDMA") and Carrier Sense Multiple Access/Collision Avoidance ("CSMA/CA") methods can be employed. Colorwave algorithm is a representative of algorithms that use a distributed system with a distributed algorithm, such that a reader network with each reader node has the smallest possible number of adjacent nodes to avoid collision. HiQ algorithm or Hierarchical Q-Learning minimize reader collisions by learning the collision patterns of the readers and by effectively assigning frequencies over time to ensure neighboring readers do not experience collisions from one another. In a Pulse Protocal Algorithm, a reader listens on the control channel for any beacon for $T_{min}$ time before communicating, and if no beacon on the control channel for $T_{min}$, starts communication on the data channel. FDMA access technology to share the radio spectrum amongst multiple users by allocating multiple users with different carrier frequencies of the radio spectrum. TDMA a channel access method for shared radio networks to allow several tags to share the same frequency channel by dividing the signal into different timeslots. CDMA is a method of multiplexing that divides up a radio channel by using different pseudo-random code sequences for each tag. CSMA/CA dictates a tag wishing to transmit has to first listen to the channel for a predetermined amount of time so as to check for any activity on the channel.

Although an active RFID system includes only one receiver, receiver/reader collision issues exist among active RFID transmitters when they are trying to send signals to the base station simultaneously. Anti-collision methods for passive RFID systems can be implemented for the active RFID system. In one embodiment of the invention, for a full active RFID monitoring system, TDMA can partition alarm transmission and recording periods efficiently if the data burst rate is sufficiently high. In another embodiment of the invention, for a simple active RFID monitoring system, the transmitter tag sends out the alarm signal along with the ID signal only when the sensor outputs give improper data values. Normally, the transmitter tag will be in a sleeping mode to save energy. CSMA/CA overcomes reader collision when two different transmitter tags transmit at the same time. Each transmitter tag includes listening functionality that can be used for the Listen Before Talk ("LBT") and the Delay Before Talk ("DBT") mechanisms. LBT dictates that a reader must listen and confirm that a particular channel is not occupied before it can use that particular channel to interrogate any transmitter tag. DBT dictates that a reader will be delayed before talking to the reader if a particular channel is occupied.

Device Performance

Figure 12D:
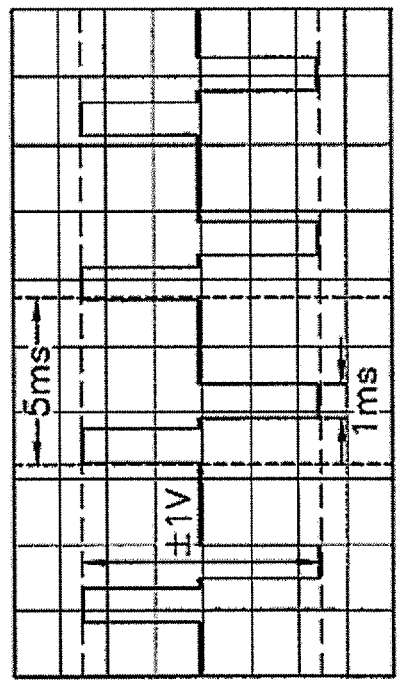
FIG. 12D shows bipolar pulses generated by the remote processing device of FIG. 12A with a ±1 V amplitude, a 1-ms duration and 5-ms intervals (or 200 Hz) generated from the device of FIG. 12A showing the efficacy of the wireless system of one embodiment.
Figure 12B:
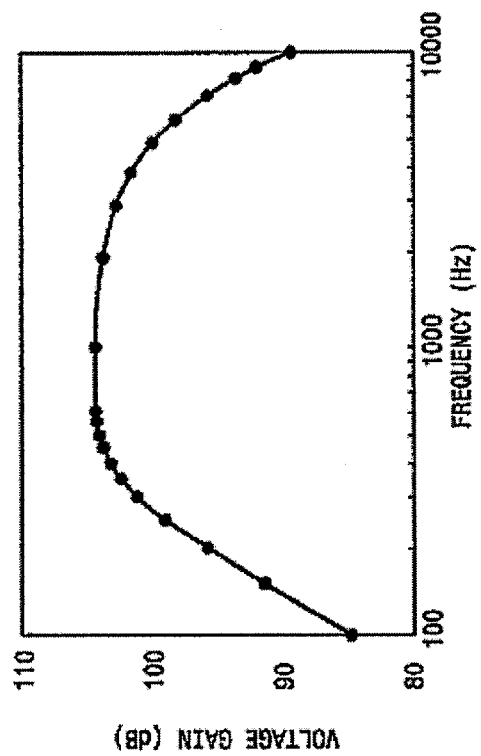
FIG. 12B shows the frequency response of the input signals of FIG. 12A.
Figure 12A:
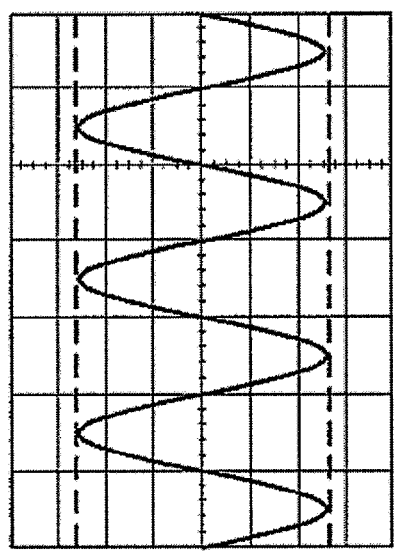
FIG. 12A depicts output signals from a remote processing device as disclosed herein tested using synthesized sinusoidal waveforms as input.
Figure 12C:
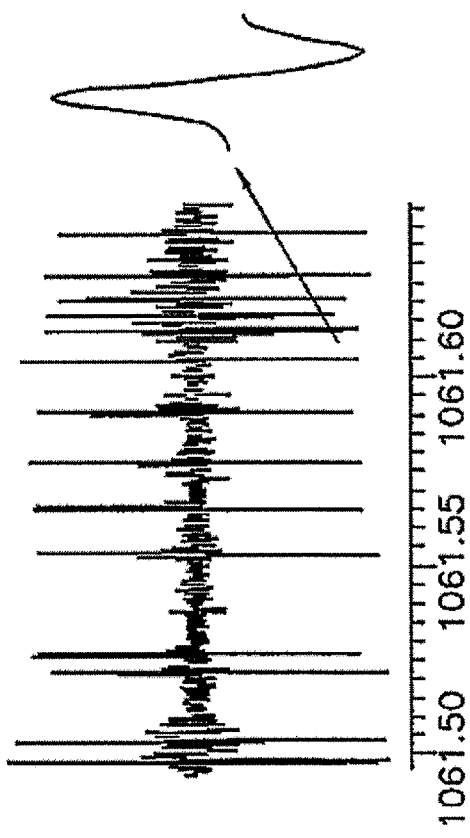
FIG. 12C shows typical recorded action potentials (APs) with a single action potential waveform expanded as indicated by the arrow.

The device was first tested using synthesized sinusoidal waveforms as input. As shown in FIG. 12A are the output signals transmitted by the remote processing device 10. At 1 kHz, the 500 μVp-p signals were recorded with clear shapes, shown in FIG. 12A without visible distortion. Referring to FIG. 12B, the frequency response was measured from 100 Hz to 10 kHz with the 500 μVp-p input signals and the system gain at 1 kHz was 15,000 or 84 dB. The 3-dB bandwidth of the systems spanned from 300 Hz to 4 kHz. The high frequency roll-off shifted from the original design at 10 kHz. The change might be due to the reduction in the gain bandwidth product of the op-amp when the gain is high. FIG. 12C shows typical recorded APs with a single action potential waveform expanded as indicated by the arrow. Four of bipolar pulses with a ±1V amplitude, a 1-ms duration and 5-ms intervals (or 200 Hz) were generated from the device and recorded by an oscilloscope, shown in FIG. 12D.

EXAMPLES

The following examples are put forth so as to provide those of ordinary skill in the art with a complete disclosure and description of how the processes, apparatuses, systems, and/or methods claimed herein are made and evaluated, and are intended to be purely exemplary and are not intended to limit the scope of processes, apparatuses, systems, and/or methods. Animal/human bodies are not a deterministic system. The responses (recorded action potentials) toward stimulation are time-dependent, location-dependent, probed-neuron dependent and complicated with individual's nervous system. The examples show typical responses indicating trends toward specific stimulation parameters. Efforts have been made to ensure accuracy with respect to numbers (e.g., amounts, signals, etc.), but some deviations should be accounted for.

Animal Preparation

Male Sprague-Dawley rats (300-350 g) 60-90 days old were used in the experiments. All surgical procedures are approved by the University of Texas at Arlington Institutional Animal Care and Use Committee. The procedures are in accordance with the guidelines published by the Committee for Research and Ethical Issues of the International Association for Study of Pain (Zimmermann, 1983). Animals were anesthetized using sodium pentobarbital (50 mg/kg, i.p.). The spinal cord was exposed by performing a 3-4 cm laminectomy over the lumbosacral enlargement. A cannula was inserted in the trachea for artificial respiration if necessary. The anesthesia was maintained by intravenous administration of sodium pentobarbital at a rate of 5 mg/ml per hour. The pupillary reflex was monitored periodically to ensure a proper depth of anesthesia. The spinal cord was immobilized in a stereotaxic frame and covered with mineral oil. The end tidal $CO_2$ was maintained at around 30 mmHg and the body temperature was maintained at 37° C. using a feedback controlled heating pad and a rectal thermal sensor probe.

A tungsten microelectrode (10-12 MR, FHC) was used for electrophysiological recordings in the L5 and L6 regions of the spinal cord dorsal horn. The electrode was connected to the amplifiers on the wireless device. Single unit extracellular recordings were performed in dorsal horn neurons, which were searched by mechanical stimulation of the receptive fields in the plantar region of the hind paw. The transmitted data were recorded using the CED 1401Plus and Spike2 software to extract the action potential signals.

Graded mechanical (brush, pressure, and pinch) stimulations were applied to the receptive fields in the hind paw to simulate pains. Brush was applied by a camel hair brush moving over the receptive fields in a rhythmic fashion which was innocuous. Pressure was applied by a venous bulldog clamp (6 cm long, straight, serrated jaws) which was between innocuous and noxious. Pinch was applied by an arterial bulldog clamp (3 cm long, straight, serrated jaws) as a noxious stimulus. To analyze the pain level quantitatively, the applied force (F) as a function of displacement (x) of the clamp was measured. FIG. 13 shows the measured results. The graph follows the Hooke's Law (F=kx), where the slope k is the spring constant of the clamp. The slopes are 31.17 N/m for the pressure and 573 N/m for the pinch stimuli. As the clamp pressed onto the rat's feet within a 25-mm$^2$ area (A), and the clamp opened by 3 mm, the mechanical pressures are 0.54 psi for the pressure stimulus and 9.35 psi for the pinch stimulus, respectively, calculated by P=F/A=kx/A, where F is the restoring force exerted by the material (usually in Newton's), k is the force constant (or spring constant), x is the distance that the spring has been stretched or compressed away from the equilibrium position, which is the position where the spring would naturally come to rest (usually in meters), and A is the area. Each mechanical stimulus was applied once for 10s with an inter-stimulus interval of 20s. The pain response to each mechanical stimulus was measured as the number of action potentials per second. Wide dynamic range (WDR) spinal dorsal horn neurons were selected.

Example 1

After craniotomy, a bipolar stimulating electrode (Science Products) was placed in motor cortex, 0.2 mm rostral to bregma, 2.0 mm lateral to the midline, and a depth of 1 mm. The electrode was connected to the wireless device for bipolar stimulation. An electrode was inserted in the spinal cord to record lumbar spinal cord dorsal horn neuron activities. Both the sensor and stimulator wireless communicate with the remote processing device in which a software program based in the Labview program recorded the received action potentials and was manually controlled to activate the wireless neuro-stimulator with preset stimulating parameters and precise timing. The sensor and stimulator forms a feedback closed loop. The stimulation started manually when pain signals at the spinal cord were identified and recorded at the computer in this experiment. 80 pulses were given to the rat during periods of the mechanical stimulation. Each stimulation lasts for approximately 0.1 millisecond. Various stimulating parameters including voltage levels, numbers of pulses, pulse durations, and pulse intervals were used to observe the inhibitory effects of the wireless stimulation.

Figure 15A:
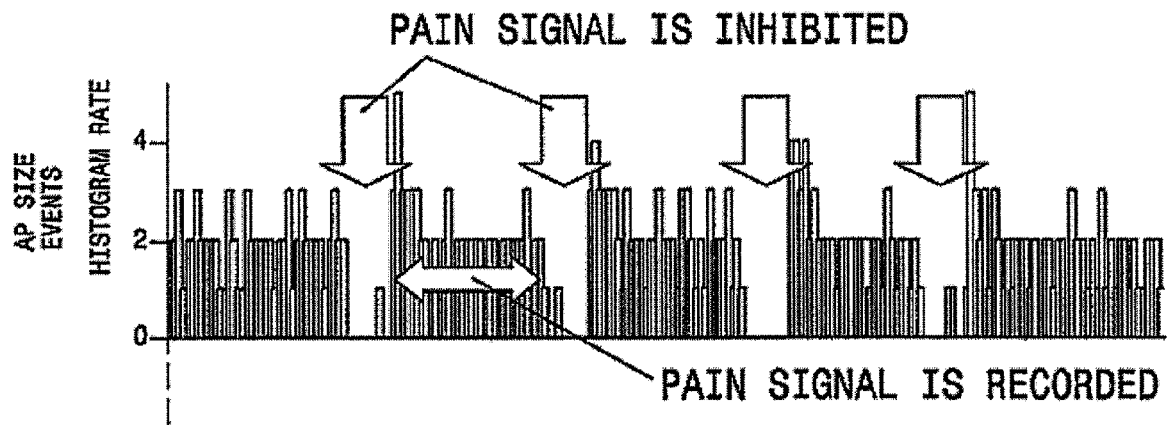
FIG. 15A is a rate histogram showing the number of action potential (APs) spikes per second of spinal cord neuron recorded by a sensor disclosed herein after motor cortex stimulation.
Figure 15B:
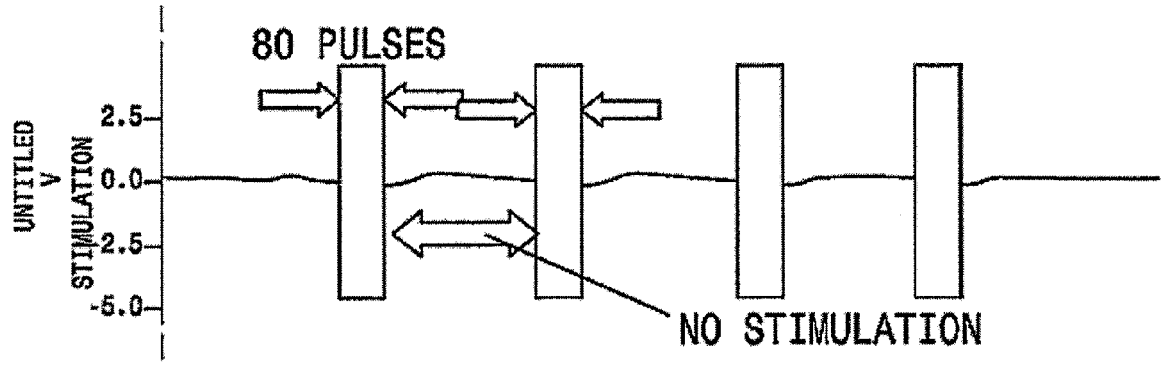
FIG. 15B indicates the periods of motor cortex stimulation in which a series of stimulating pulses are applied.
Figure 15C:
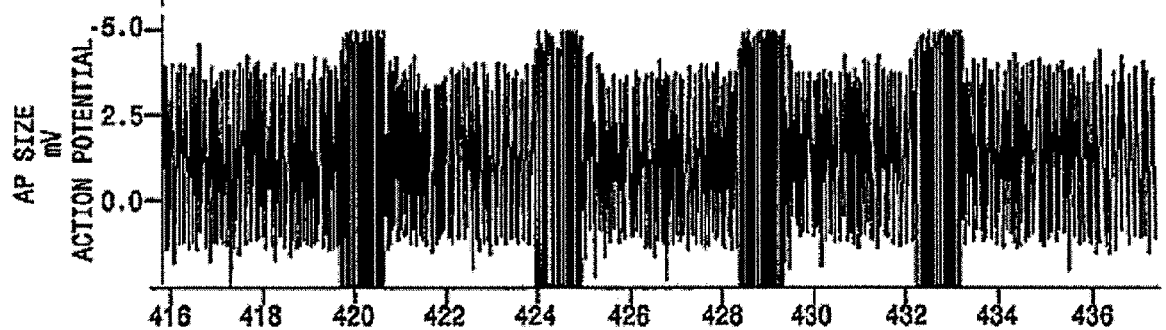
FIG. 15C is the recording trace of the spinal cord lumbar dorsal root neuronal activity spikes shown graphically in FIG. 15A and shows that spinal cord neuron activity is reduced during cortical stimulation reflected in FIG. 15B.

The single neuron recording during the pressure stimuli on the rat's paw with wireless stimulation in the motor cortical area is shown in FIGS. 14A-14C and 15A-15C. FIG. 14A shows a trace recorded in the lumbar spinal cord dorsal horn neuron with an electrode and FIG. 14B shows the filtered signal processed by a sensor as discussed herein. FIG. 14C (inset) is a trace of a single signal at higher resolution showing that it is a distinct signal and recognizable by the Labview-based software discussed above as a distinct waveform. FIG. 15 shows the results of the motor cortex stimulation (MCS) to inhibit the spontaneous activity of a spinal cord dorsal horn neuron. The trace shown in FIG. 15A is the rate histogram (spike/s) of the corresponding spikes of the spinal cord neuron signals (shown in FIG. 15C). Each vertical line in FIG. 15C represents one spike and the rate histogram indicates the presence of pain. In the trace shown in FIG. 15B, each period (shown in bars in the figure) indicates motor cortex stimulation of 80 pulses. The data shown in FIG. 15A, noted by the open arrows, reveals clearly decreased single-neuron activity in the dorsal horn that indicates the inhibitory effect of MCS against pain. Stimulation of the motor cortex during noxious stimulation to the footpad reduces spontaneous dorsal horn sensory neuronal activity correlated with pain.

The rate of APs is two to three spike/s (at 416 s-420 s) and the rate reduced to almost zero spikes/s when the first stimulating pulses were applied (at 421 s-422 s) corresponding to almost 100% inhibition. After the stimulation ended, the rate of APs rose back to two to three spike/s (at about 422 s). When the second stimulating pulses were applied, the rate of APs decreased, and the cycles continued with the third and fourth stimulation. The arrows indicate the clear inhibition effect compared with no stimulation periods.

Example 2

After craniotomy, a bipolar stimulating electrode (Science Products) was placed in motor cortex, 0.2 mm rostral to bregma, 2.0 mm lateral to the midline and a depth of 1 mm. The electrode was connected to the wireless device for bipolar stimulation. The recording electrode was placed in the spinal cord to record action potentials from a spinal dorsal horn neuron. The Labview-based program was manually controlled to activate the wireless neurostimulator when the pain signal was identified and recorded wireless in the computer. FIGS. 16A-16B show the results of two stimulations, the first with 20 pulses at ±2.5 V and 200 Hz and lasting 1 millisecond and 5 millisecond intervals ("Stimulation 1"), and the second ("Stimulation 2") differing from the Stimulation 1 by a pulse duration of 2 milliseconds.

The single neuron recording during the pressure stimuli on the rat's paw with wireless stimulation in the motor cortical area described above. FIGS. 16A-16B show the results of the motor cortex stimulation (MCS) to inhibit the spontaneous activity of a spinal cord dorsal horn neuron. FIG. 16A is a trace that shows the rate of action potential (AP) (spike/s) of the corresponding spinal cord neuron signals (shown in FIG. 16B) where the mechanical stimuli of brush, pressure and pinch are applied periodically. The pain stimuli are applied in a 10s period, with a 20s recovery period. The first experiment is a control one (shown the first group at the left in FIG. 16A and NONE in FIG. 16C) in which no stimulation is applied. Then various stimulation parameters are applied to the stimulation while all three pain stimuli are applied periodically as mentioned above. The stimulation parameters in each stimulation set used are: (Set number, pulse numbers, pulse duration, pulse intervals)=(#1, 20, 1 ms, 5 ms), (#2, 20, 2 ms, 5 ms), (#3, 50, 0.1 ms, 5 ms), (#4, 100, 0.1 ms, 5 ms), (#5, 100, 0.05 ms, 5 ms), (#6, 200, 0.1 ms, 5 ms), (#7, 20, 0.1 ms, 5 ms), (#8, 20, 0.05 ms, 5 ms). FIG. 16A shows the pain signals are reduced during Stimulation 1 and Stimulation 2 periods for both pressure and pinch pain stimuli. The AP rates are clearly reduced. The plots in FIG. 16C compare the average rates of AP from different pulse stimulation parameters in the pinch periods. When noxious stimuli (pinch) was applied to the footpad, the AP rate was 73 spike/sec. Electrical Stimulation set 1 and 2 reduce the AP rates to 40 and 36 spike/sec, respectively. All eight stimulation parameters show similar pain inhibition effects with varied percentages of pain reduction. Stimulation of the motor cortex during noxious stimulation to the footpad reduces spontaneous dorsal horn sensory neuronal activity correlated with pain.

Example 3

After craniotomy, a bipolar stimulating electrode (Science Products) was placed in periaqueductal gray (PAG), 7.04 mm caudal to bregma, 0.5 mm lateral to the midline and a depth of 4.2 mm. Another stimulating electrode was placed in anterior cingulated cortex (ACC), 0.26 mm caudal to bregma, 0.5 mm lateral to the midline and a depth of 0.5 mm. The electrodes were connected to the wireless device for bipolar stimulation (one electrode at a time). Recording electrodes were placed in the spinal cord to record action potentials from a spinal dorsal horn neuron. The Labview-based program was manually controlled to activate the wireless neuro-stimulator when the pain signals were identified and recorded wirelessly in the computer. Series of pulses were given to the rat 4 times during the 10-second periods of the mechanical stimuli of brush, pressure and pinch. Each stimulation lasts for 1 second. Various stimulating parameters including voltage levels, numbers of pulses, pulse durations, and pulse intervals were used to observe the inhibitory effects of the wireless stimulation at both PAG and ACC areas. A series of 200±6-Vpp pulses were applied in the 10 second period, with a pulse length of 0.1 ms and an interval of 5 ms to give the lowest averaged AP rates among seven tested sets for both pinch and pressure stimuli. Compared to those in the control period, the averaged AP rates decreases 72% for pressure and 56% for pinch stimuli, respectively.

Example 4

After craniotomy, a bipolar stimulating electrode (Science Products) was placed in periaqueductal gray (PAG), 7.04 mm caudal to bregma, 0.5 mm lateral to the midline and a depth of 4.2 mm. Another electrode was placed in anterior cingulated cortex (ACC), 0.26 mm caudal to bregma, 0.5 mm lateral to the midline and at a depth of 0.5 mm. The electrodes were connected to the wireless device for bipolar stimulation (one electrode at a time). Recording electrodes were placed in spinal cord to record action potentials from a spinal dorsal horn neuron. The Labview-based program was manually controlled to activate the wireless neurostimulator when the pain signals were identified and recorded wirelessly in the computer.

Inhibition of spinal cord dorsal horn neurons has been demonstrated by stimulating midbrain PAG, as well as ACC using conventional wired systems. Similar experiments are conducted using the wireless system. Different from the Experiment 3, the stimulation parameters are independently varied in this experiment. The single neuron recording, during the pressure stimuli on the rat's paw, with wireless stimulation in the PAG and ACC areas are shown in FIGS. 17A-17C and FIGS. 18A-18C, respectively. The stimulation parameters found are 100 pulses, ±1.0V, 100 Hz and 0.5-ms duration for PAG stimulation and 50 pulses, ±16V, 50 Hz and 0.5-ms duration for ACC stimulation.

Figure 17A:
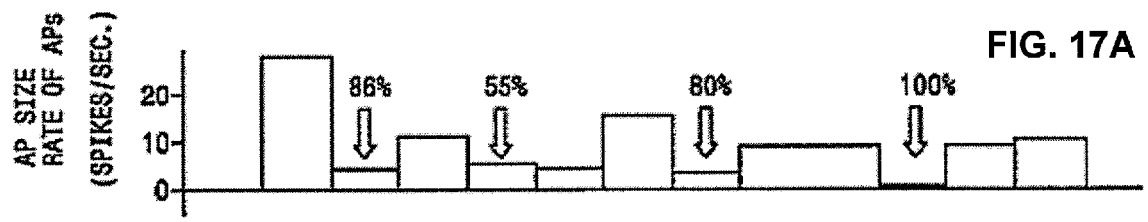
FIG. 17A is a rate histogram of APs (spikes/second) from the trace in FIG. 17C before and after the periods of PAG stimulation shown in FIG. 17B.
Figure 17B:
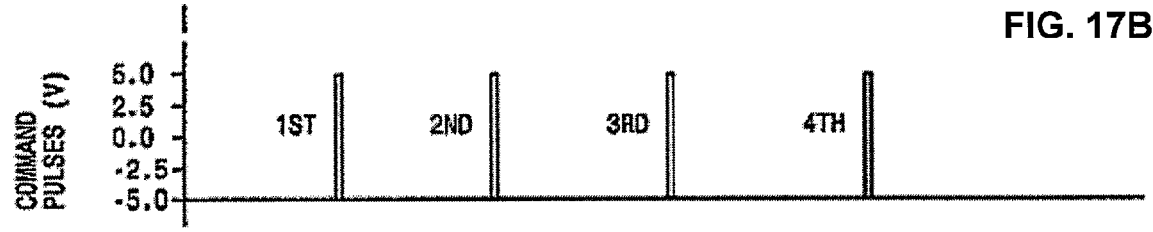
FIG. 17B indicates periods of PAG stimulation with 100 pulses, ±1.0V, 100 Hz for 0.5-ms.
Figure 17C:
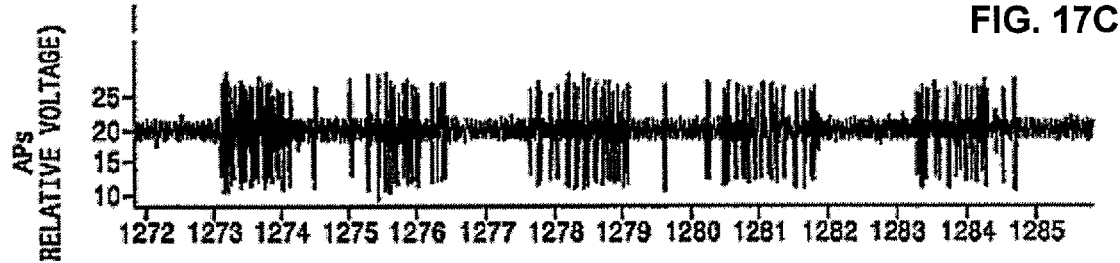
FIG. 17C is a trace of AP signals recorded from dorsal root neurons during periods of PAG stimulation shown in FIG. 17B.

Stimulation of the PAG area is shown in FIGS. 17A-17C. As shown in FIG. 17C, when pressure was applied, the rate of APs increased to 28 spike/s (at 1273 s-1274 s). The rate of APs reduced to 4 spike/s when the first stimulating command pulses, shown in FIG. 17B, were applied (at 1274 s-1275 s) corresponding to the inhibition percentage of 86% as shown in the histogram of FIG. 17A. After the stimulation ended, the rate of APs rose back to 11 spike/s (at 1275 s-1276 s). When the second stimulating pulses were applied, also shown in FIG. 17B, the rate of APs decreased, and the cycles continued with the third and fourth stimulation as shown in FIGS. 17A-17C until pressure was released after 10 seconds. The arrows indicate the inhibition percentage compared with 1 second period earlier. From the results, with specific stimulating parameters, it is possible to achieve inhibition of near 100% where the neuron stops firing during the stimulation.

Figure 18A:
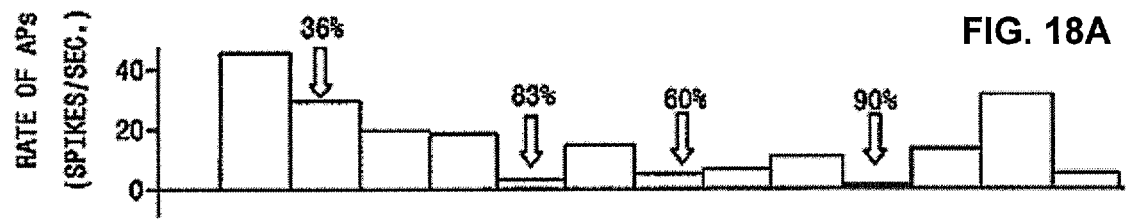
FIG. 18A shows the rate histogram of dorsal root neuron APs (spikes/second) from the trace in FIG. 18C before and after the periods of stimulation as shown in FIG. 18B.
Figure 18B:
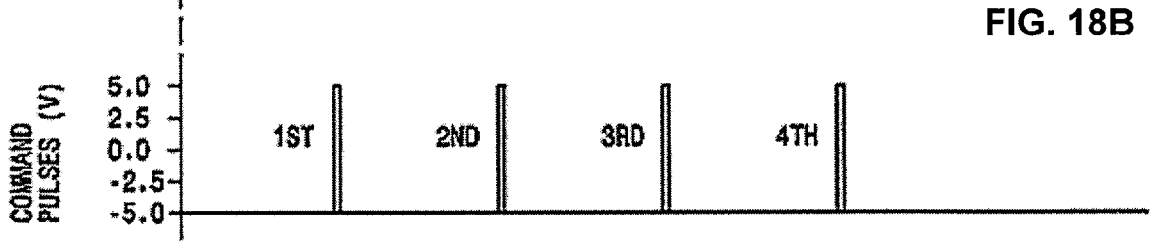
FIG. 18B indicates periods of ACC stimulation with 200 pulses, ±16V, 50 Hz and 0.5-ms duration.
Figure 18C:
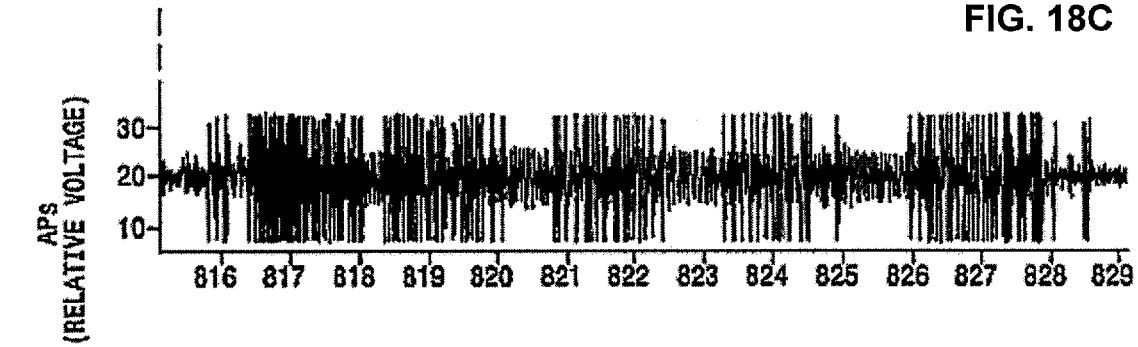
FIG. 18C is a trace of AP signals recorded from dorsal root neurons during periods of ACC stimulation shown in FIG. 18B.

The same phenomenon was observed for ACC stimulation. The AP rate reduces when the wireless stimulating pulses are applied as shown in FIGS. 18A-18C. The trace shown in FIG. 18C shows the recorded signals and the middle trace shown in FIG. 18B indicates wireless command pulses that activate the neurostimulation which lasts for 1 second after the end the command pulses. The trace shown in FIG. 18A shows the rate histogram of APs (spike/second) from the trace in FIG. 18C. The arrows indicate the inhibition percentage compared with 1 second period earlier. From the results, with specific stimulating parameters, it is possible to achieve inhibition of 90%, compared with previous period and near 100%, compared to the original control period.

Example 5

The system was tested in a freely moving animal. After craniotomy, a bipolar stimulating electrode (Science Products) was placed in the anterior cingulate cortex (ACC), Bregma 0.26 mm, and 0.5 mm left lateral to the midline, and 2.5 to 3.0 mm in depth. Another electrode was placed in the periaqueductal gray (PAG), posterior Bregma ~8 mm, 0.5 mm left lateral, and 4 mm in depth. The exact location may vary depending on the animal. The electrode was connected to the wireless device for bipolar stimulation (one electrode at a time). The Labview-based program recorded the action potentials transmitted from the sensor wirelessly and was manually controlled to activate the wireless neurostimulator. Electrical command pulses were delivered through the Labview-based m program in the computer to either the ACC or the PAG during mechanical stimuli. The commands produce the desired stimulation parameter in the stimulator. During each 10 second pain stimulation, electrical pulses (1 second in duration) were emitted four times with a 2 second interval. In the ACC stimulation, the parameters were 18 combinations of 11/16 v, 101501200 Hz, and 0.110.511 ms (pulse duration). In the PAG stimulation, there were 18 combinations of 0.210.611 v, 101501200 Hz, and 0.110.5 ms (pulse duration). At recording, three types of graded mechanical stimulations, brush, pressure, pinch, were applied on the hindpaw in a row with 20 second interval. Each type lasted 10 seconds. This part of electrophysiological recording was considered as a control.

Figure 19D:
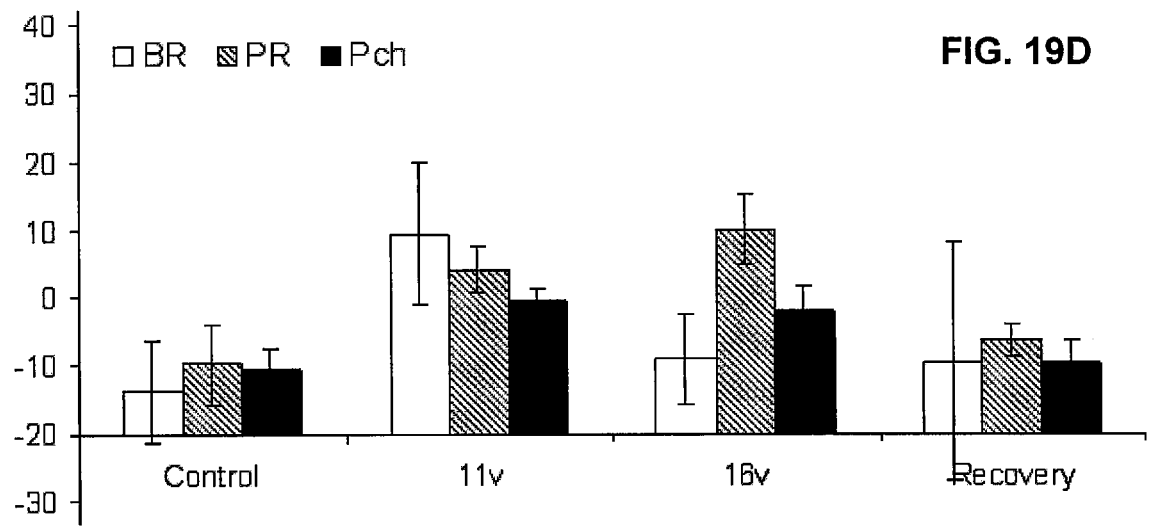
FIGS. 19D-F are graphs of the means of inhibition effects with standard errors with respect to the variables of voltage, frequency and pulse duration, respectively, for three graded mechanical stimuli, brush, pressure and pinch.
Figure 19E:
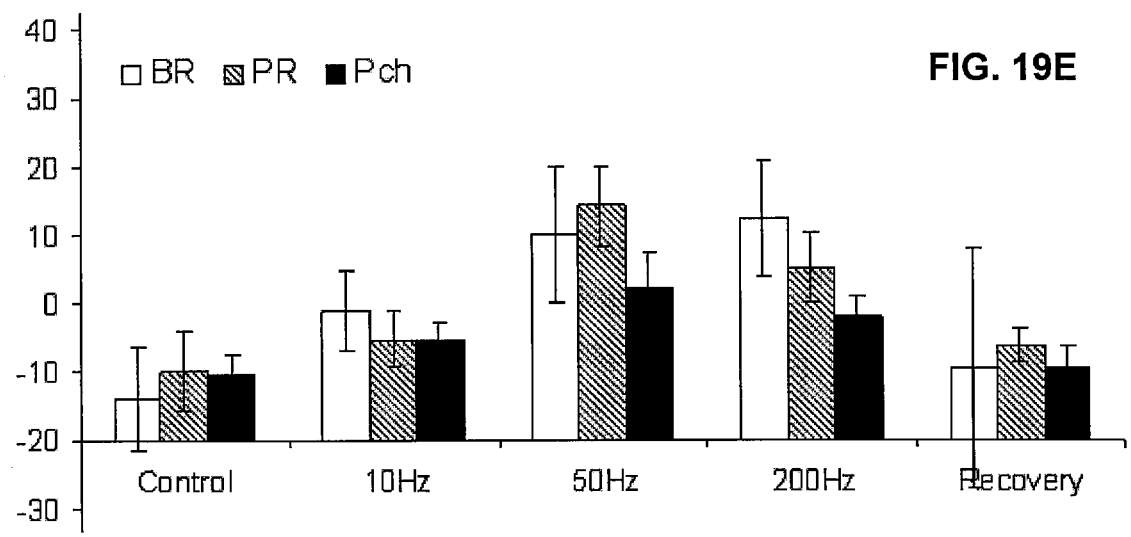
Figure 19F:
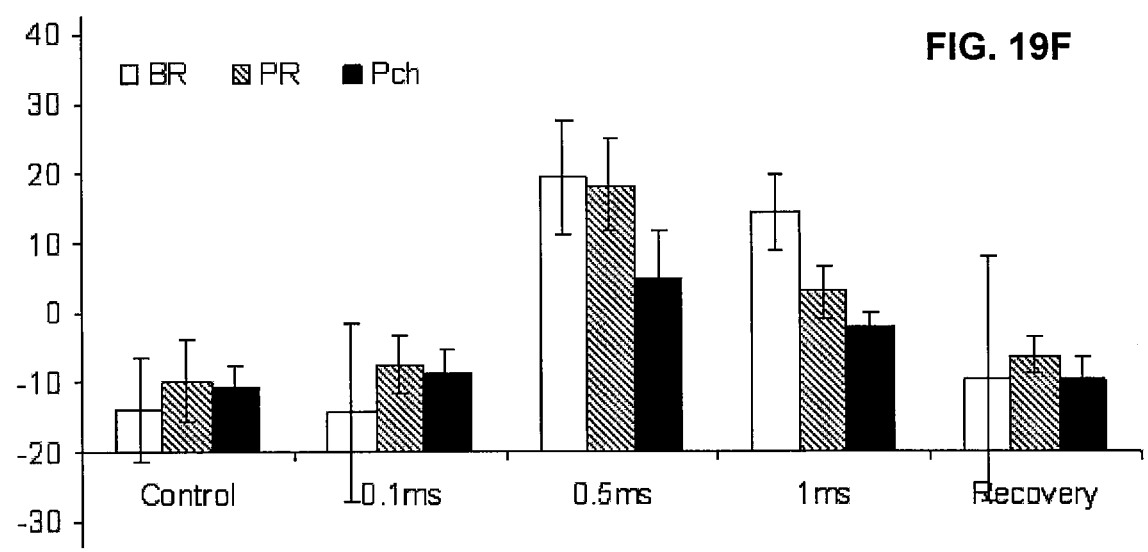

Twenty-two neurons had been classified in PAG stimulation files, and thirteen neurons had been distinguished in ACC stimulation recording. The results of a typical ACC stimulation for pinch stimuli are shown in FIGS. 19A-19C. FIG. 19A is a rate histogram showing the percentage of APs before and after stimulation commands, which is shown in FIG. 19B, after recording of dorsal root neurons in response to pressure stimulation to a rat hindpaw, as shown in FIG. 19C. FIGS. 19D-F contains the means of inhibition effects with standard errors with respect to the variables of voltage, frequency and pulse duration, for three graded mechanical stimuli, brush, pressure and pinch. ACC stimulation produces significant inhibition induced by noxious mechanical stimuli. Results indicate voltage, frequency, and pulse duration having significant main effects in pressure stimuli, but not in brush and pinch.

Figure 20D:
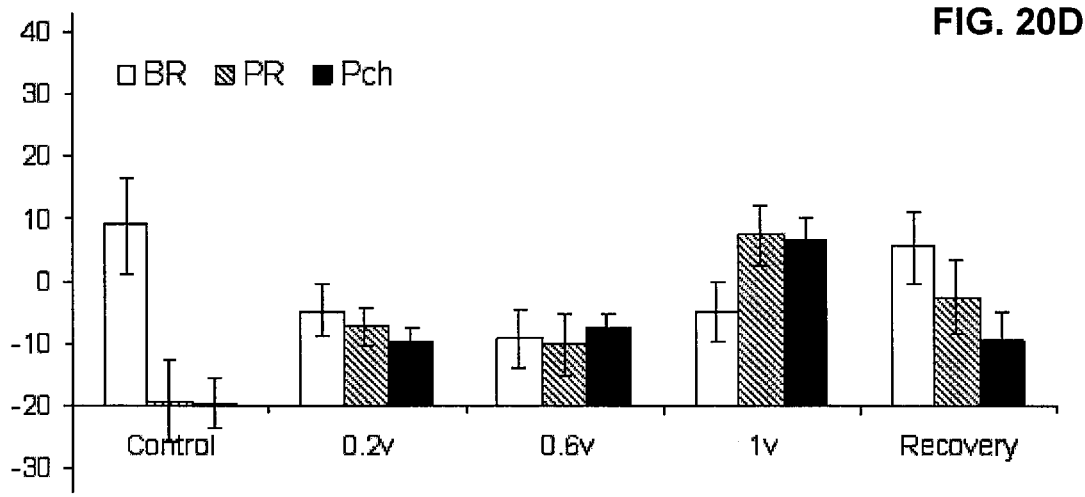
FIGS. 20D-F are graphs of the means of inhibition effects with standard errors with respect to the variables of voltage, frequency and pulse duration, respectively, for three graded mechanical stimuli, brush, pressure and pinch.
Figure 20E:
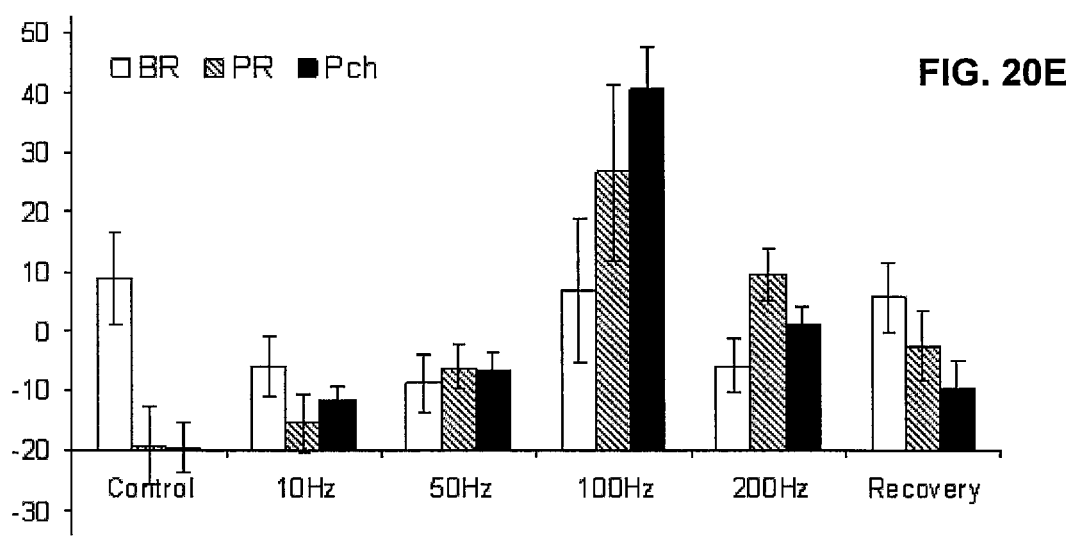
Figure 20F:
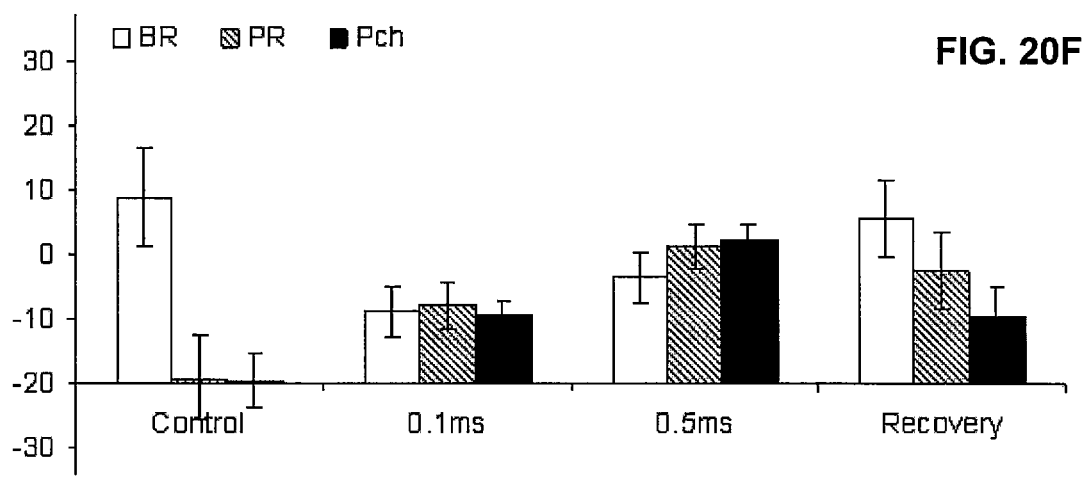

The results of PAG stimulation for pinch stimuli are shown in FIGS. 20A-20C. FIG. 20A is a rate histogram showing the percentage of APs before and after stimulation commands, which is shown in FIG. 20B, after recording of dorsal root neurons in response to pressure and pinch stimulation to a rat hindpaw, as represented in FIG. 20C. FIGS. 20D-F contains the means of inhibition effects with standard errors with respect to the variables of voltage, frequency and pulse duration, for three graded mechanical stimuli, brush, pressure and pinch. PAG stimulation produces significant inhibition induced by noxious mechanical stimulation. Results indicate voltage, frequency, and pulse duration having significant main effects in pressure and pinch stimuli, but not in brush. Smaller voltage (1V) in PAG stimulation could produce inhibition when larger voltage (11V) in ACC stimulation failed to produce constantly satisfactory inhibition.

Example 6

Self-Stimulation in Freely-Moving Rats Using a Wireless Device

Figure 21:
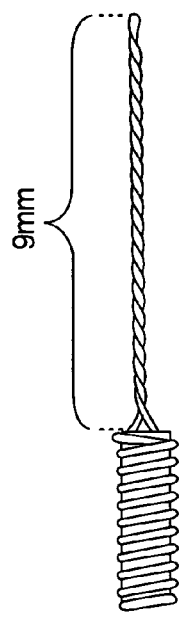
FIG. 21 is front view of an electrode for self stimulation experiments.

Two adult male Sprague-Dawley rats have been used in this experiment and the rates received electrode implants using 2-channel stainless steel electrodes (Plastics One Inc., Roanoke, Va.). Before surgery, animals were anesthetized using sodium pentobarbital (50 mg/kg; ip). Their heads were then fixed in a stereotaxic frame. A craniotomy was performed to implant a 9 mm long electrode, as shown in FIG. 21. Three mounting screws with length/diameter (1.6 mm/1.57 mm) shafts and 2.5 mm head diameter were inserted into the skull to aid in securing the electrode. Next the electrode was inserted into the horizontal limb of the diagonal band of Broca (from Bregma, 0.5 mm rostral, 0.5 mm lateral left, and 7.5 mm deep). Once the screws and electrode were in place, dental cement was used to fix the electrode. After the cement dried, the incision was sutured and animals' recovery was monitored. Animals were allowed a minimum of 4 days to recover from surgery before experimentation.

The wireless self-stimulation setup consists of the following: a receiver worn by the subject; the cages with a bar switch; the computer mouse connected to the bar switch; Labview-based software program written by us; and a wireless transmitter connected to the computer. Whenever the bar switch is pressed, it acts as a left-click on the mouse. The mouse pointer on the computer screen is positioned to press a virtual button in the Labview-based program. The activation signal is then carried to the transmitter, wirelessly broadcast to the receiver, and results in stimulation in the brain. In other words, each time the bar switch is pressed by the rat, stimulation is delivered.

Before each testing session, animals were mildly anesthetized with isoflurane. A vest was wrapped around the chest and the stimulator was attached to the vest. The stimulator was connected to the stimulating electrode, and the rat was transferred to the testing chamber. Prior to any testing, a stimulation threshold was determined by human and optimized for the best response.

Testing began with a pre-training session by allowing the rats to explore the chamber for approximately one hour to establish a bar switch pressing baseline. Since they were unable to learn bar pressing behavior on their own, their behavior was shaped so that they would push the bar switch to receive stimulation. Upon learning acquisition, the rats were allowed to press the bar switch freely in order to receive stimulation (Sessions 1 . . . n). After at least one successful session, a new session to study the affects of formalin was recorded as follows: 15 minute baseline, 15 minutes following injection of saline, and 60 minutes following injection of formalin. Injections consisted of 50 µl of saline or formalin and were inserted into the dorsal side of one hindpaw.

Figure 22A:
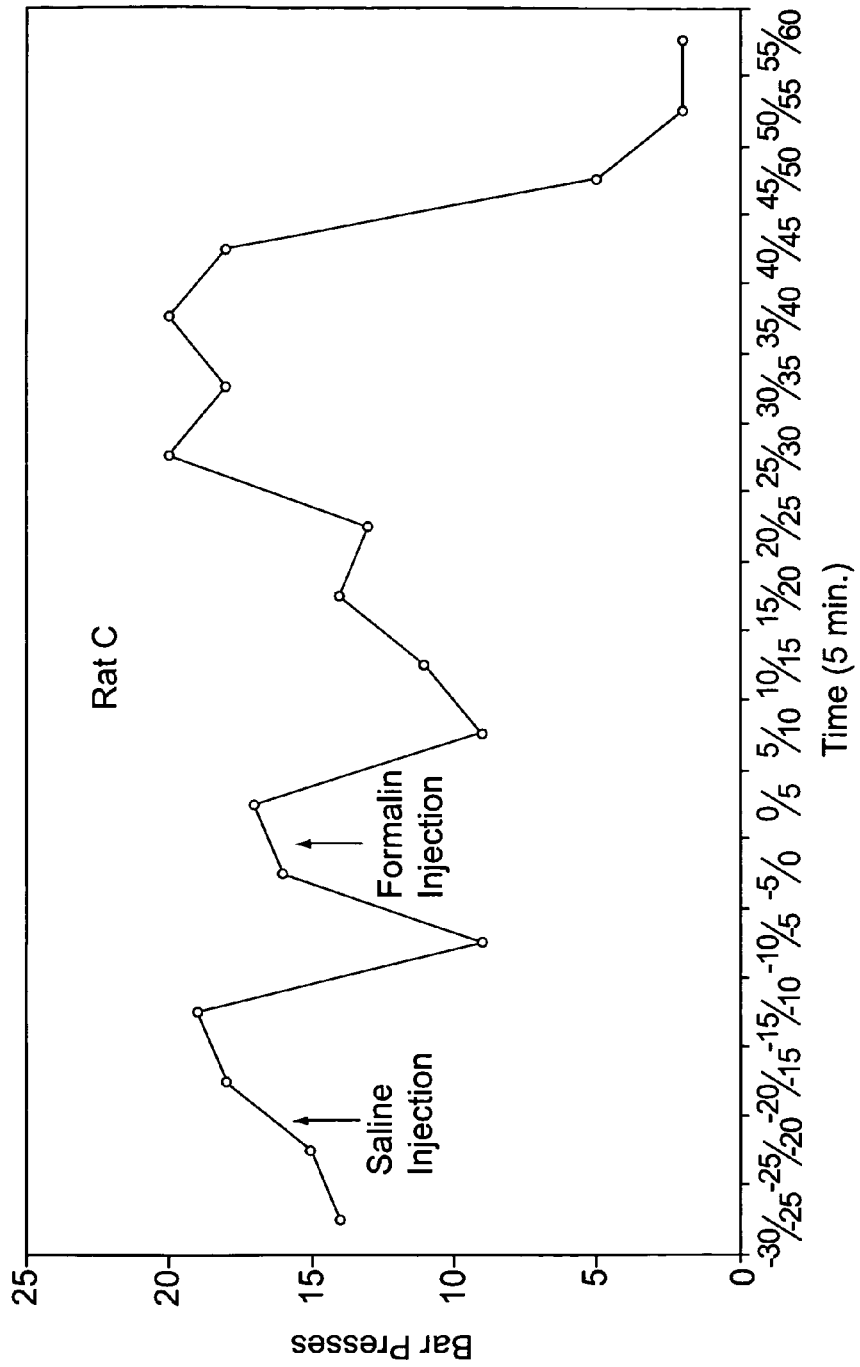
FIGS. 22A and 22B are graphs of the responses of self stimulation by counting the numbers of pressing a bar switch to saline and formalin injection in two rats, Rat C and Rat D, respectively.
Figure 22B:
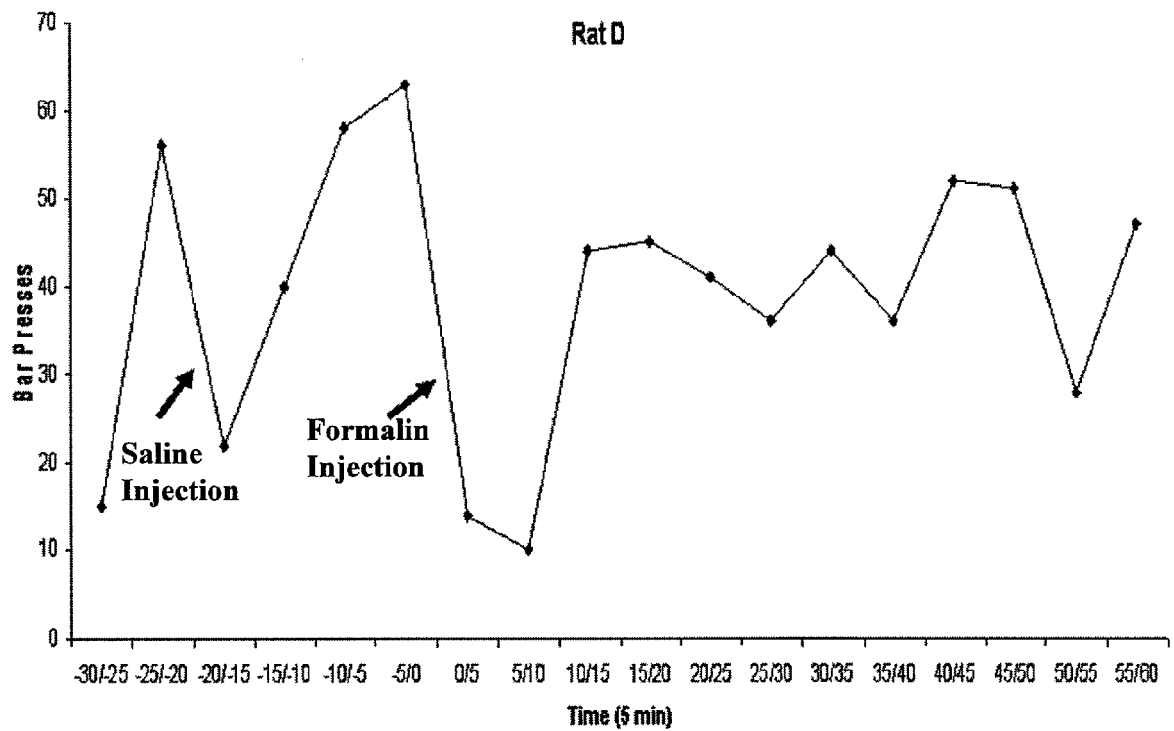
Figure 22C:
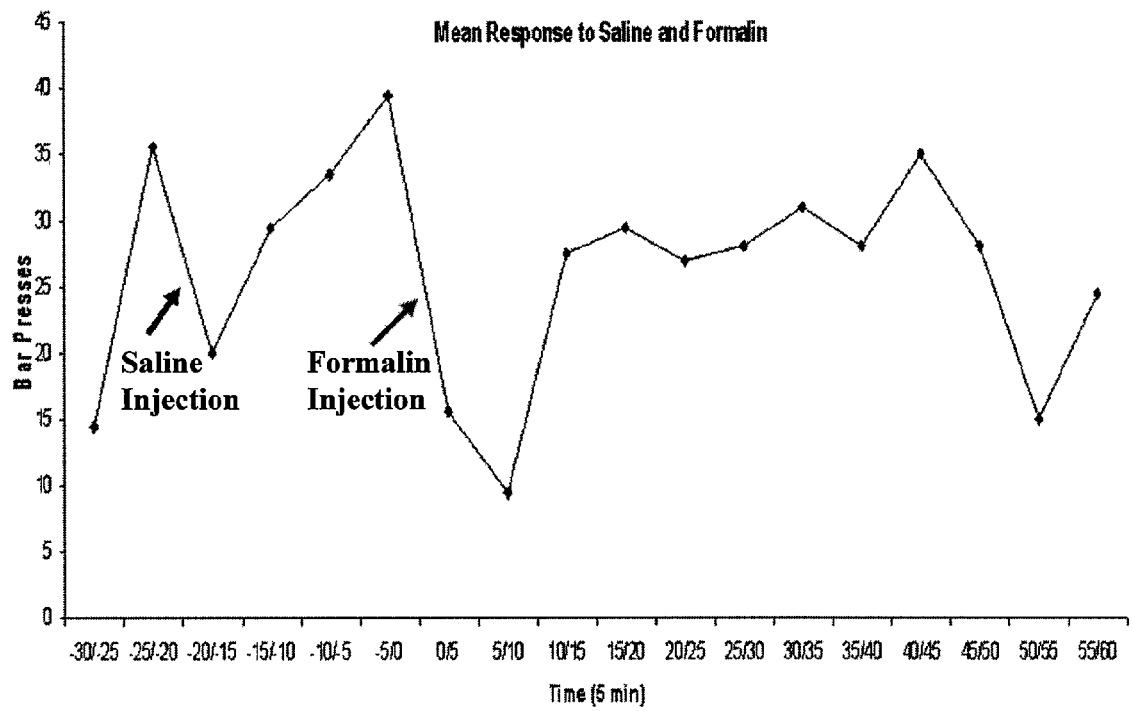
FIG. 22C is a graph of the mean responses to saline and formalin.

FIG. 22A shows the responses to saline and formalin injection for the Rat C. FIG. 22B shows responses to saline and formalin injection for the Rat D. FIG. 22C shows the mean responses for saline and formalin injection.

Figure 23A:
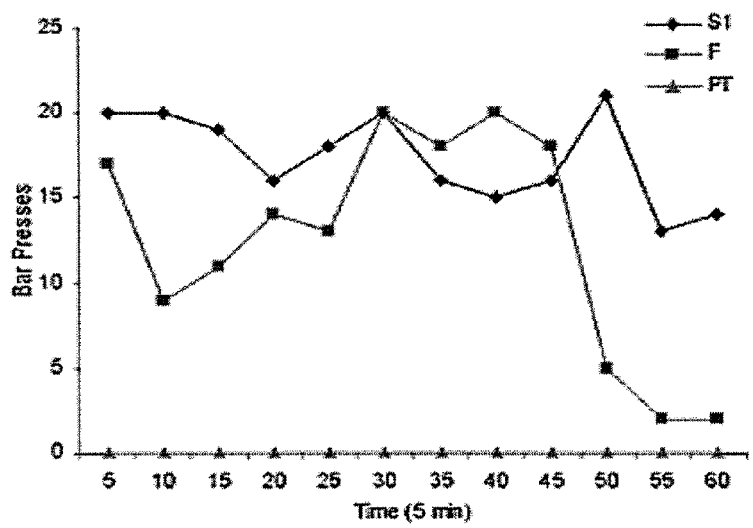
FIGS. 23A-C are graphs of the responses for Pre-training Session (PT), Session 1 (S1), and Formalin Session (F) in Rat C, Rat D, and mean response, respectively.
Figure 23B:
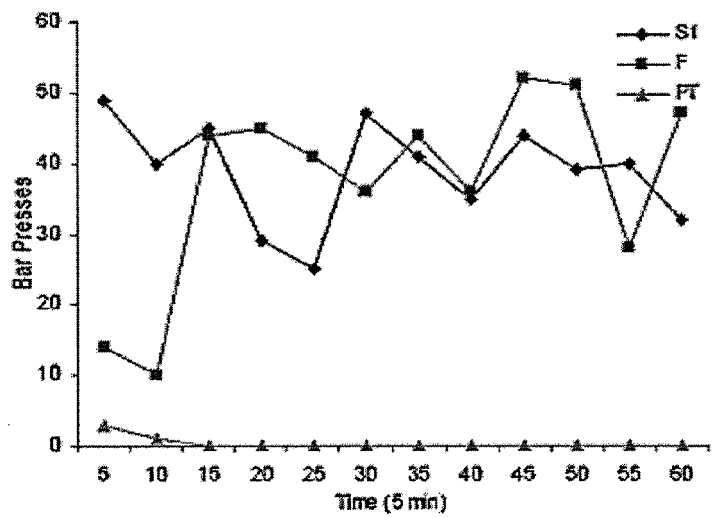
Figure 23C:
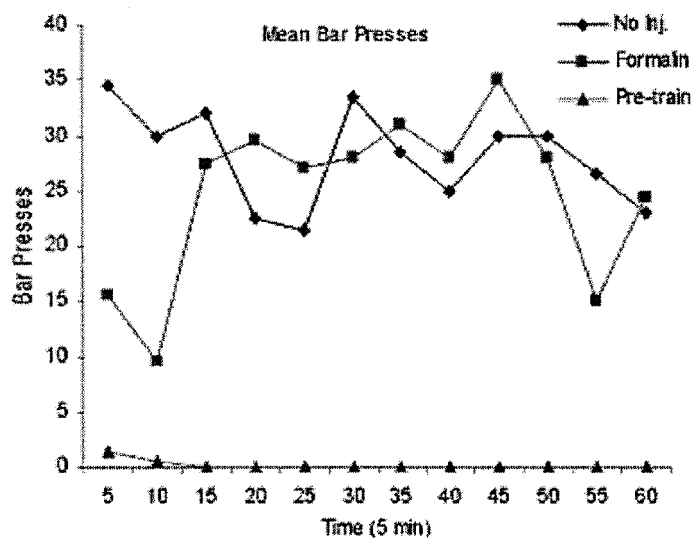

FIGS. 23A-C show the responses for the Rat C, the Rat D and mean responses during Pre-training Session (PT), Session 1 (S1), and Formalin Session (F), respectively.

These data indicate that rats will learn to press a bar switch to receive electrical stimulation in the septum in order to receive pain inhibition. The data suggest that the bar switch pressing is not affected by a noxious stimulus, except maybe in the initial stages of formalin evoked behavior. Pain behaviors are most intense in the initial phase of the formalin test, suggesting that pain too is most intense in the beginning. The initial pain may be too much to inhibit in this case and may also be interfering with the animals' ability to attend to bar switch pressing.

Automatic inhibition of pain: By detecting the neural activity associated with pain, brain stimulation may be triggered in pain inhibition areas of the brain to lead to analgesia. Once analgesia is achieved, brain stimulation will be ceased, which will be accomplished by designing a closed-loop feedback system for the purpose of modulating pain.

Example 7

Using Interspike Interval Features for Pain Recognition

The animal preparation procedure is similar to the ones mentioned before. Using the electrodes for rats under anesthesia, once the neuron was identified templates of the recorded action potentials (AP) to three mechanical stimuli of brush, pressure, and pinch were formed. The neuron responses were examined in a window of APs using the interspike interval (ISI) as the main feature. The ISIs were counted within the window and if the time difference for the spikes becomes less than a specified threshold, the signals then were recognized as pain. Three sets of lumbar spinal cord dorsal horn neurons from 3 anesthetized rats were recorded in response to peripheral graded mechanical stimuli. Results showed that in a window with less than 15 APs, the optimal ISIs for pain signal was between 10-20 ms. The identified feature for each neuron was different but there was an optimal window and ISI for each. Combined with the action potential template, the ISI feature provides more accuracy recognizing pain signals.

A method of characterizing pain signals from recorded action potentials in the spinal cord and the related pain inhibition effects with neuro-stimulation in the brain. The experiment configuration as shown previously is that a recording electrode at the spinal cord records single neuron action potentials while an electrode is inserted in the motor cortex for stimulation. After a search for a spinal dorsal horn neuron, the background activity and responses to graded mechanical stimuli (brush, pressure, and pinch) at the foot are made in single-unit extracellular recordings.

At recording, three types of graded mechanical stimulations, brush, pressure, pinch, were applied on the hindpaw in a row with 20 second intervals. Each type lasted 10 seconds. This part of electrophysiological recording was considered as a control. Spinal dorsal horn WDR (wide dynamic range) neurons were searched by gentle touch. The receptive field was located on the center of hind paws. After the WDR neuron was identified (at least three neurons), graded mechanical stimulation, brush, pressure, and pinch, were delivered. All data were collected wirelessly by a CED 1401Plus and controlled by analyzed by Spike2 and the Labview-based software program.

Figure 24A:
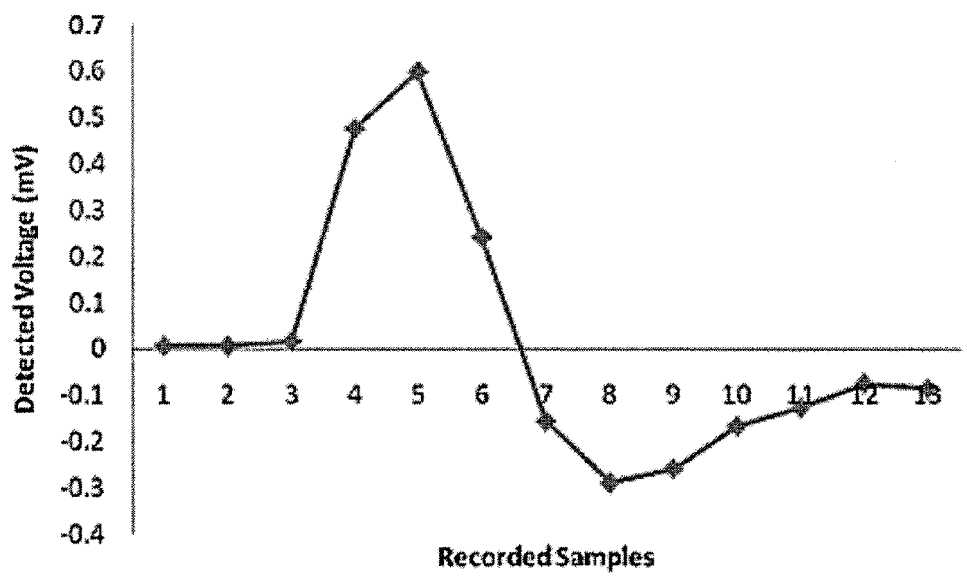
FIG. 24A is a graph of AP sampling for interspike interval (ISI), where the samples over 0.4 mV and less than −0.2 can be considered as "1", where the digital pattern created is 0011001100.
Figure 24B:
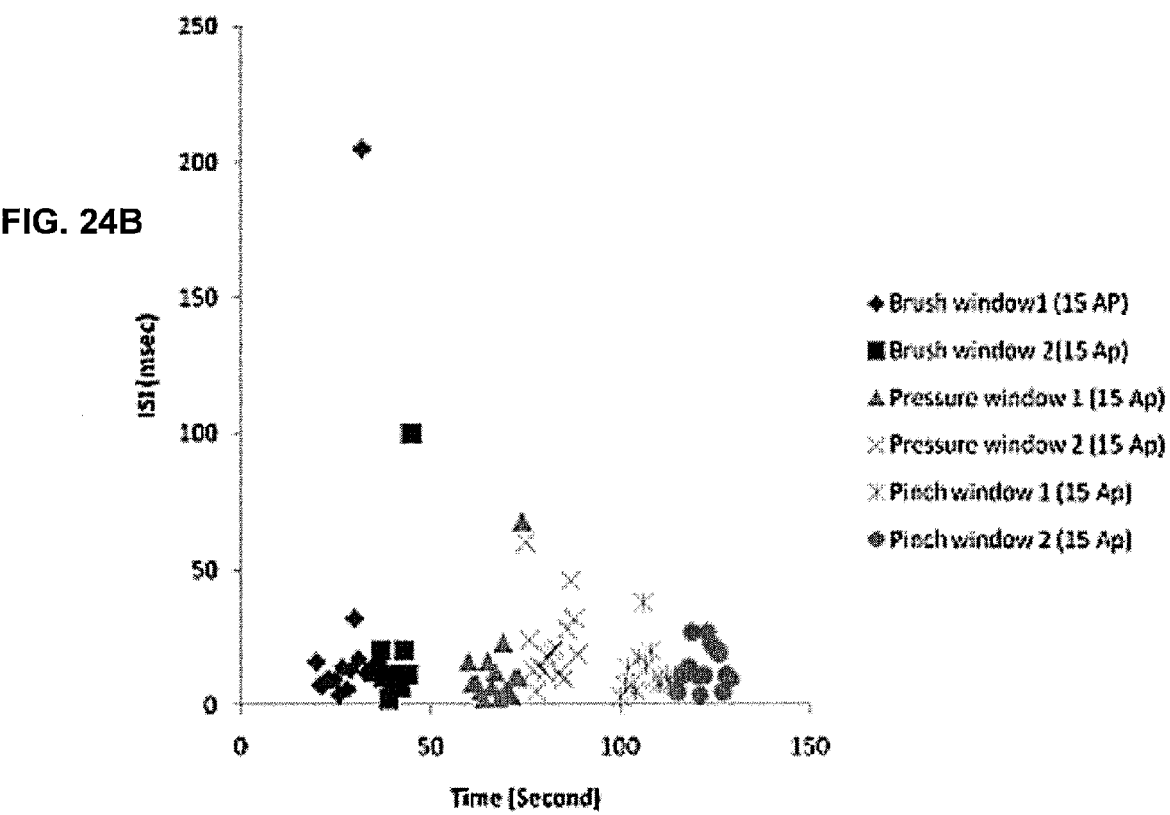
FIG. 24 B is a graph of the differences in ISIs for brush, pressure, and pinch in a window of 15 APs.

APs were found using two-peak detectors. One for the positive peak and one for the negative peak. Any value over the positive threshold and any value less than a negative threshold are considered as "1". All the other values in between are considered as "0". Therefore, a pattern for AP formed (FIG. 24A). ISIs for each set of data was calculated. Different windows of number of ISIs were examined. The typical window contained 15±5 ISIs and the typical ISI for both pressure and pinch is about 30±10 ms. Considering the ISI windows, for the brush and pressure there is at least one ISI which happened out of the range, but in the pinch situation all of ISIs of the window are less than a threshold (typically 40 ms). As it is shown in FIG. 24B, brush, pressure and pinch pain signals can be categorized in a window of 15 APs.

ISI is incorporated for identifying the action potential signals of different stimuli in the nervous system. Adding a window that contains a specific number of action potentials to ISI leads to the recognition of the pain stimuli such as brush, pressure and pinch. With a narrow window in the time domain, the pain signals can be recognized in real-time applications. As the recorded signals are transmitted from the sensor to the remote processing device, the signals are buffered in a certain ISI window. After the window period, the signal is categorized as an action potential or not. Then the buffer is cleared out for the next period. The windows to count ISIs and the time period to define an ISI are reconfigurable and can be optimized for a certain animal or individual person. The reconfigurability is in the software of the remote processing device providing individuality, so that one can control to reach optimized recognition for feedback in pain management.

Example 8

Efficacy of the Wireless System

Twenty-three Sprague-Dawley male rats, 60-90 days old, were used. Under sodium pentobarbital anesthesia (50 mg/kg, i.p.), Laminectomies were performed to expose lumbosacral part of the spinal cord. A continuous intravenous perfusion of 5 mg/hr of pentobarbital was used for maintaining anesthesia during experiment. Out of 23 rats, 20 received electrode placed in the ACC (Bregma 0 mm, 0.5 mm left lateral, and 2.5-3.0 mm in depth), 6 in the PAG (posterior Bregma −8 mm, 0.5 mm left lateral, and 4 mm in depth), and 3 in the M1 (anterior Bregma 0.25 mm, 2 mm lateral, and 0.5 mm deep). After the dura mater was removed from the surface of spinal cord, a tungsten electrode was used to search for dorsal horn neurons and record action potentials.

Three types of graded mechanical stimulations, brush, pressure, pinch, were applied on the hindpaw in a row with 20 second interval. Each type lasted 10 seconds. This recording was considered as a control. Electrical pulses were delivered through the LabView-based program in computer to either the ACC or the PAG during mechanical stimulations. During each 10 second stimulation, electrical pulses (1 second in duration) were emitted four times with 2 second interval. Before the end of continuous recording, brush, pressure, and pinch were applied again without electrical stimulation as a recovery group of signals for comparison.

22 neurons had been distinguished in PAG stimulation data files, and 13 neurons in ACC stimulation recording. The histogram has been exported from raw data and recognized as action potentials. The statistical significance was summarized. Independent variables are the stimulation parameters: voltage (V), frequency (Hz), and pulse duration (ms). Dependent variable is the inhibition score calculated by the equation (1):

$$Inhi = \frac{(B_1 + B_2) - (A_1 + A_2)}{B_1 + B_2} \times 100\%. \quad (1)$$

FIG. 25A shows the measurement of inhibition. FIG. 25A shows an example of histogram of dorsal horn neuronal activity induced by pressure or pinch, including the formula to measure the extent of inhibition. FIG. 25B shows a typical histogram representing inhibition induced by electrical stimulation. FIGS. 25C and D shows representative traces of the inhibition scores and FIG. 25E is the interpretation of "inhi" as described on the y-axis, where the greater the "inhi" is, the stronger the inhibition is.

Figure 26A:
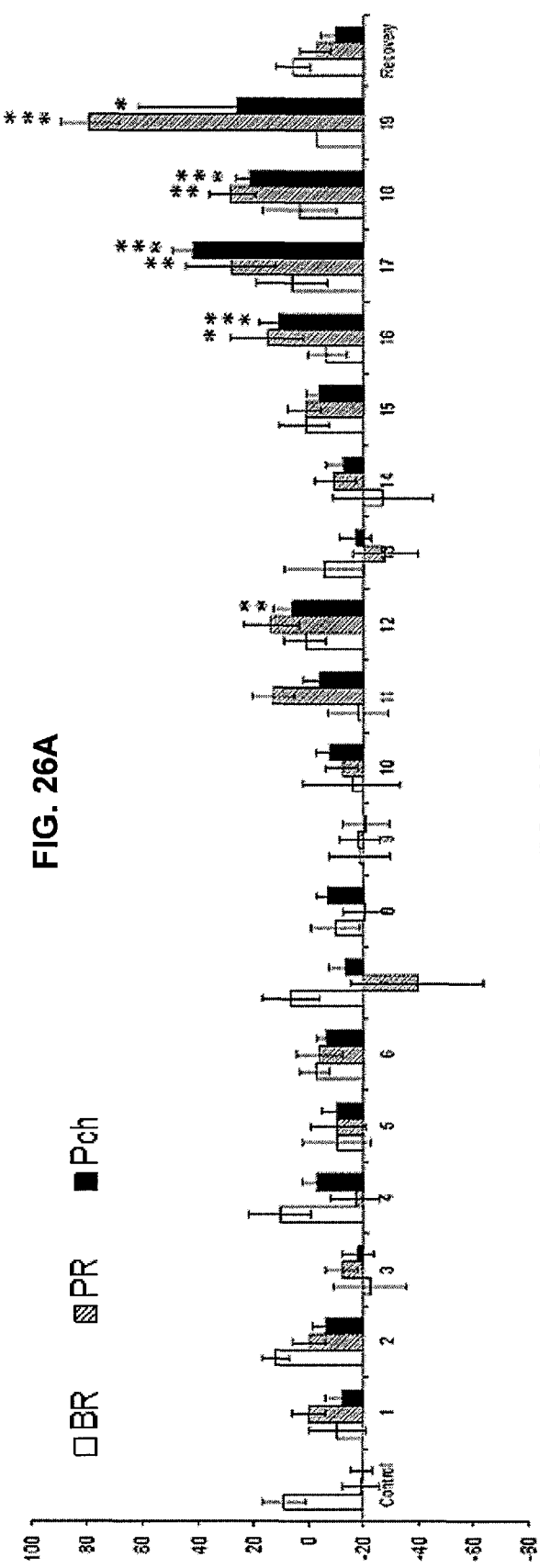
FIGS. 26A and B are graphs of the inhi scores under each set of electrical stimulation parameters for PAG and ACC, respectively.
Figure 26B:
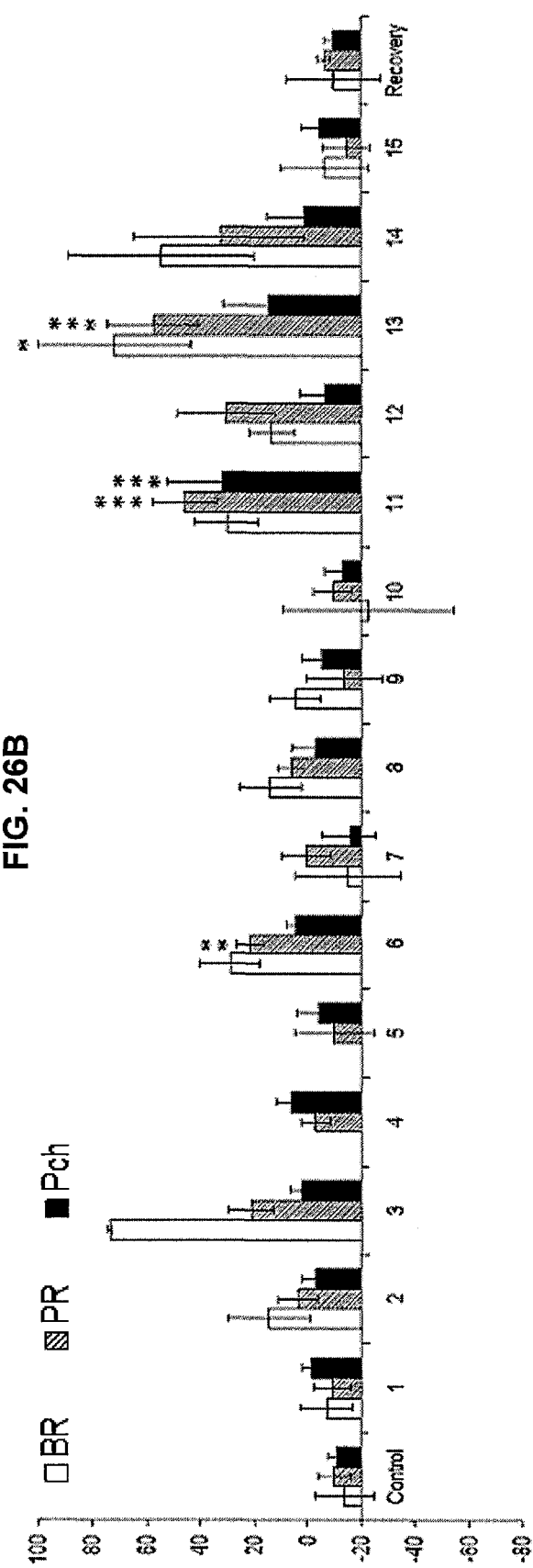

FIG. 26A shows the "inhi" scores under each set of electrical stimulation parameters for PAG (upper) and ACC (bottom) stimulation. The Table 1 shows the stimulation parameter sets (voltage (V), frequency (Hz), duration (ms)).

TABLE 1

The inhi scores under set of electrical parameters for PAG and ACC

| No. | PAG | ACC |
| --- | --- | --- |
| 1 | 0.2-10-0.1 | 11-10-1 |
| 2 | 0.2-10-0.5 | 11-50-1 |
| 3 | 0.2-50-0.1 | 11-100-1 |
| 4 | 0.2-50-0.5 | 11-200-0.1 |
| 5 | 0.2-200-0.1 | 11-200-0.5 |
| 6 | 0.2-200-0.5 | 11-200-1 |
| 7 | 0.6-10-0.1 | 16-10-0.1 |
| 8 | 0.6-10-0.5 | 16-10-0.5 |
| 9 | 0.6-50-0.1 | 16-10-1 |
| 10 | 0.6-50-0.5 | 16-50-0.1 |
| 11 | 0.6-200-0.1 | 16-50-0.5 |
| 12 | 0.6-200-0.5 | 16-50-1 |
| 13 | 1-10-0.1 | 16-100-0.3 |
| 14 | 1-10-0.5 | 16-100-0.5 |
| 15 | 1-50-0.1 | 16-200-0.1 |
| 16 | 1-50-0.5 | |
| 17 | 1-100-0.5 | |
| 18 | 1-200-0.1 | |
| 19 | 1-200-0.5 | |

For PAG, stimulation sets 12, 16, 17, 18, and 19 produce significant greater "inhi" than in control for pressure and/or pinch. For ACC, stimulation sets 6, 11 and 13 produce similar significant greater than "inhi" results. The significance of probability is also shown in the bar graph, in which * means $p<0.05$;  $p<0.01$; and * $p<0.001$. The bar graphs present the "inhi" in terms of mean and standard errors of mean (mean±SEM) in brush (BR), pressure (PR), and pinch (Pch) stimuli.

Figure 27B:
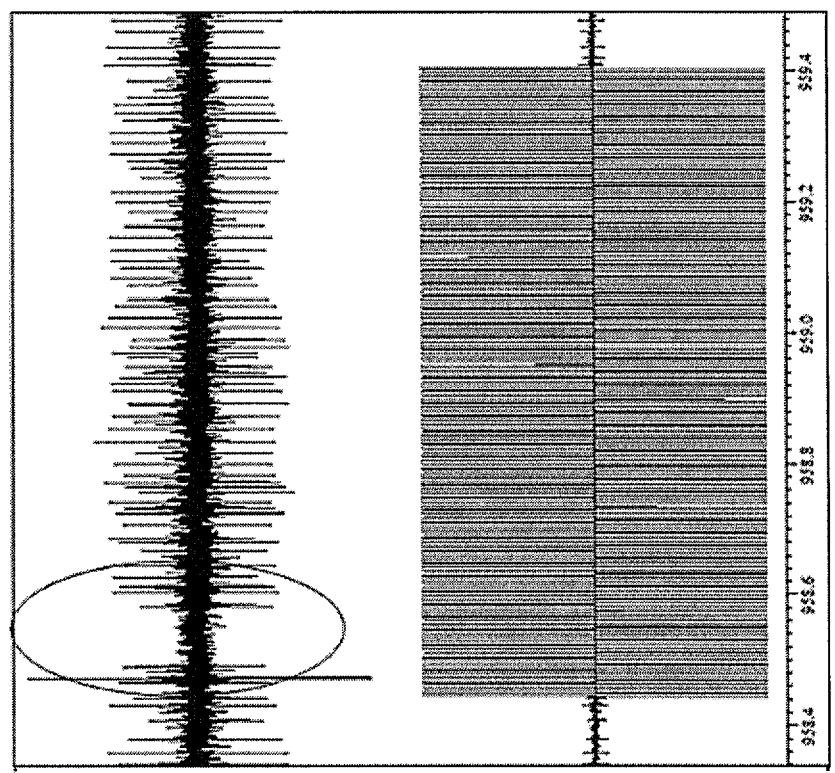
FIG. 27B is an exploded view of the inset box on FIG. 27A.
Figure 27A:
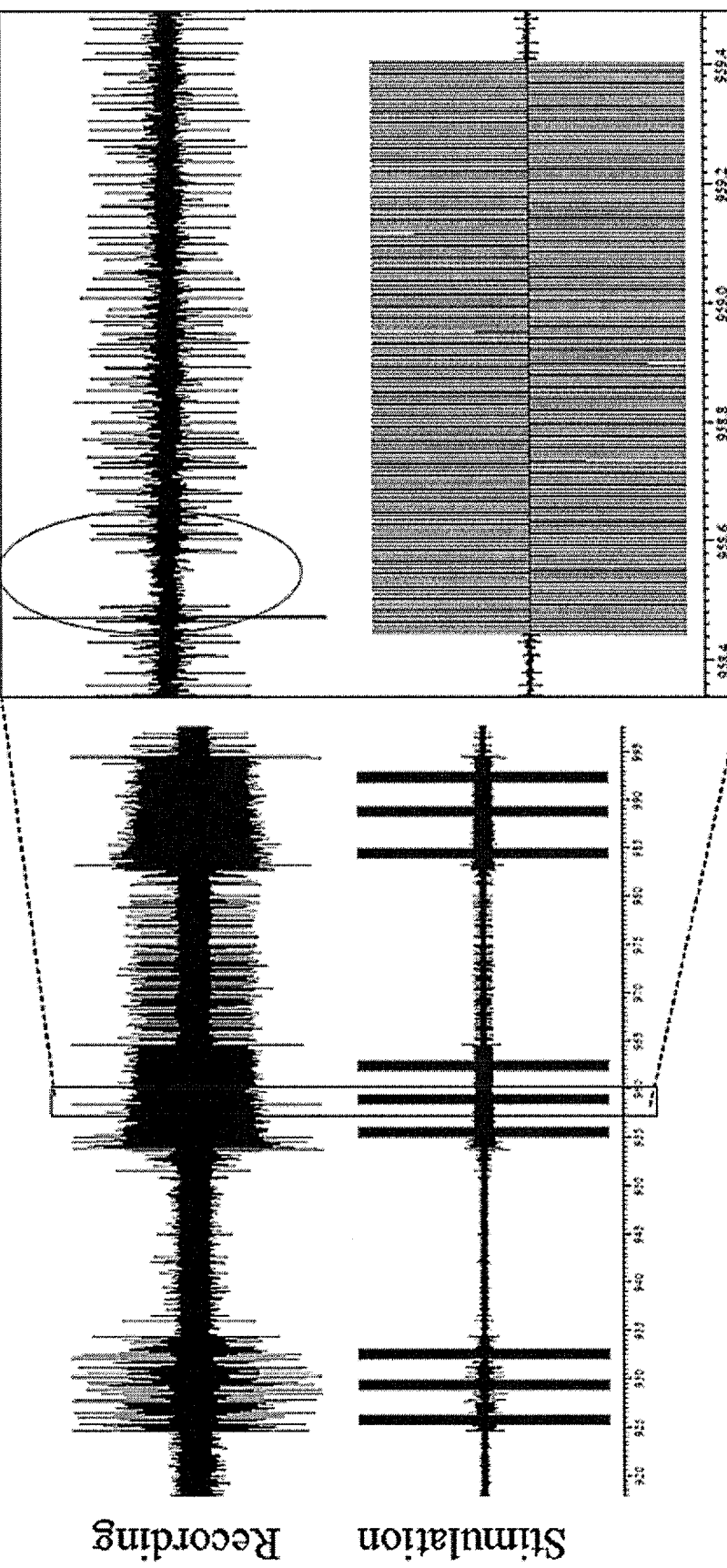
FIG. 27A is a graph of motor cortex stimulation induced inhibition of the spinal cord dorsal horn neurons with astimulation parameter for 20V-200 Hz-5 ms, where the upper channel is electrophysiological recording, and the lower channel is the artifacts of stimulation pulses, and the X-axis is time in seconds.

FIG. 27A shows motor cortex stimulation induced inhibition of the spinal cord dorsal horn neurons. This example was recorded with stimulation parameters of 20V-200 Hz-5 ms. FIG. 27B shows the details zoomed in the time domain. The upper trace is the recorded signal, and the lower trace is the artifacts of stimulation pulses. The inhibition (highlighted by the circle) only occurred in the first 200-300 ms during 1s stimulation.

Electrical stimulation in both the ACC and PAG produces inhibition of dorsal horn neuronal activity induced by noxious mechanical stimulation. Statistical data shows ACC stimulation was less efficient than PAG stimulation to produce inhibition and motor cortex stimulation might produce short-lasting inhibition. Therefore, a feedback mechanism between the sensor and the stimulator is required in order to optimize pain inhibition in various stimulation cases.

Example 9

RFID-Based Multi-Sensor, Multi-Stimulator Body Network for the Closed-Loop Feedback Pain Management The described system is suitable for any batteryless or low-power rechargeable medical diagnostic/therapeutic implants in an integrated wireless systems applied in a body area network. System perspectives include hardware integration: sensors and stimulators are wirelessly integrated in the body network system, a feedback algorithm integration for the sensors and stimulators in a closed-loop to reach optimal performance, an RFID-based communication protocol to allow multiple implants and wearable devices in the same body network communicating among themselves and between a remote processing device and a batteryless or rechargeable-battery operation with RF energy harvesting for long-term uses.

Body area communication between implants and external module includes an inductive coupling to transmit both energy and data signals and an RFID-based identification mechanism for body area networking device identification. Implantable physiological parameter recording includes flexible electrodes mentioned above to detect physiological signals (such as action potentials), resonant circuit to amplify signal strength, integration of sensor signals and ID coding to ensure signal integrity among body area network. Implantable physiological parameter stimulation includes resonant circuitry and charge pumps to deliver electrical power into neurons or tissues, power rectifiers to ensure stimulation signal integrity or to be used for rechargeable batteries. The body area networking interfaces to data logging (smart media) in a portable computing device or mobile phone through the remote processing device.

Figure 28A:
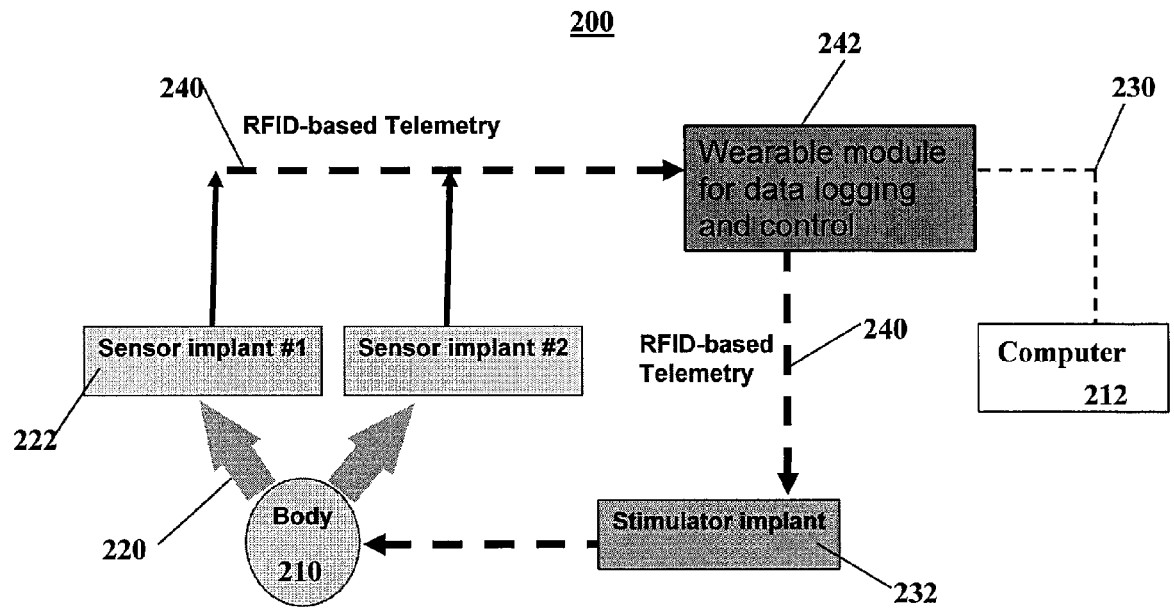
FIG. 28A is a schematic of a system interface between a body and computer with body network communication based on RFID telemetry.
Figure 28B:
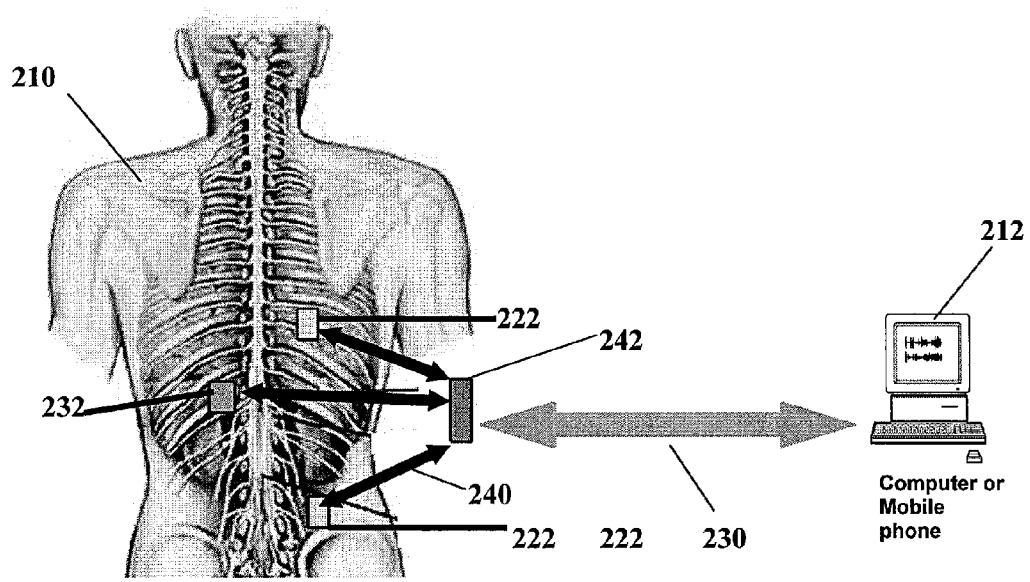
FIG. 28B is a perspective and schematic view of the system interface between a body and computer with body network communication based on RFID telemetry.

As shown in FIGS. 28A and 28B, the system 200 is an interface between the human/animal body 210 and computer 212. The system includes a feedback mechanism between sensor signals 220 from the body to the computer and therapeutic signals 230 from the computer to the body with a batteryless/rechargeable-battery solution using RF energy harvesting for sensors and stimulators. The RFID-based solution allows multiple sensor implants 222, multiple stimulator implants 232 and wearable devices 242 in the body. The feedback system including automatic control from the recorded physiological signals to reach optimal comfort and treatment success. The sensor signals 220 are sensed by sensor implants 222, which communicate via RFID-based telemetry 240 with a wireless module 242. The wearable module, can be the remote processing device mentioned above itself, 242 communicates with the computer to determine the stimulating signals 230 to a stimulator implant 232. The communication between the wearable module 242 and the computer 212 can be continuous or on demand. The neuro-stimulator implant(s) 232 can be programmed with the external module 242 to generate the most suitable stimulation signals for the individual patient. The wireless wearable module receives the detected pain signals from the sensor implants and transmits command signals to the neurostimulator automatically after patient's setting. With a graphic interface control, the detected pain signals can be analyzed quantitatively in the computer. A closed-loop software in the wearable module 242 synthesizes the optimized stimulating signals from the recorded pain levels. The patient can also use the graphics interface in the wearable module or the computer to control the comfort level and set the ISI recognition algorithm to identify action potentials representing individual's pains. The closed loop software will filter the electrical signals, recognize the target action potentials, and classify the action potentials into pain classes. The pain signals then will be fed into an adaptive system in the computer or the wearable module to learn about the pain signal patterns with respect to the stimulation signals. The system will adaptively vary to reflect the current condition of the human nervous system. The system will recommend an optimized set of parameters, including electrical current strength, durations and frequencies, of stimulation which will achieve the patient's desired comfort level. The software synthesizes the stimulation signals and transmits the signals to the neurostimulator implant. The pain data recorded in the module memory card or the computer can provide doctors quantitative information about the patient's pain later.

Figure 29:
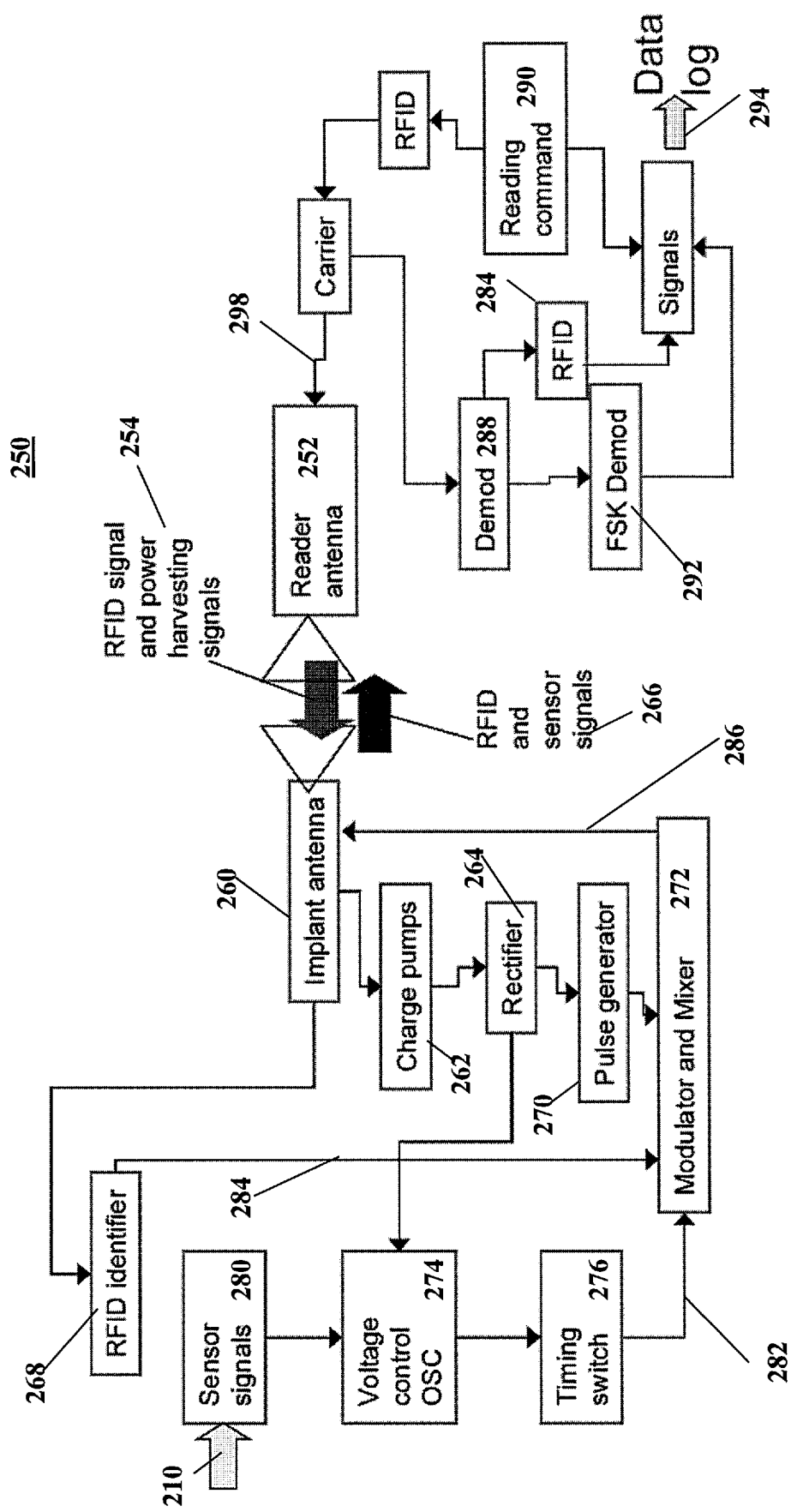
FIG. 29 is a schematic of a sensor implant circuit diagram using body network communication based on RFID telemetry.

As shown in FIG. 29, the sensing subsystem 250 includes an RFID reader 252 that sends RF signals 254 to the sensor implant 222 and receives encoded sensor signal carrier 266. The control in the wearable module 242 sends reading commands 290 and RFID information to a carrier generator. The generated signals 254 include RFID and reading commands in the RF carrier signals broadcast from the reader antenna 252.

In the sensor implant 222, an implant antenna 260 receives the signals 254 and separates the RF carrier signal to a charge pump 262 and a rectifier 264 for harvesting the RF energy from the signal 254. The RFID codes are separated to RFID identifier 268 and if the RFID identified is not the same as the ID of the implant, the harvested energy will not be used. If the ID number is the interested number by the external module, the harvested energy will be used to drive a pulse generator 270, a modulator 272, a voltage control OSC 274, and a timing switch 276. The sensor signals 280 come from body tissues 210. The sensor signals 280 measure resistance, capacitance or action potential (voltage generated by neurons in the pain management case). The sensor signals 280 are fed to the oscillator 274 and the timing switch 276 to achieve a frequency shift keying (FSK) modulation signal 282. A FSK system has two operating frequencies that are digitally generated by a series of D flip-flops to divide the carrier frequency from the reader. To mitigate the possibility of noise affecting the physiological signals, frequency shift keying provides a mean to prevent tissue artifacts. The FSK modulation signals 282 go to the modulator and mixer 272 to mix with ID number 284 into the carrier frequency 286. The implant antenna 260 sends the carrier frequency 266 out. The carrier frequency 266 may or may not be the same frequency as the carrier frequency 254 from the reader antenna. The reader antennae 252 detects the carrier frequency 266 and feeds into a demodulator 288. The RFID information 284 and the FSK signals are separated by the demodulator 288. The RFID information 284 is compared with the reading command 290, which initiates the reading command for the desired implant ID. When the ID numbers are identical, the FSK signals are demodulated with a FSK demodulator 292 to the original physiological signals 210. Together the signals and ID are sent to data logging mechanism 294 in the wearable module 242 and the software for action potential recognition (such as the ISI method mentioned before) and the feedback software to synthesize the desired stimulation parameters.

Figure 30:
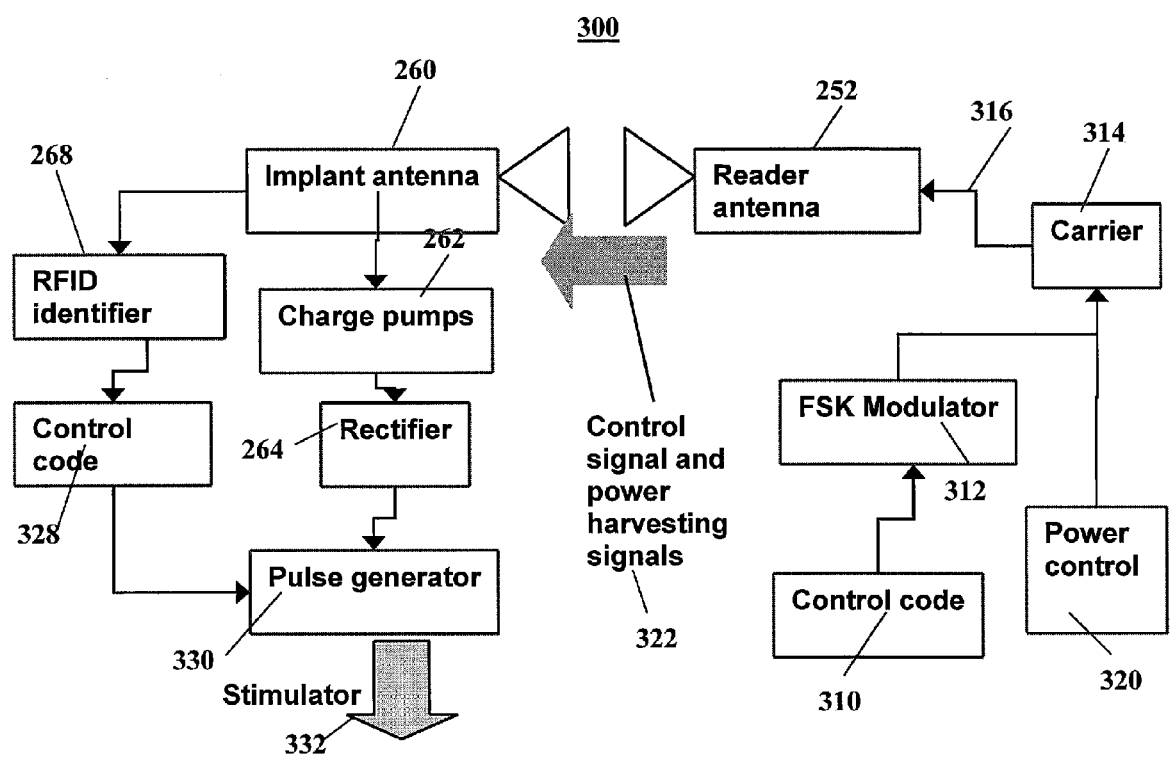
FIG. 30 is a schematic of the stimulator implant circuit with the RFID body network communication based on telemetry.

Therapeutic subsystem 300 is shown in FIG. 30 as the stimulator implant circuit diagram. The control code 310 commands are requested from the feedback software, either by human control or from automatic feedback mechanism, and the control code 310 is modulated by an FSK modulator 312. A carrier signal 314 is controlled with a RF power control 320. If the communication distance between the reader and the implant is shorter, the required RF power provided by the power control 320 is lower, which can prevent tissue damage by heating of high power RF signals. The carrier signal 316 is sent to the reader antenna 252. The implant antenna 260 receives carrier signals containing the stimulation command and power harvesting signals 322. The carrier frequency of the signal 322 can be the same as the ones 254 and/or 266. The RFID communication architecture avoids communication collision. Using the same carrier frequency simplifies the system requirement and implementation. The RFID information is separated to the RFID identifier 268. If the RFID information is correct, the control command 328 is used to generate stimulation pulses 332 by a pulse generator 330 with required voltage, frequency and duration. At the same time, RF energy is harvested to drive the pulse generator 330 by the charge pump 262 and the rectifier 264. The pulses 332 then are used for stimulation of neurons.

Figure 31:
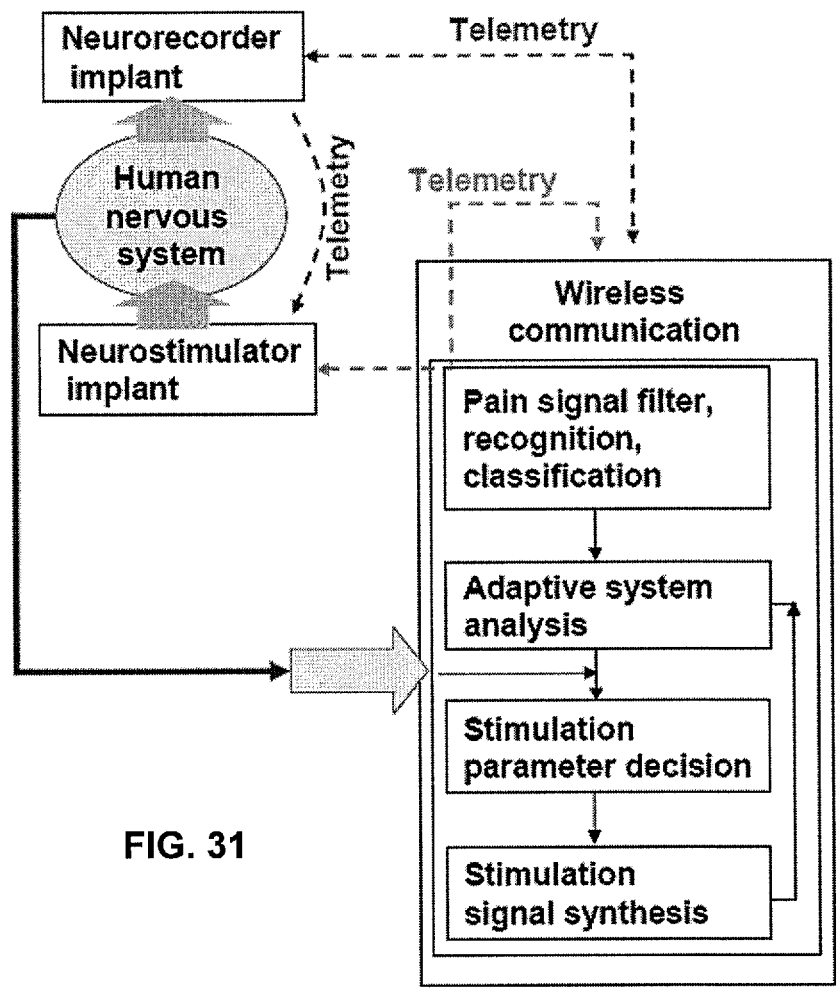
FIG. 31 is a schematic block diagram of feedback loop integration with the human nervous system.

As shown in FIG. 31, when a patient manually sets his/her comfort level, algorithms will be adjusted including the parameters for feedback from patient setting (subject feeling by individuals), comfort level recognition, and stimulation parameter decision to decide the optimal set of stimulation parameters. The diagram shows the flowchart of the closed-loop feedback. The sensor (neurorecorders) implants transmit the recorded signals to the external module through the RFID-based communication mentioned above. The signals are first filtered, denoised and recognized by the ISI feature mentioned above. The software classifies the action potentials into pain signals and pain levels. The analysis The analysis algorithms for the adaptive system architecture design use the classified pain signals and the previous stimulation parameters to analyze the situation. Data-driven adaptive system analysis for the pain processing system is defined by a representation of current neural activities, data adaptive simulators, and outcome optimization to form a decision for stimulation parameters. The parameters then synthesize the required stimulation commands that will deliver the required stimulation signals to the neuron. The feedback between stimulation and pain signals to reach optimal stimulation then is complete. The human nervous system receives the stimulation that will produce an inhibition effect on pain and the recorded neurons will respond with a new set of action potentials that represent current neuronal activities. The sensor implants then record the new signals and send to the remote processing module wirelessly. The new action potentials are analyzed by the feedback software and generate a new set of stimulation parameters to be delivered to the stimulator again wirelessly. The cycles continue and an optimal condition, or the most comfortable situation, will be achieved. The data-driven adaptive system analysis will conclude a set of parameters as the decision policy to help reaching the optimal stimulation parameters. In the case any new condition arises to affect the pain level such as body motions or physical condition changes, the closed loop feedback mechanism will be activated again to reach the new optimization with the new decision policy.

Example 10

Demonstration of the Closed Loop Feedback Mechanism

Male Sprague-Dawley rats (300-350 g) were used and the spinal cord was exposed by performing a 3-4 cm laminectomy over the lumbosacral enlargement. A cannula was inserted in the trachea for artificial respiration if needed. The anesthesia was maintained by intravenous administration of sodium pentobarbital at a rate of 5 mg/ml per hour. The pupil reflex was monitored periodically to ensure a proper depth of anesthesia. The spinal cord was immobilized in a stereotaxic frame and covered with mineral oil. The end tidal $CO_2$ was maintained at around 30 mmHg and the body temperature was maintained at 37° C. using a feedback controlled heating pad and a rectal thermal sensor probe.

Figure 32A:
FIGS. 32A and 32B are graphs of the rate of APs and recording signals, respectively, during pressure stimulus without a feedback loop.
Figure 32B:
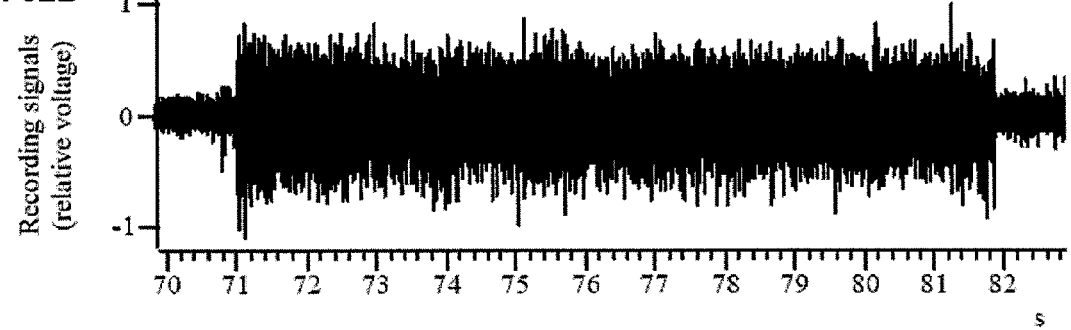

The complete system was constructed with a wireless sensor implant recording lumbar spinal cord dorsal horn neuron activities, a wireless stimulator stimulating PAG or ACC area in the brain and an external with a reader antenna connecting to a computer, in which Labview-based software program is used to analyze the action potentials, apply feedback rules for optimal stimulation parameters, activate the stimulation and synthesize the desired stimulation signals. To demonstrate the feedback loop, several experiments were conducted varying the parameters and decision policies in the Labview-based program described previously. Take one example of the previous experiments, before the feedback loop was applied, the APs, during pressure stimulus from a neuron, were recorded using Spike2. As shown in FIGS. 32A and 32B, the rate immediately rose above 100 spikes/s at the beginning due to pain, and then gradually decreased to around 50 spikes/s at the end of the stimulus.

Figure 32C:
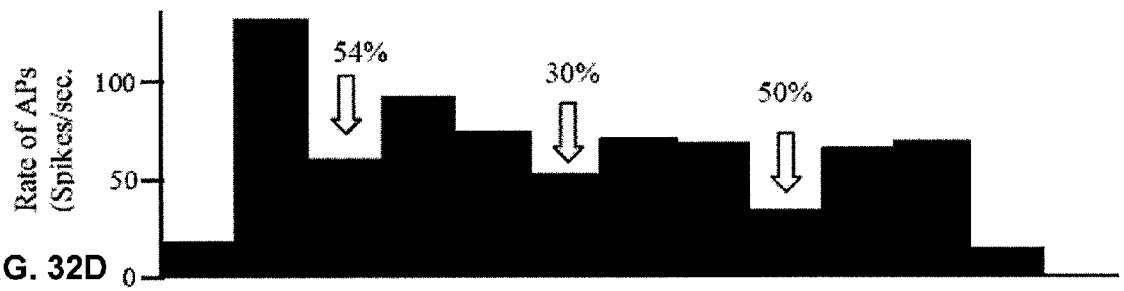
Figure 32D:
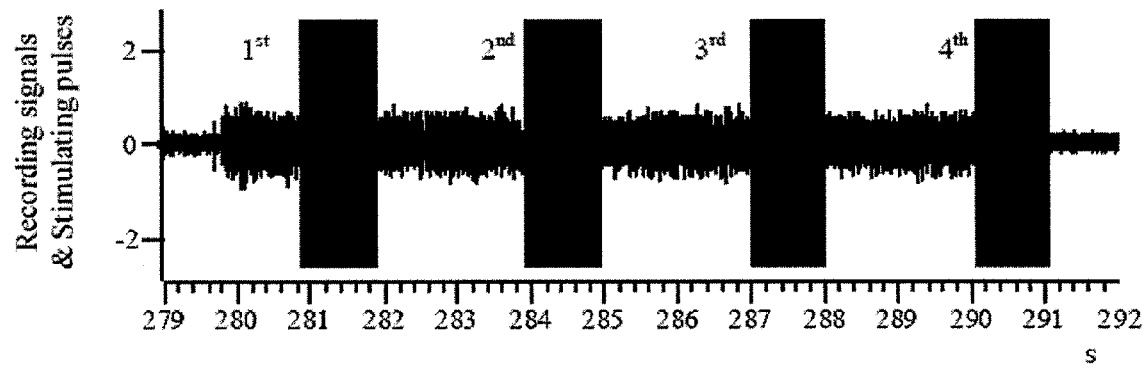

To apply the feedback loop, a pain time slot and rate threshold needed to be set. In this demonstration, the pain time slot was 3 seconds and the rate threshold was 150 spikes during the 3 seconds. The rate threshold was set in the Labview-based program, which is not necessary the same number as shown in the Spike2. The stimulation parameters were fixed at ±2.6V, 140 pulses, 0.7 ms duration and 7 ms interval at the PAG area. FIGS. 32C and 32D shows the rates of APs from the same neuron after the feedback mechanism was applied. The stimulation pulses were also indicated in FIG. 32D. From the results, the rate increased above the threshold and the 1st stimulation was activated. Although the rate of APs reduces 54%, during the stimulation, the total rate of APs in the 3 second time slot was still higher than the threshold, resulting in the 2nd stimulation. The 3rd and 4th stimulation was also activated with the same mechanism.

Figures 33A, 33B:
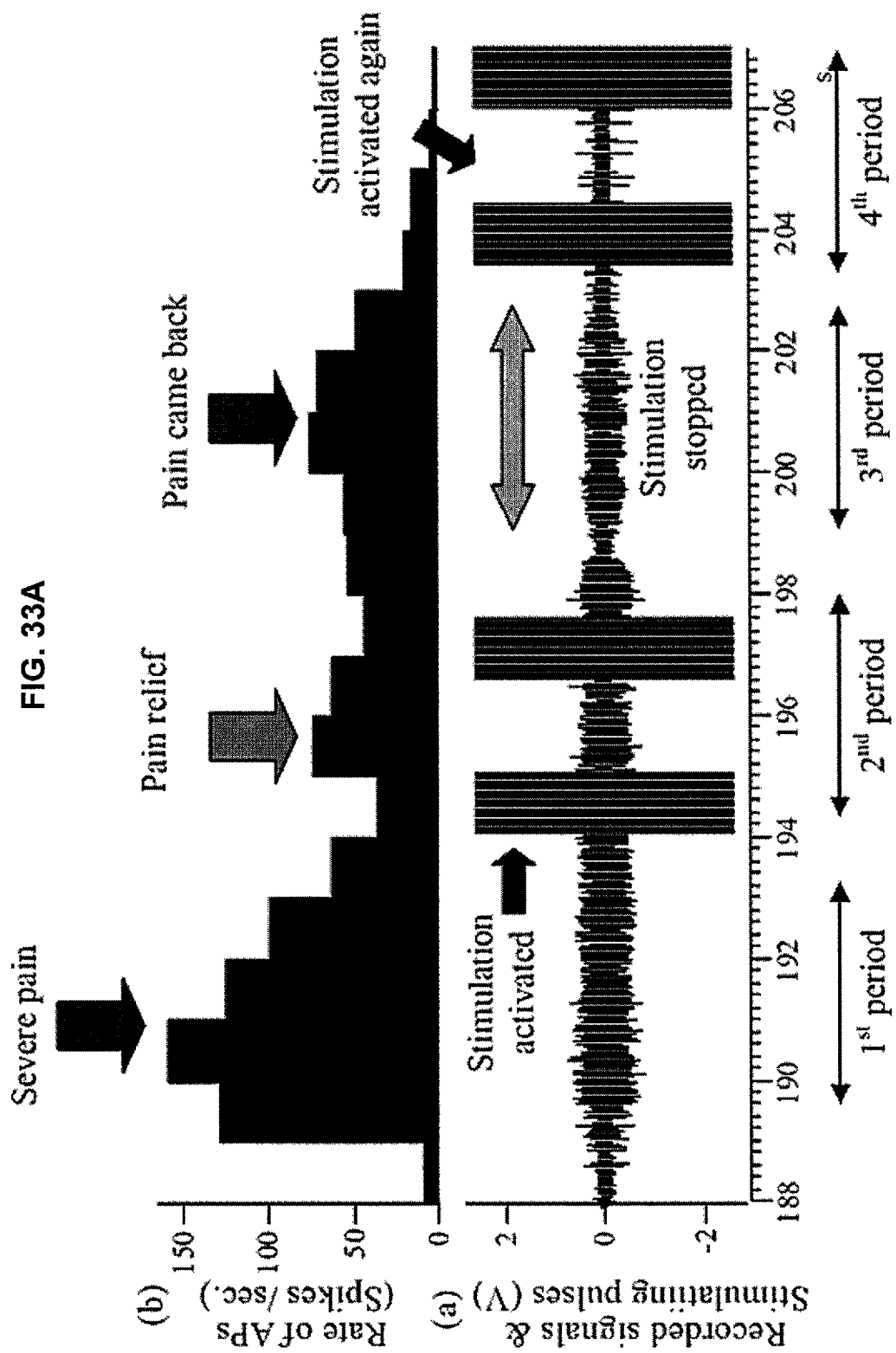
FIG. 33A is a graph of the automatic pain reduction using fixed stimulating pulses with recorded signals and stimulating pulses.
FIG. 33B is a graph of the rate of action potentials of the automatic pain reduction using fixed stimulating pulses.

The results of automatic activation of neuro-stimulation with fixed stimulating pulses are shown in FIGS. 33A and 33B. The stimulating parameters were ±2.6V, 100 pulses, 1.0-ms durations and 10-ms intervals applied to the PAG area. The closed-loop pain relief mechanism can be explained in 4 steps. In the 1st period, the mechanical stimuli were applied resulting in high rates of APs representing severe pain. The high rates exceeded the pain threshold and the neurostimulation was activated in the 2nd period. In this period, pain was inhibited by stimulation and the rate of APs reduced. A second stimulating pulse train was activated in the 2nd period until the rate was lower than the threshold. Thus the stimulation stopped in the 3rd period. Without stimulation, the rates of APs gradually increased meaning pain gradually came back. Once the rate was again higher than the threshold, the stimulation was activated again, as shown in the 4th period. The mechanism continued until the pain signal was completely inhibited. This example shows the efficacy of the automatic feedback mechanism to keep the pain below threshold and optimization to reach maximum pain inhibition.

Another experiment shows the stimulation with various intensities. In this experiment, two sets of stimulation parameters were used for PAG stimulation. The first set was ±1.3V, 100 pulses, 0.5-ms durations and 10-ms intervals, which was considered as a light dose of stimulation. The second set was a stronger dose with ±2.6V, 200 pulses, 1.0-ms durations and 5-ms intervals, which was considered as a higher dose of stimulation. When the stimulation was activated by the action potential rate higher than the threshold, the lower intensity was applied first. If the feedback indicated ineffectiveness which is defined by the user, the stronger intensity was then used for the rest of the stimulation periods. The results are shown in FIGS. 34A-C. When the high pain occurred (at the 326th s), the stimulation was activated giving the pulses with ±1.3V amplitude. However the stimulation did not decrease the pain level effectively as the rates of APs remained higher than the threshold. The $2^{nd}$ and the $3^{rd}$ stimulations with ±2.6V amplitude were thus activated. After the $3^{rd}$ stimulation, the rate of APs decreased lower than the threshold so the stimulation stopped. When the pain came back, a new cycle continued again with the 4th stimulation starting from ±1.3V pulses. This example demonstrated the feasibility of the automatic adaptive closed-loop feedback mechanism for pain management.

The wireless system can record and stimulate at the same time, due to the RFID-based communication, with features of a feedback loop and decision making to activate the stimulation according to the recorded action potential signals. The device is small enough to be carried by a rat, animal, or human. The device is capable of generating stimulating pulses with voltages up to ±18V and various stimulation parameters. The preliminary results in rats showed the feasibility of using the wireless system in a closed-loop mechanism for pain management. From the experiments and results, there would be certain optimal stimulating parameters that give the highest inhibition or the most comfortable level. In general, more pulses, longer pulse durations, shorter pulses intervals and higher voltage levels give better inhibition effects. However, muscle contraction on the rats was observed when the stimulating doses were too high, which will induce uncomfortable feeling in humans. Unnecessary stimulation also consumes extra battery power making practical implant power-inefficient and so inconvenient for patient's use. This implies that the stimulation intensity should be kept as low as possible in practical uses without sacrificing pain reduction. The feedback mechanism, integrated with wireless communication, can potentially reach optimal pain reduction with minimal stimulation.

Given that responses from different neurons and rats may vary, finding optimal parameters to inhibit pain at different potential brain areas may be determined by further systematic experiments. This wireless system can be used with various electrode configurations that are suitable for specific areas. This wireless system provides a tool for studying neuronal activities and enabling chronic pain relief in humans and other neurological disorders.

Example 11

Data Mining in the Wireless Pain Management System

The integrated wireless stimulating and recording device relays identified somatosensory signals from the spinal cord to a computer, which then sends a signal to the wireless stimulator that stimulates specific areas in the brain. By using previously collected data, an analytical strategy that can be applied to form the adaptive analysis system. The data mining analyses are used to identify the factors that impact pain levels, particularly the reduction of pain signals. In addition to the presence of neurostimulation parameters, factors including the graded mechanical stimuli (brushing, pressure, and pinching), the classification of neurons, and rats that are modeled as blocking variables. Three classes of neurons have been identified via clustering. These factors are used to construct regression tree models for predicting pain levels and give the wireless system the decision making intelligence and the ability to adapt to the dynamic conditions of a neurological system to minimize pain over a period of time.

A stimulating electrode was placed at the cerebellum of a rat for stimulation by pulsed electrical currents. The preparation of animals, experimental procedures, signal transmission and data collection were the same as mentioned before. The recording electrode was placed in the spinal cord to search for a spinal dorsal horn neuron, as previously indicated. Dorsal horn neuronal responses to graded mechanical stimuli at the hindpaw were collected in single-unit extracellular recordings.

In the electrical stimulation paradigm, the same spinal cord dorsal horn neuron was recorded in response to graded mechanical stimuli (brush, pressure, and pinch) while various electrical stimulation were applied to the cerebellum simultaneously to show the inhibition effects of the neurostimulation. Each neuron was recorded with a sequence of: (10 s baseline)-(10 s brush)-(20 s interval)-(10 s pressure)-(20 s interval)-(10 s pinch)-(60 s interval)-(10 s baseline)-(10 s brush with cerebellum stimulation)-(20 s interval)-(10 s pressure with cerebellum stimulation)-(20 s interval)-(10 s pinch with cerebellum stimulation)-(60 s interval). Multiple single-cell recordings were taken from each rat's spinal cord. Recordings were performed in both sides of the spinal cord at lumbar 4, 5, and 6 regions. For continuous recording on a single neuron, the recording rate is 12.5 kb/s. Neurons generated action potentials (APs) with time-correlated and location-correlated relationship. The electrode in the spinal cord was able to record multiple spinal cord dorsal horn neurons that can be differentiated by the Labview-based software compared with varied amplitudes and shapes of the action potential template mentioned previously.

The spinal cord signals were recorded with different stimuli with and without cerebellum stimulation. As in the previous examples, pain signals were measured by the rate histogram of the action potentials (spikes/sec) from the corresponding spinal cord neuron. The action potentials are recorded in the spinal cord in real time as the mechanical stimuli are applied periodically.

The k-means clustering algorithm was used to establish a set of neuron groups, in which each group has a similar behavior on the frequency of the pain signals over the type of pain. The k-means clustering algorithm is summarized as follows: Given k seed points, randomly determined, each observation (for each neuron) is assigned to one of the k seed points close to observations, which creates k clusters. Then, seed points are replaced with the mean of the currently assigned clusters. This procedure is repeated with updated seed points until the assignments do not change. The parameters of the k-means clustering algorithm include the distance metric to measure the distance between the points and their mean and the number of clusters (i.e., k). In the present example, Euclidean distance was used as a distance metric and determined an appropriate number k using the silhouette method.

Once the neuron clusters have been determined, certain outcome measures can be predicted, such as the frequency of pain signals, in response to different conditions over time. Regression trees were used, which use recursive binary splitting to uncover structure and have a forward stepwise procedure that adds model terms and a backward procedure for pruning. Variable selection is conducted by only including useful variables in the model. Geometrically, regression trees partition the input variable space into many disjoint sets, where outcomes within a set are more similar than those in different sets. Salford Systems' CART software (Salford systems, San Diego, Calif.) was used to obtain the tree structures.

Figure 35A:
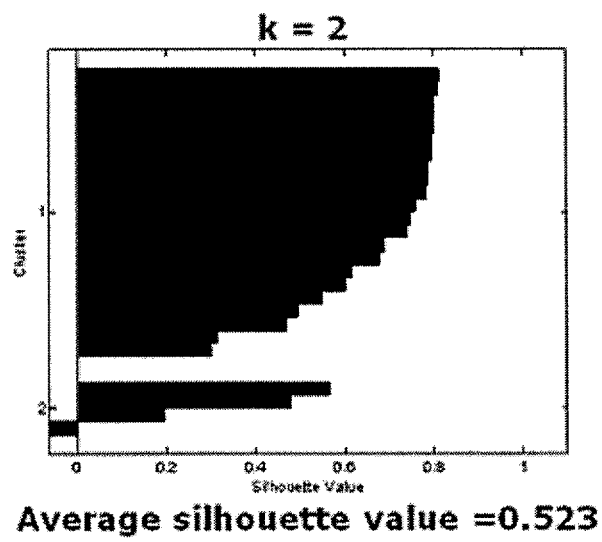
FIGS. 35A-35C are the silhouette plots for k=2, 3, and 4, respectively.
Figure 35B:
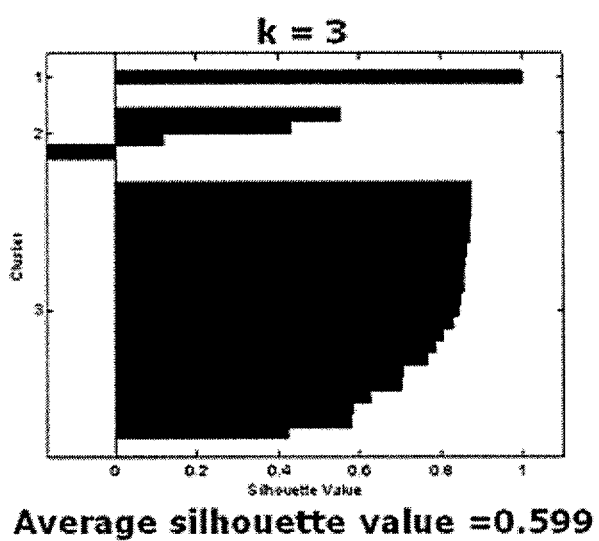
Figure 35C:
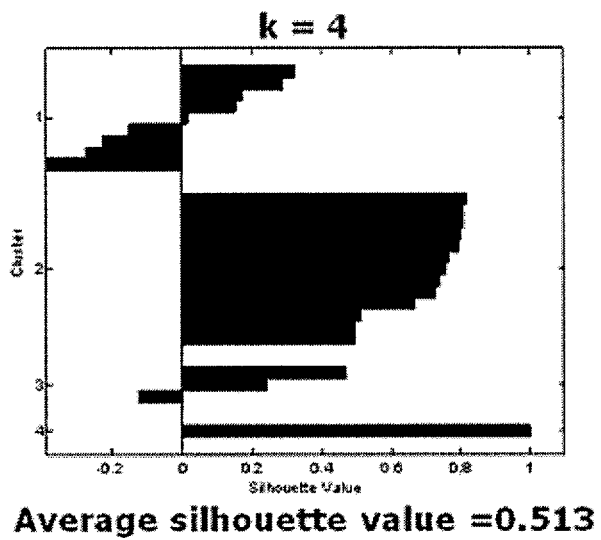

The k-means clustering method to group the pain signals without electrical stimulation was applied as previously indicated. To determine the appropriate number k, the silhouette method was used. The silhouette plots for k=2, 3, and 4 are displayed in FIGS. 35A-35C, respectively, with average silhouette values. It can be seen that three clusters (k=3) yield the largest average silhouette value of 0.599, indicating that the grouping into three clusters using k-means is the best choice. The conclusion also agrees with the three types of pain stimuli applied.

TABLE 2

Predictor variables of regression tree models

| Variable | Descriptions | Types | Details |
|---|---|---|---|
| VOLT | Level of voltage stimulation | Numeric | 5, 10, or 20 volts |
| CLUSTER | Neuron types | Categorical | Three groups (from k-means clustering) |
| TIME | Recorded time during each mechanical stimuli | Numeric | |
| RAT | Different rats | Categorical | Seven rats |
| FREQ_PREV | Frequency of pain signals without neurostimulation | Numeric | |

Figure 36A:
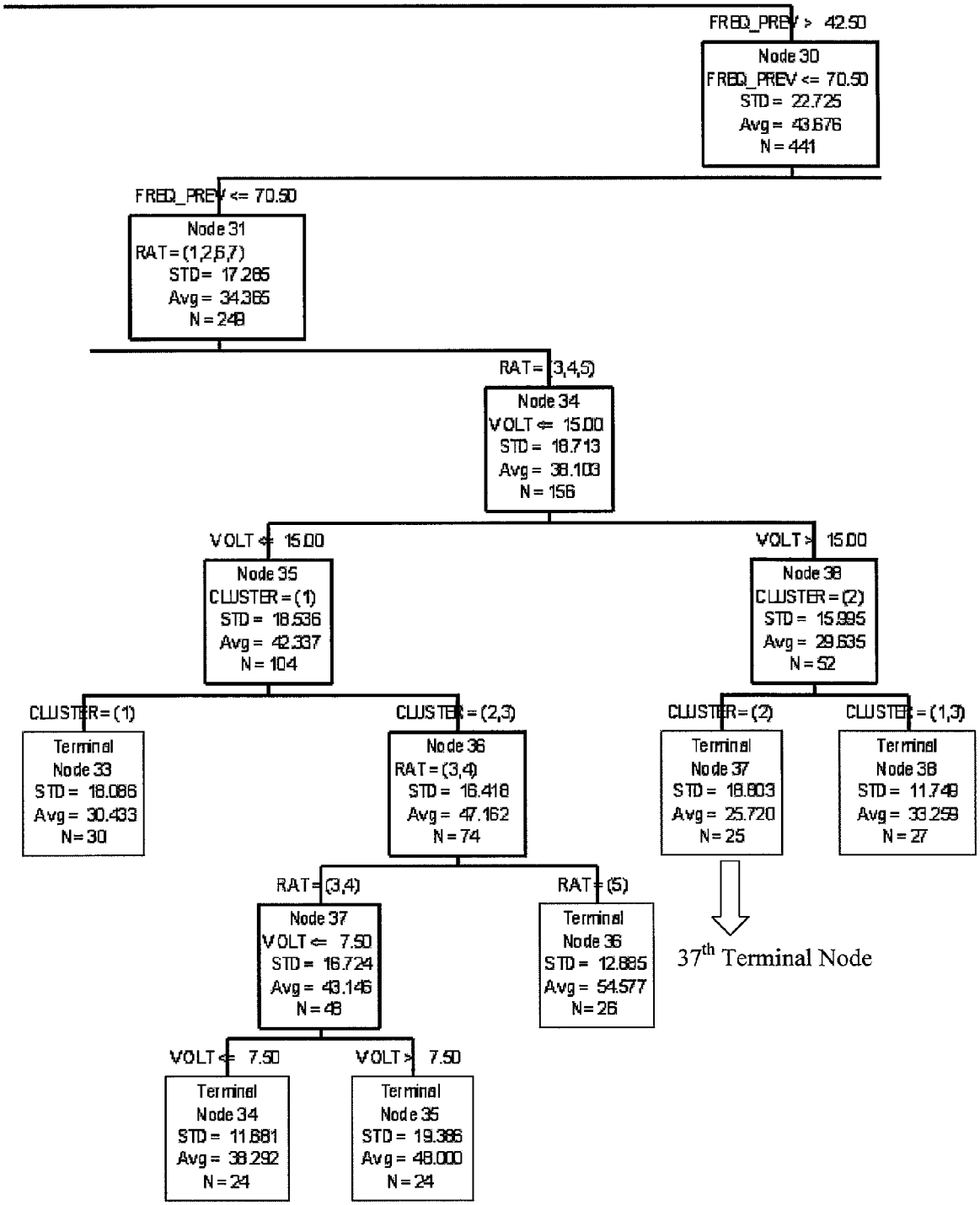
FIG. 36A is an example of the pinching tree model.
Figure 36B:
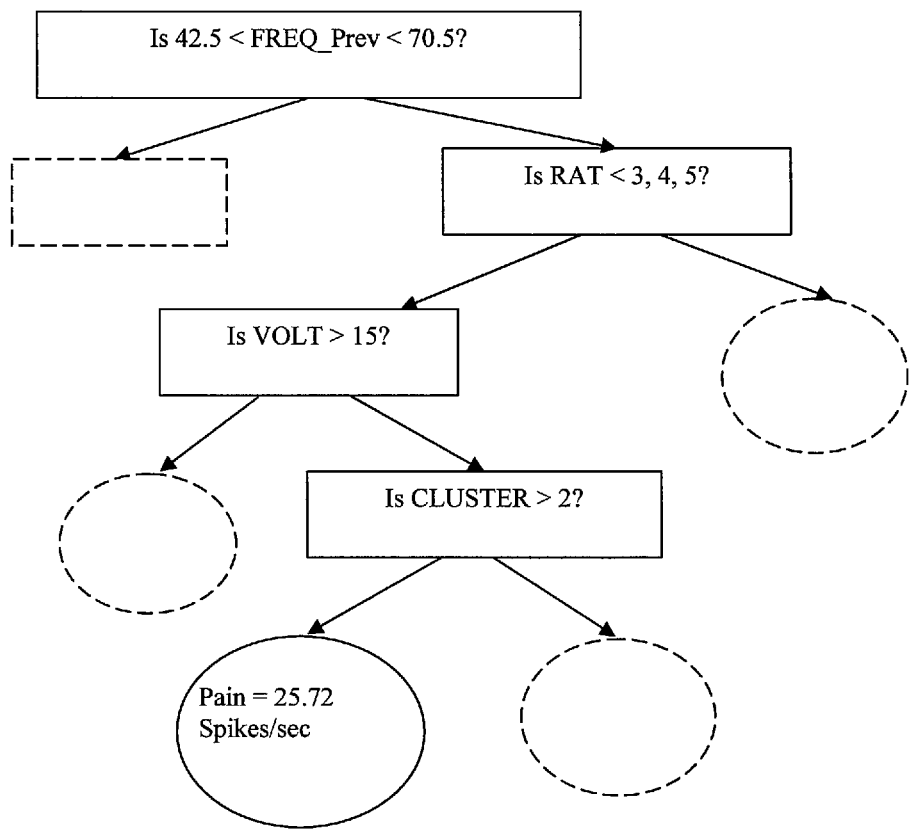
FIG. 36B is a flow diagram for the rule from the 37th terminal node.

A regression tree model for each mechanical stimulus (brushing, pressure, and pinch) was constructed to model the frequency of the pain signals as a function of the predictor variables in Table 2. The number of terminal nodes for the brushing, pressure, and pinching trees are 31, 56, and 45, respectively. Due to the large size of the tree models, only part of the pinching tree model is shown in FIG. 36A. The complete tree has 45 terminal nodes but FIG. 36A only shows 13 terminal nodes as a demonstration. Each pain stimuli will yield such a tree and individual patient/animal will have his/her/its own tree for pain. Each node of the tree specifies conditions that split an existing region. For example, from the 37th terminal node, the following rule was obtained: if FREQ_PREV is between 42.5 and 70.5 spikes per second, RAT is 3, 4, or 5, VOLT is more than 15 volts, and CLUSTER is 2, the prediction of FREQ will be 25.72 spikes per second, as shown in FIG. 36B. In each one of the terminal nodes, the tree provides the decision making parameters to draw the possible conclusion. Since the animal or human nervous system is not deterministic, the conclusion was drawn by probability. The probability for the $37^{th}$ terminal node is N=25 while the probability for the $38^{th}$ terminal node is N=27 with respect to the N=52 in the node $38^{th}$ one level above. As the data collection gets larger as time passes, the tree will receive more data to draw more precise conclusion for this data-driven adaptive system.

For variable selection, the analysis algorithm software can be used with the CART software to provide "variable importance scores." The variable that receives a 100 score indicating the most influential variable for prediction of outcomes in the tree structure, followed by other variables based on their relative importance to the most important one. The importance of predictor variables to predict the frequency of pain signals is given in Table 3. The frequency of pain signal without neurostimulation is most important, followed by the cluster, rat, volt and time variables. In neurostimulation, the effects of CLUSTER and VOLT are most interesting in determining the results, which are in the end of the tree shown in FIG. 36B. This indication will guide the decision policy parameters for the feedback loop mechanism mentioned above. Since each nervous system has its own special characteristics, the priority of various stimulation parameters (voltage, frequency, duration, neuron types) may be different according to their own importance scores in the specific nervous system. The decision policy to prioritize the order of various combinations of stimulation parameters for the wireless feedback loop to try will be based on the continuously recorded neuronal signals. The recorded pain signals will adaptively change the tree structures and relative parameter importance scores. Once the tree structure was established, the incoming pain signal data will refine the tree and achieve an optimized solution until the patient's physiological conditions change again.

TABLE 3

Variables to predict the frequency of pain signals

| Rank | Variable | Variable Importance Score |
|---|---|---|
| 1 | FREQ_PREV | 100 |
| 2 | CLUSTER | 61.5 |
| 3 | RAT | 7.9 |
| 4 | VOLT | 4.6 |
| 5 | TIME | 3.1 |

The k-means clustering method was used to establish a set of neuron groups, in which each group has similar behavior on the frequency of the pain signals over the type of pain. Regression tree models were constructed for predicting the frequency of the pain signals for three different mechanical stimuli. The results of the present example can evaluate different levels of stimulation over time, therefore adding the decision making intelligence and the ability of the wireless feedback system to adapt to the dynamic conditions of a neurological system to minimize pain over the life of the patient. The dynamic optimization using the data-driven adaptive system then provides an optimal control strategy to minimize pain in real time.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims

What is claimed is:

1. A neurostimulation system for mitigating pain comprising:
   at least one implantable sensor that is configured to measure a neuronal signal from a first neuron and to wirelessly transmit the neuronal signal;
   at least one implantable stimulator configured to wirelessly receive a stimulation command signal, wherein the implantable stimulator is configured to generate an electrical signal in response to the stimulation command signal, wherein the generated electrical signal is configured to be applied directly to a second neuron to alter neural activity at the first neuron, wherein the first neuron and the second neuron are on a neural pathway, wherein the neural pathway includes at least one of a spinal-thalamus-somatosensory pathway and a cortico-ponto-spinal decending pathway; and
   a remote processing device configured to:
      receive the wirelessly transmitted neuronal signal from the implantable sensor;
      receive a selection of a pain threshold based on input from a patient;
      determine a pain level based on the wirelessly transmitted neuronal signal;
      determine a stimulation command signal based on the determined pain level and the selected pain threshold; and
      wirelessly transmit the stimulation command signal to the implantable stimulator.

2. The system of claim 1, the implantable sensor comprising a deformable substrate and at least one electrode.

3. The system of claim 1, further comprising a plurality of sensors and stimulators arranged in a wireless body area network, wherein the remote processing device is configured to selectively transmit a stimulation command signal to a particular one of the plurality of stimulators, wherein the particular one of the stimulators includes a radio frequency identification (RFID) mechanism.

4. The system of claim 1, wherein the remote processing device includes software for predicting pain levels and adapting the system to the dynamic conditions of a neurological system.

5. The system of claim 1, wherein determine a pain level comprises predicting a pain level using a regression tree model, wherein the regression tree model is constructed using factors including graded mechanical stimuli and classification of neurons.

6. The system of claim 1, wherein determine a pain level comprises determining a rate of spikes of action potentials.

7. The system of claim 1, wherein determine a stimulation command comprises determining that which increases the intensity of an electrical signal generated by the stimulator relative to the intensity of an electrical signal generated by the stimulator as a result of a previously determined stimulation command if a previously determined pain level was above the pain threshold and a current determined pain level is above the pain threshold.

8. The system of claim 1, wherein the remote processing device is configured to generate a radio-frequency signal, and wherein the sensor is configured to harvest radio-frequency energy from the radio-frequency signal.

9. The system of claim 8, wherein the sensor includes a charge pump, a rectifier, and a pulse generator.

10. The system of claim 8, the radio-frequency signal comprising an identifier and the sensor comprising an identification, wherein the sensor is configured to harvest the radio-frequency energy from the radio-frequency signal if the identifier is the same as the identification.

11. The system of claim 8, wherein the stimulator is configured to harvest the radio-frequency energy from the radio-frequency signal.

12. The system of claim 11, wherein the stimulator includes a charge pump.

13. The system of claim 1, wherein the neural pathway provides a direct electrical connection between the first neuron and the second neuron.

14. The system of claim 1, further comprising a plurality of sensors and stimulators arranged in a wireless body area network, wherein the remote processing device is configured to determine the effect of an electrical signal generated by different combinations of one or more of the stimulators on the neuronal signal measured by different combinations of one or more of the sensors.

15. A method of electrical neurostimulation to mitigate pain comprising the steps:
   recording a neuronal signal from a first neuron with an implanted sensor, wherein first neuron is on a neural pathway, wherein the neural pathway includes at least one of a spinal-thalamus-somatosensory pathway and a cortico-ponto-spinal decending pathway; and
   wirelessly transmitting the recorded neuronal signal to a remote processing device, by the remote processing device:
      receiving a selection of a pain threshold based on input from a patient;
      determining a pain level based on the wirelessly transmitted neuronal signal;
      determining a stimulation command signal based on the determined pain level and the selected pain threshold; and
   wirelessly transmitting the stimulation command signal to an implantable stimulator, wherein the implantable stimulator is configured to apply an electrical signal directly to a second neuron, wherein the second neuron is on the neural pathway; and
   by the stimulator, generating an electrical signal in response to the stimulation command signal, wherein the electrical signal is configured to alter neural activity at the first neuron.

16. The method of claim 15, wherein the sensor is implanted in the spinal cord.

17. The method of claim 15, wherein determining a pain level includes using a regression tree model.

18. The method of claim 15, wherein the stimulation command signal is determined and transmitted when the pain level is greater than the selected pain threshold, wherein the determined pain level is based on an action potential rate.

19. The method of claim 15 wherein the stimulator is implanted in a stimulating site selected from the primary somatosensory cortex (SI), secondary somatosensory cortex (SII), anterior cingulate cortex (ACC), prefrontal cortex, insular cortex, thalamus, septum, and the sensory area of the thalamus, spinal cord, motor cortex, brain stem, periaqueductal gray (PAG), periventricular gray, precentral gyrus, cingulate, caudate, amygdala, parietal cortex, zona incerta, mesencephalic, pontin and medullary retricular formations, superior colliculus, inferior colliculus, nucleus cuneiformis, locus coeruleus, parabrachial nucleus, nucleus ambiguus, nucleus raphe magnus, nucleus reticularis paragigantocellularis, nucleus reticularis gigantocellularis pars alpha (NRGa), raphe pallidus, nucleus tractus solitaris, and spinal trigeminal nucleus spinal cord.

20. The method of claim 15, further comprising a plurality of sensors and a plurality of stimulators implanted throughout the body to form a body area network.

* * * * *